United States Patent
Josel et al.

(10) Patent No.: US 11,965,886 B2
(45) Date of Patent: *Apr. 23, 2024

(54) METHOD OF IMMOBILIZING A CELL ON A SUPPORT USING COMPOUNDS COMPRISING A POLYETHYLENE GLYCOL MOIETY

(71) Applicant: Roche Diagnostics Operations, Inc., Indianapolis, IN (US)

(72) Inventors: Hans-Peter Josel, Weilheim (DE); Dieter Heindl, Munich (DE); Thomas Froehlich, Penzberg (DE); Stefanie Froehner, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 400 days.

This patent is subject to a terminal disclaimer.

(21) Appl. No.: 17/115,069

(22) Filed: Dec. 8, 2020

(65) Prior Publication Data

US 2021/0102944 A1 Apr. 8, 2021

Related U.S. Application Data

(63) Continuation of application No. 15/186,581, filed on Jun. 20, 2016, now Pat. No. 10,890,585, which is a (Continued)

(30) Foreign Application Priority Data

Dec. 20, 2013 (EP) .................................. 13006040

(51) Int. Cl.
*G01N 33/50* (2006.01)
*C12N 5/00* (2006.01)
(Continued)

(52) U.S. Cl.
CPC ..... *G01N 33/56972* (2013.01); *C12N 5/0068* (2013.01); *C12N 11/06* (2013.01);
(Continued)

(58) Field of Classification Search
CPC .... C12N 11/089; C12N 5/0068; C12N 11/06; C12N 11/14; C12N 2503/00;
(Continued)

(56) References Cited

U.S. PATENT DOCUMENTS 10,718,769 B2 * 7/2020 Josel ................. G01N 33/5005
10,890,585 B2 * 1/2021 Josel ..................... C12N 11/06
(Continued)

FOREIGN PATENT DOCUMENTS

EP 1489167 A1 12/2014
JP 2005-312377 A 11/2005
(Continued)

OTHER PUBLICATIONS

Baha, et al., Induction of cell membrane protrusions by biotinylated PEG-cholesterol, Japan Society for Cell Biology, 2001, pp. 59, vol. 54.
(Continued)

*Primary Examiner* — Shafiqul Haq
(74) *Attorney, Agent, or Firm* — Stinson LLP

(57) ABSTRACT

The present invention relates to a method of immobilizing a cell on a support, the method comprising a) providing a compound or salt thereof comprising, preferably consisting of, one or more hydrophobic domains attached to a hydrophilic domain, wherein the one or more hydrophobic domains are covalently bound to said hydrophilic domain, and wherein the one or more hydrophobic domains each comprise a linear lipid, a steroid or a hydrophobic vitamin, and wherein the hydrophilic domain comprises a polyethylene glycol (PEG) moiety, and wherein the compound
(Continued)

comprises a linking group; b) contacting a cell with the compound under conditions allowing the interaction of the compound with the membrane of the cell, thereby immobilizing the linking group on the surface of the cell; and c) contacting the linking group immobilized on the cell with a support capable of binding the linking group, thereby immobilizing the cell on the support.

9 Claims, 41 Drawing Sheets

Related U.S. Application Data continuation of application No. PCT/EP2014/078739, filed on Dec. 19, 2014.

(51) Int. Cl.
| | |
|---|---|
| C12N 11/06 | (2006.01) |
| C12N 11/089 | (2020.01) |
| C12N 11/14 | (2006.01) |
| G01N 33/543 | (2006.01) |
| G01N 33/554 | (2006.01) |
| G01N 33/569 | (2006.01) |

(52) U.S. Cl.
CPC ............ *C12N 11/089* (2020.01); *C12N 11/14* (2013.01); *G01N 33/5005* (2013.01); *G01N 33/54353* (2013.01); *G01N 33/56966* (2013.01); *C12N 2503/00* (2013.01); *C12N 2533/20* (2013.01); *C12N 2533/30* (2013.01)

(58) Field of Classification Search
CPC ............ C12N 2533/20; C12N 2533/30; G01N 33/54353; G01N 33/5005; G01N 33/56972; G01N 33/56966
See application file for complete search history.

(56) References Cited

U.S. PATENT DOCUMENTS

| | | | |
|---|---|---|---|
| 11,021,472 B2 * | 6/2021 | Josel | G01N 33/5005 |
| 2005/0208644 A1 | 9/2005 | Takiguchi et al. | |
| 2017/0146533 A1 | 5/2017 | Josel et al. | |
| 2017/0363624 A1 | 12/2017 | Josel et al. | |
| 2018/0141935 A1 | 5/2018 | Josel et al. | |

FOREIGN PATENT DOCUMENTS

| | | |
|---|---|---|
| JP | 2008-81486 A | 4/2008 |
| JP | 2011-185874 A | 9/2011 |
| WO | 1996/010399 A1 | 4/1996 |
| WO | 2000/051572 A1 | 9/2000 |
| WO | 2001/007011 A1 | 2/2001 |
| WO | 2002/076428 A1 | 10/2002 |
| WO | 2003/074691 A1 | 9/2003 |
| WO | 2008/073458 A2 | 6/2008 |
| WO | 2009/103753 A1 | 8/2008 |
| WO | 2008/147438 A2 | 12/2008 |
| WO | 2010/047793 A2 | 4/2010 |
| WO | 2010141069 A2 | 12/2010 |
| WO | 2011/011055 A1 | 1/2011 |
| WO | 2012/065751 A1 | 5/2012 |
| WO | 2012/094642 A2 | 7/2012 |
| WO | 2013/148579 A1 | 10/2013 |
| WO | 2013/188763 A1 | 12/2013 |

OTHER PUBLICATIONS

Endocytic vesicle, Royal Society of Chemistry, 2019 {retrieved from the internet May 20, 2019),atww.rsc.org/publishing/journals/prospecl/ontology.asp?id=GO:0030139&MSID=c1sm06846f, 1 p.
Jensen, Tor W. et al., Lipopeptides Incorporated into Supported Phospholipid Monolayers Have High Specific Activity at Low Incorporation Levels, Journal of International Search Report dated Mar. 18, 2015, in Application No. PCT/EP2014/078739, 4 pages.
Kato, Koichi et al., Immobilized culture of nonadherent cells on an oleyl poly(ethylene glycol) ether-modified surface, BioTechniques, 2003, pp. 1014-1021, vol. 35, No. 5.
Kato, Koichi et al., Rapid Protein Anchoring into the Membranes of Mammalian Cells Using Oleyl Chain and Polyethylene glycol) Derivatives, Biotechnology Progress, 2004, pp. 897-904, vol. 20.
Kuhn, Phillip et al., A facile protocol for the immobilisation of vesicles, virus particles, bacteria, and yeast cells, ntegrative Biology, 2012, pp. 1550-1555, vol. 4, No. 12.
Michaels, James D. et al., Protection Mechanisms of Freely Suspended Animal Cells (CRL 8018) from Fluid-Mechanical Injury. Viscometric and Bioreactor Studies Using Serum, Pluronic F68 and Polyethylene Glycol, Biotechnology and Bioengineering, 1991, pp. 169-180, vol. 38.
Miura, Suguru et al., Encapsulation of islets with ultra-thin polyion complex membrane through poly(elthylene glycol)-phospholipids anchored to cell membrane, Biomaterials, 2006, pp. 5828-5835, vol. 27.
Palomares, Laura A. et al., Evidence of Pluronic F-68 direct interaction with insect cells: impact on shear protection, ecombinant protein, and baculovirus production, Enzyme and Microbial Technology, 2000, pp. 324-331, vol. 26.
Ramirez, Octavio T. and Mutharasan, R., The Role of the Plasma Membrane Fluidity on the Shear Sensitivity of Hybridomas Grown under Hydrodynamic Stress, Biotechnology and Bioengineering, 1990, pp. 911-920, vol. 36.
Sowana, D. D. et al., Studies of the shear protective effects of Pluronic F-68 on wild carrot cell cultures, Biochemical Engineering Journal, 2002, pp. 165-173, vol. 12.
Teramura et al. Control of cell attachment through polyDNA hybridization. Biomaterials 2010, vol. 31, pp. 2229-2235. (Year: 2010).
Thomas, Colin R. and Zhang, Zhibing, The Effect of Hydrodynamics on Biological Materials, Advances in Bioprocess Engineering II, 1998, 137-170.
Tomeczkowski, J_ et al., Effect of cholesterol addition on growth kinetics and shear stress sensitivity of adherent mammalian cells, Enzyme & Microbial Technology, 1993, pp. 849-853, vol. 15.
Wikipedia, Unified atomic mass unit (Dalton), downloaded from hllps://en.wikipedia.org/wiki/Unified_atomic_mass_unit, Feb. 10, 2017, 5 pages.
Xiao, Kai et al., PEG-0ligocholic acid telodendrimer micelles for the targeted delivery of doxorubicin to B-cell ymphoma, Journal of Controlled Release, 2011, pp. 272-281, vol. 155.
Zhao, Bo et al., Nanotoxicity comparison of four amphiphilic polymeric micelles with similar hydrophilic or hydrophobic structure, Particle and Fibre Toxicology, 2013, 16 pages, vol. 10, No. 47.

\* cited by examiner

Fig. 3

| 30min | target: 300.000 WBC | | MW | STD | Mean % | STD % |
|---|---|---|---|---|---|---|
| well | | | | | | |
| a1 | well treated | 61470 | | | 21,64 | 2,71 |
| a2 | well treated | 67259 | | | | |
| a3 | well treated | 74951 | | | | |
| a4 | well treated | 55956 | 64909 | 8131,2 | | |
| b1 | untreated | 55575 | | | 9,69 | 6,56 |
| b2 | untreated | 32017 | | | | |
| b3 | untreated | 17166 | | | | |
| b4 | untreated | 11481 | 29059,75 | 19683,1 | | |
| c1 | WBC treated | 213072 | | | 77,28 | 4,39 |
| c2 | WBC treated | 237475 | | | | |
| c3 | WBC treated | 243445 | | | | |
| c4 | WBC treated | 233327 | 231829,75 | 13176.7 | | |

| 90min | target: 300.000 WBC | | MW | STD | Mean % | Mean % |
|---|---|---|---|---|---|---|
| well | | | | | | |
| a1 | well treated | 124492 | | | 47,62 | 4,33 |
| a2 | well treated | 143548 | | | | |
| a3 | well treated | 154212 | | | | |
| a4 | well treated | 149208 | 142865 | 13000,28 | | |
| b1 | untreated | 46601 | | | 9,32 | 4,58 |
| b2 | untreated | 29206 | | | | |
| b3 | untreated | 21199 | | | | |
| b4 | untreated | 14882 | 27972 | 13732,98 | | |
| c1 | WBC treated | 237185 | | | 83,12 | 2,72 |
| c2 | WBC treated | 252944 | | | | |
| c3 | WBC treated | 254697 | | | | |
| c4 | WBC treated | 252559 | 249346,25 | 8160,72 | | |

| 120min | target: 300.000 WBC | | MW | STD | Mean % | Mean % |
|---|---|---|---|---|---|---|
| well | | | | | | |
| a1 | well treated | 167671 | | | 57,02 | 6,37 |
| a2 | well treated | 177678 | | | | |
| a3 | well treated | 192194 | | | | |
| a4 | well treated | 146708 | 171062,75 | 19104,5 | | |
| b1 | untreated | 46402 | | | 9,74 | 4,88 |
| b2 | untreated | 35669 | | | | |
| b3 | untreated | 20989 | | | | |
| b4 | untreated | 13798 | 28214,5 | 14633,3 | | |
| c1 | WBC treated | 256949 | | | 86,23 | 2,43 |
| c2 | WBC treated | 268552 | | | | |
| c3 | WBC treated | 258291 | | | | |
| c4 | WBC treated | 250979 | 258692,75 | 7300,9 | | |

Fig. 6B
crude product:
5'- -Chol-TEG- -Chol-TEG- -PEG 2000- -Fluorescein- -Biotin-TEG- -3'
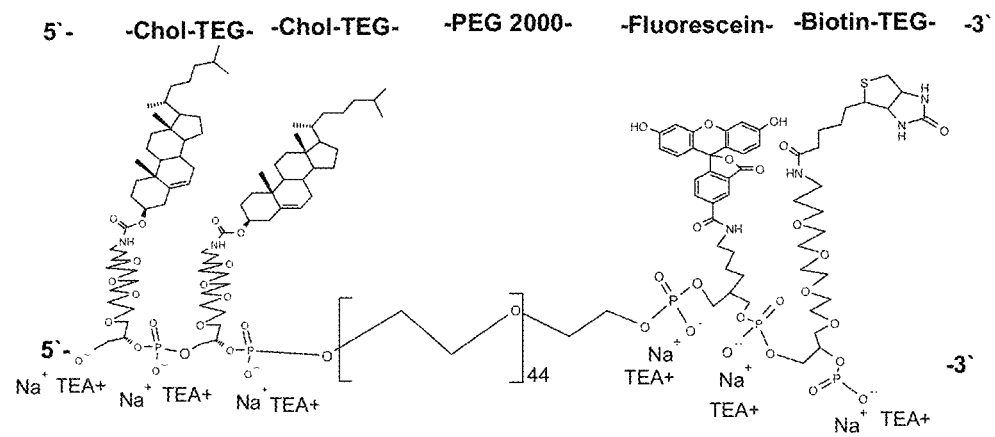
side product 1:
5'- -Chol-TEG- -PEG 2000- -Fluorescein- -Biotin-TEG- -3'
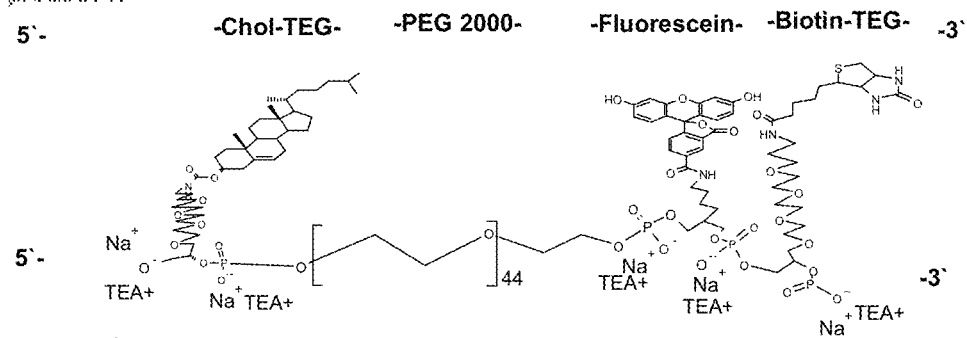
side product 2:
5'- -PEG 2000- -Fluorescein- -Biotin-TEG- -3'
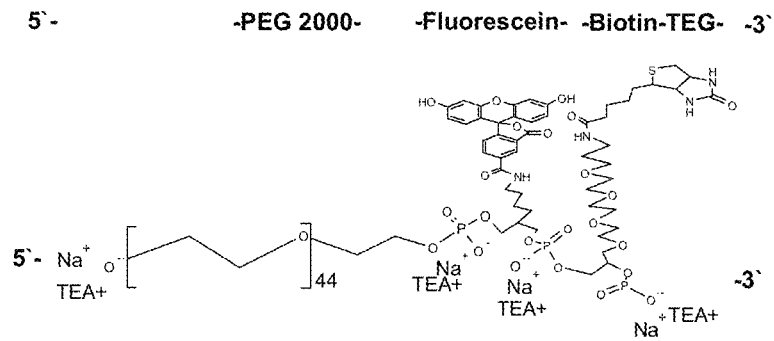
side product 3:
5'- -Fluorescein- -Biotin-TEG- -3'
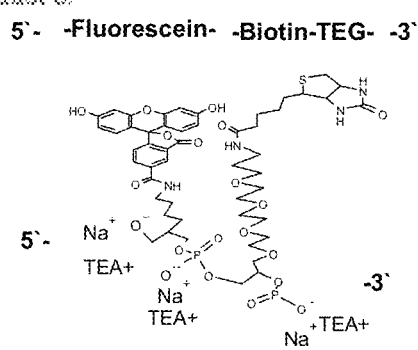
side product 4:
5'- -Biotin-TEG- -3'
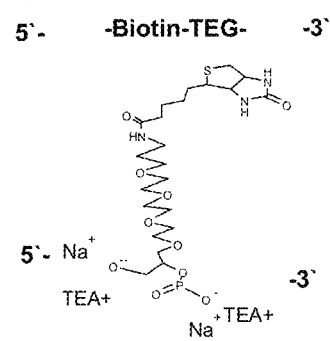

Fig. 6C
crude product:
5'- -myristic acid- -myristic acid- -PEG 2000- -Fluorescein- -Biotin-TEG- -3'
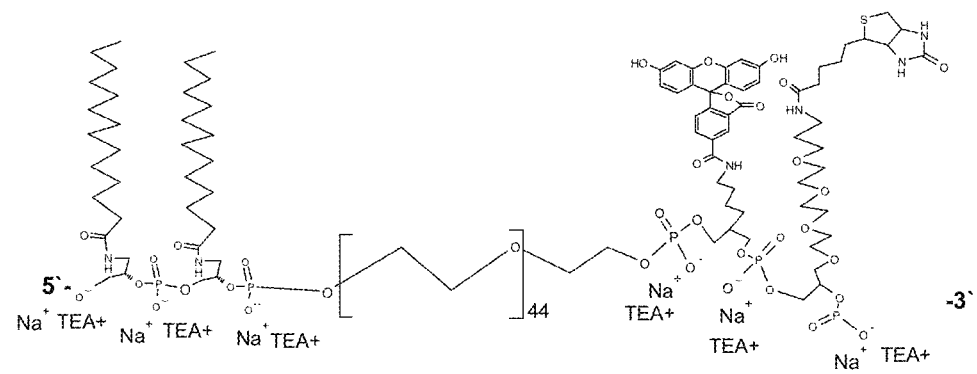
side product 1:
5'- -myristic acid- -PEG 2000- -Fluorescein- -Biotin-TEG- -3'
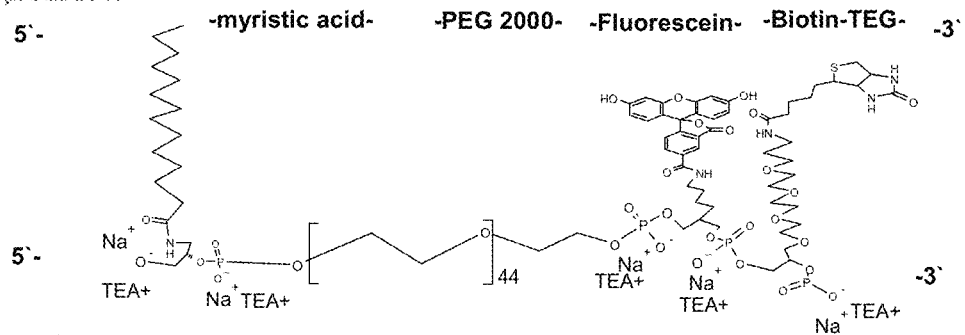
side product 2:
5'- -PEG 2000- -Fluorescein- -Biotin-TEG- -3'
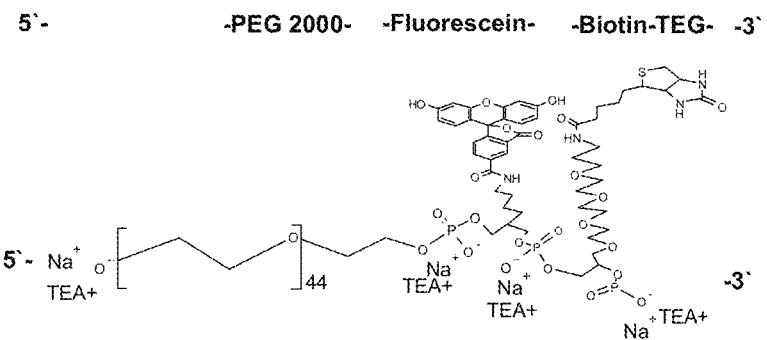
side product 3:
5'- -Fluorescein- -Biotin-TEG- -3'
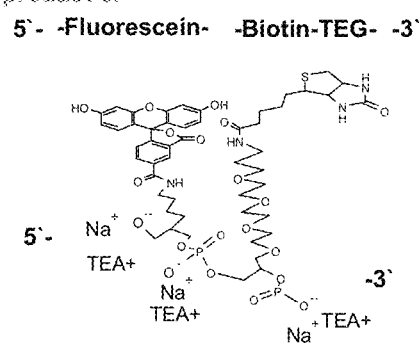
side product 4:
5'- -Biotin-TEG- -3'
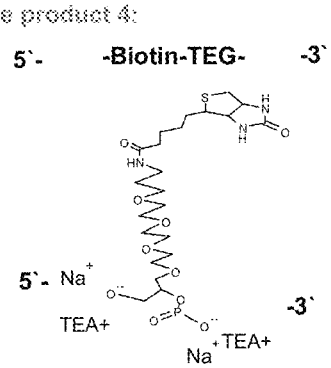

Fig. 6C (continued)
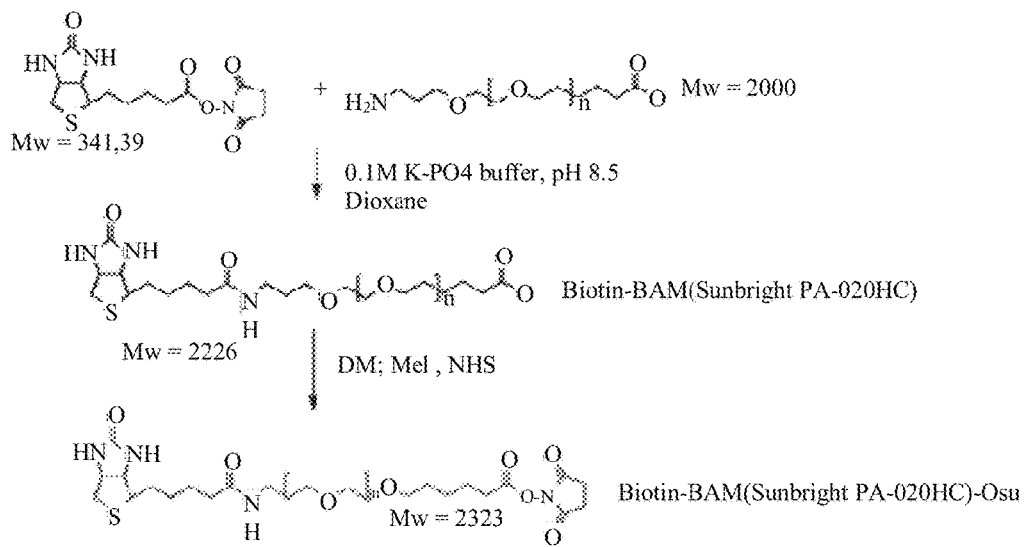
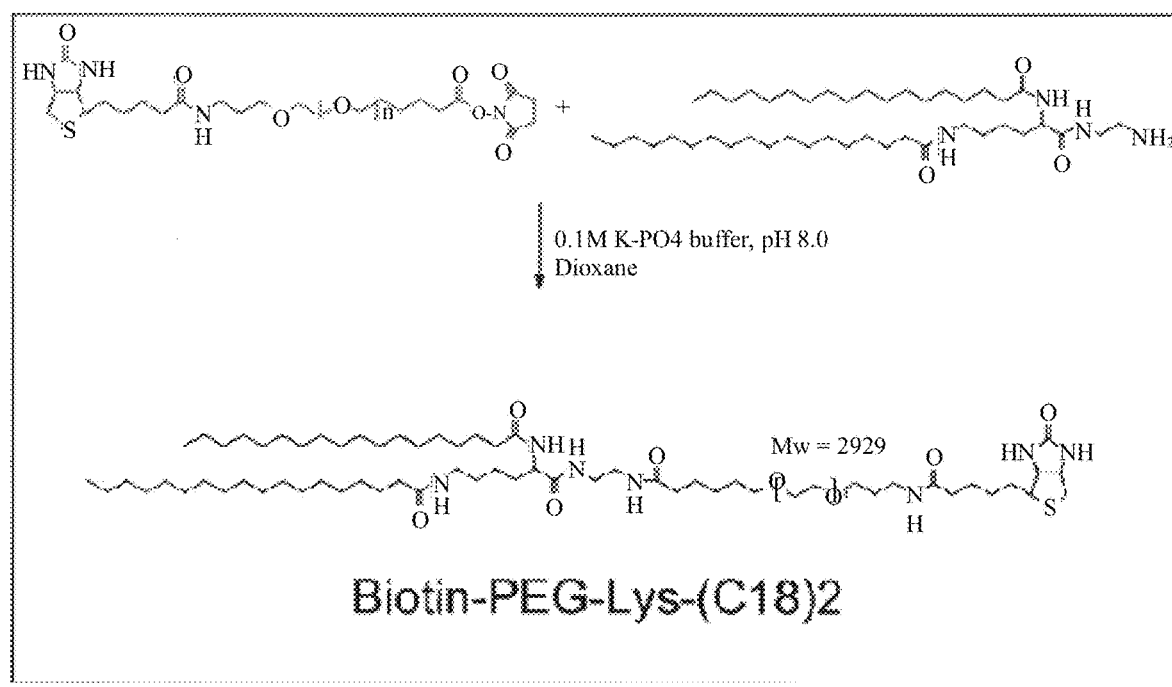

Fig. 12
29891272    Chol-TEG-Chol-TEG-Doubler-Biotin-dT
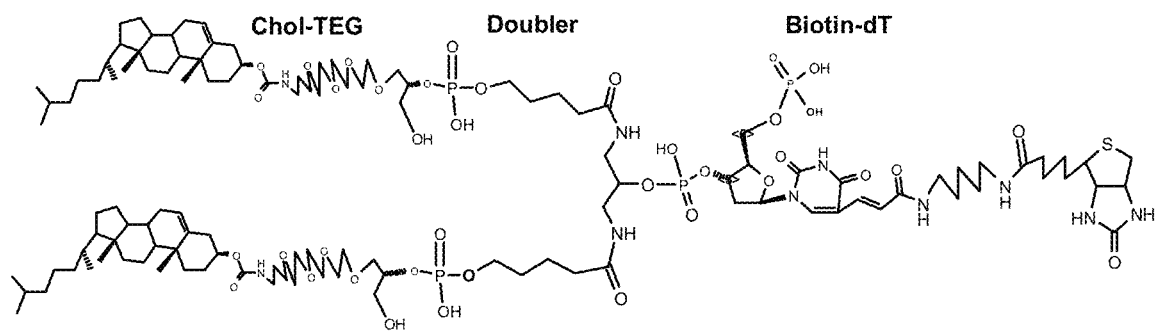
29891227    Myr-Chol-TEG-(Spacer-C18)₇-Fluos-Biotin-TEG
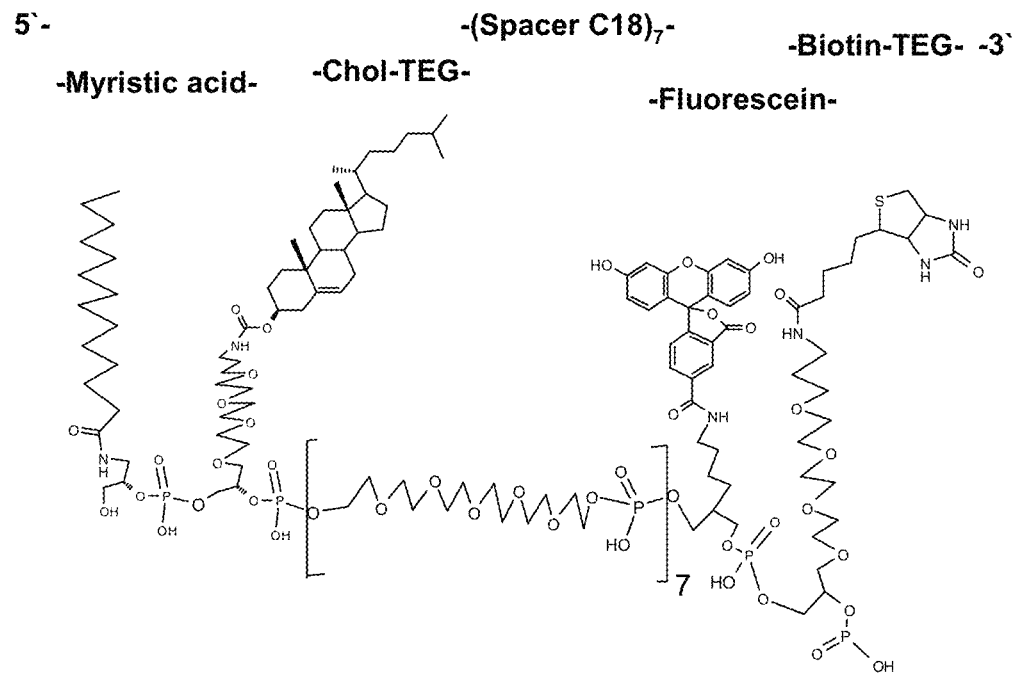

Fig. 12 (continued)
29891228 Chol-TEG- Myr-(Spacer-C18)₇-Fluos-Biotin-TEG
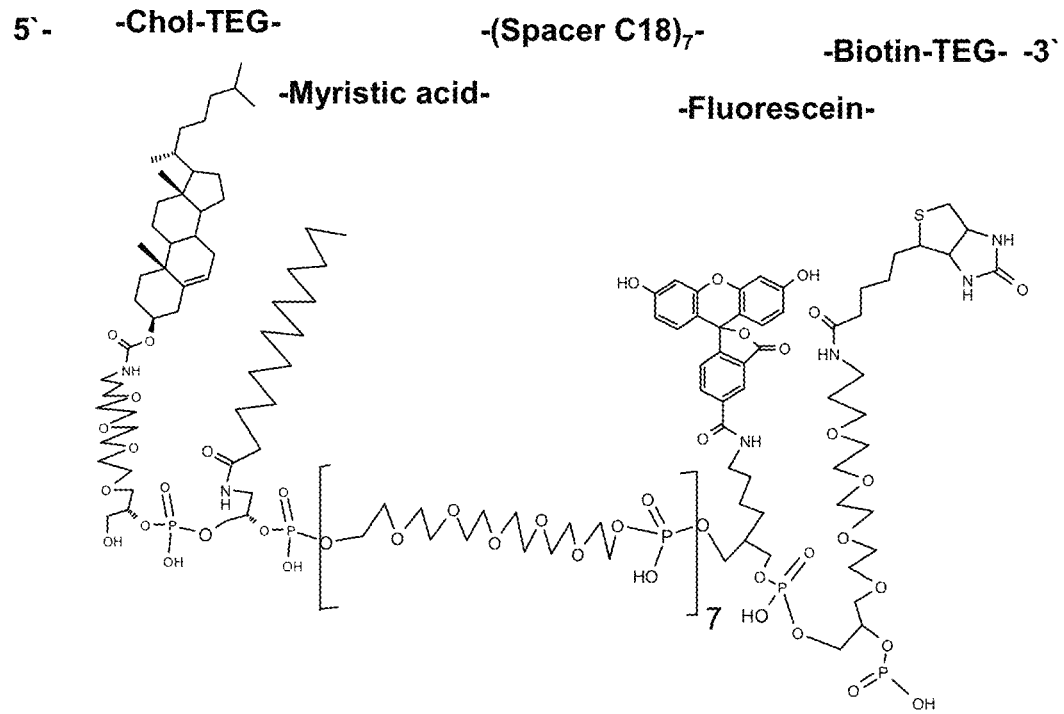
29891180 Chol-TEG-Chol-TEG-PEG2000-Fluos-Biotin-TEG
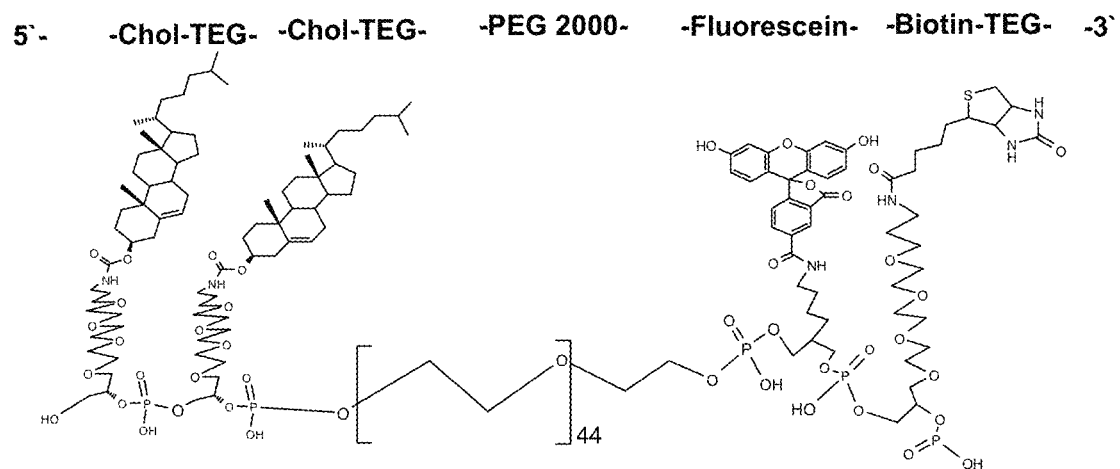

Fig. 12 (continued)
Phosphoramidites used for synthesis:
1 a)
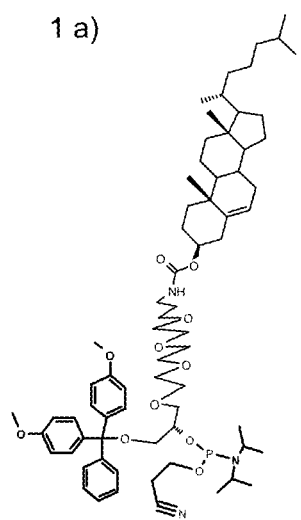
Cholesteryl-TEG-CE-phosphoramidite
a) cholesteryl-TEG-CE-PA (GlenResearch 10-1975),
1 b)
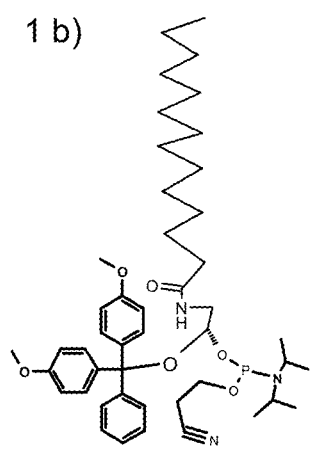
myristic acid-CE-phosphoramidite
b) myristic acid-CE-PA (inhouse production), Fig. 12 (continued)
1 c)
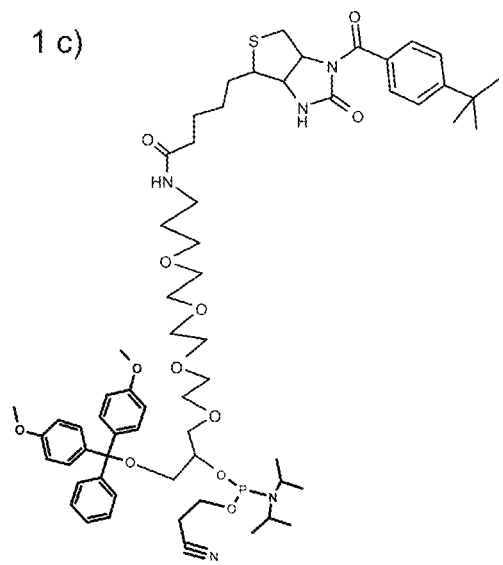
Biotin-TEG-CE-phosphoramidite
c) biotin-TEG-CE-PA (GlenResearch 10-1955),
1 d)
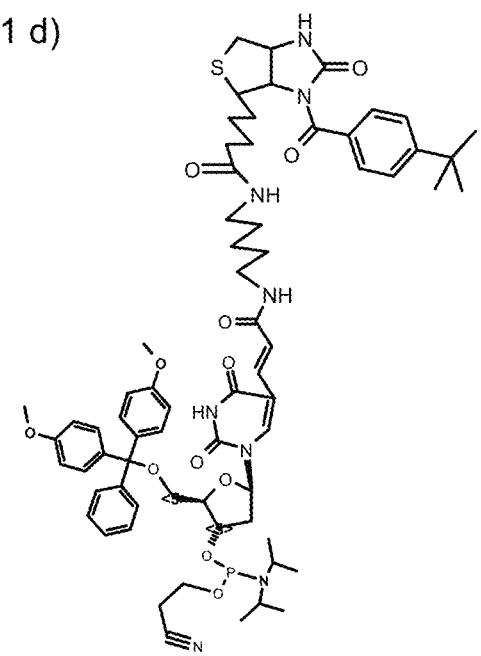
Biotin-dT-CE-phosphoramidite
d) biotin-dT-CE-PA (GlenResearch 10-1038),

Fig. 12 (continued)
1 e)
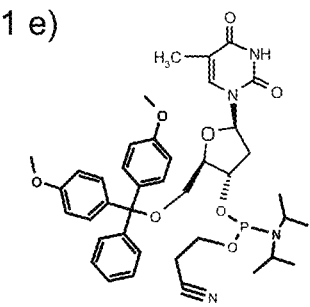
dT-CE-
phosphoramidite
1 f)
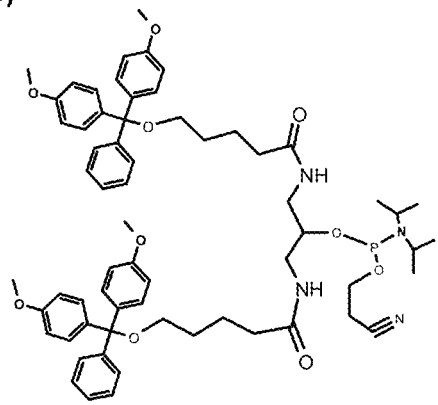
symmetric doubler-CE-
phosphoramidite
f) symmetric doubler-CE-PA (GlenResearch 10-1920), Fig. 12 (continued)
1g
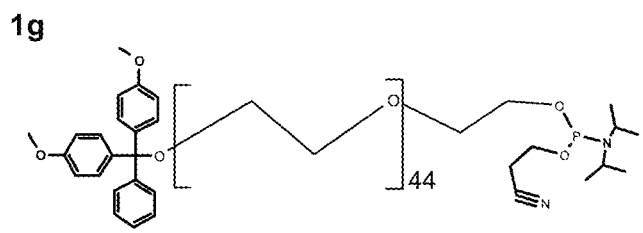
PEG-2000-CE-
phosphoramidite
g) PEG-200-CED-PA (ChemGenes CLP-2119),
1 h)
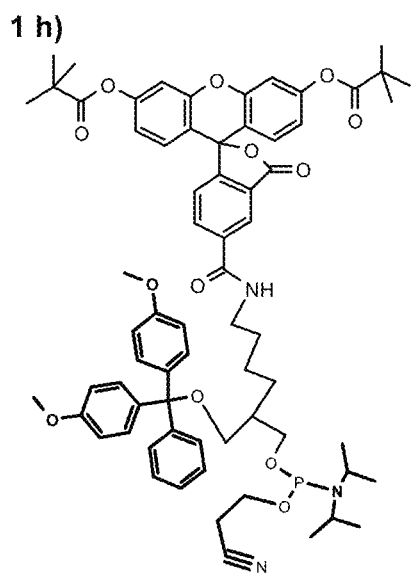
6-Fluorescein-CE-
phosphoramidite
h) 6-Fluorescein-CE-PA (GlenResearch 10-1964)

METHOD OF IMMOBILIZING A CELL ON A SUPPORT USING COMPOUNDS COMPRISING A POLYETHYLENE GLYCOL MOIETY

CROSS REFERENCE TO RELATED APPLICATIONS

This application is a continuation application of U.S. patent application Ser. No. 15/186,581, filed on Jun. 20, 2016, which is a continuation application of PCT/EP2014/078739, filed on Dec. 19, 2014, both of which are hereby incorporated by reference in their entireties.

BRIEF SUMMARY OF THE DISCLOSURE

The present invention relates to a method of immobilizing a cell on a support, the method comprising a) providing a compound or salt thereof comprising, preferably consisting of, one or more hydrophobic domains attached to a hydrophilic domain, wherein the one or more hydrophobic domains are covalently bound to said hydrophilic domain, and wherein the one or more hydrophobic domains each comprise a linear lipid, a steroid or a hydrophobic vitamin, and wherein the hydrophilic domain comprises a polyethylene glycol (PEG) moiety, and wherein the compound comprises a linking group; b) contacting a cell with the compound under conditions allowing the interaction of the compound with the membrane of the cell, thereby immobilizing the linking group on the surface of the cell; and c) contacting the linking group immobilized on the cell with a support capable of binding the linking group, thereby immobilizing the cell on the support.

BACKGROUND OF THE DISCLOSURE

In US2005/0208644A1, a system employing two compounds is used for immobilizing cells. Disclosed therein is a method for immobilizing a cell in a desired pattern on a solid-phase surface by use of a chemical compound having an affinity for the cell. By using of another second chemical compound which is more easily immobilized on the solid-phase surface the first compound is bound to the second compound. The first chemical compound is described as a biocompatible anchor for membrane (BAM). This anchor has an aliphatic group which bines as it is inserted in the cell membrane and it can be immobilized by noncovalent bond without impairing the cells. Kato K. et al., Biotechnol. Prog. 2004, 20, 897-904: describes the so called BAMs (BAM90: one oleyl chain; DOPE-BAM80: dioleylphosphatidylethanolamine) to be useful as an anchoring reagent for proteins into cell membranes as a result of the high water solubility, rapid anchoring ability of the protein in to the outside leaflet of the cell membrane, high retention in the cell membrane and lack of cytolytic activity suggesting that this anchoring technique is promising for cell surface engineering." Kato K. Et al. BioTechniques 2003 35:1014-1021 describe suspension cell attachment by biocompatible anchor molecules, namely Oleyl-O-oly(ethylene glycol)-succinyl-N-hydroxysuccinimidyl-esters on surfaces.

However the compounds of the prior art have several disadvantages. Cell immobilization using such compounds is neither quantitative nor cell-type independent. Also, mixtures of different cell types, e.g. naturally occurring in a blood sample, cannot be attached to a surface quantitatively and independently of cellular phenotypes. In addition binding of the cells to the surface is not tight enough for subsequent processing steps, e.g. immunochemical staining and washing. Another disadvantage of the state-of-the art technology is that linker molecules described can either be internalized by cells or rejected by the cell, finally resulting in release and/or loss of cells.

There is therefore a need for new methods for immobilizing cells without affecting viability and which preferably enable quantification of cells.

BRIEF DESCRIPTION OF THE FIGURES

FIG. 3: shows the results of Example 6 after 30, 90 or 120 minutes incubation.

FIG. 6B: The chemical structures of side products of the synthesis from FIG. 6A.

FIG. 12: shows structures of further compounds useful in methods of the invention and reference compounds, as well as intermediates.

DETAILED DESCRIPTION OF THE DISCLOSURE

The methods of the invention solve this problem and overcome the disadvantages of the prior art. With the methods of the invention employing PEG-based compounds it is possible to capture all types of cells, encompassing suspension and adherent cells.

In one embodiment, the present invention relates to a method of immobilizing a cell on a support, the method comprising
a) providing a compound or salt thereof comprising, preferably consisting of, one or more hydrophobic domains attached to a hydrophilic domain, wherein the one or more hydrophobic domains are covalently bound to said hydrophilic domain, and
  wherein the one or more hydrophobic domains each comprise a linear lipid, a steroid or a hydrophobic vitamin, and wherein the hydrophilic domain comprises a polyethylene glycol (PEG) moiety, and wherein the compound comprises a linking group;
b) contacting a cell with the compound under conditions allowing the interaction of the compound with the membrane of the cell, thereby immobilizing the linking group on the surface of the cell; and
c) contacting the linking group immobilized on the cell with a support capable of binding the linking group, thereby immobilizing the cell on the support.

Figure 4:
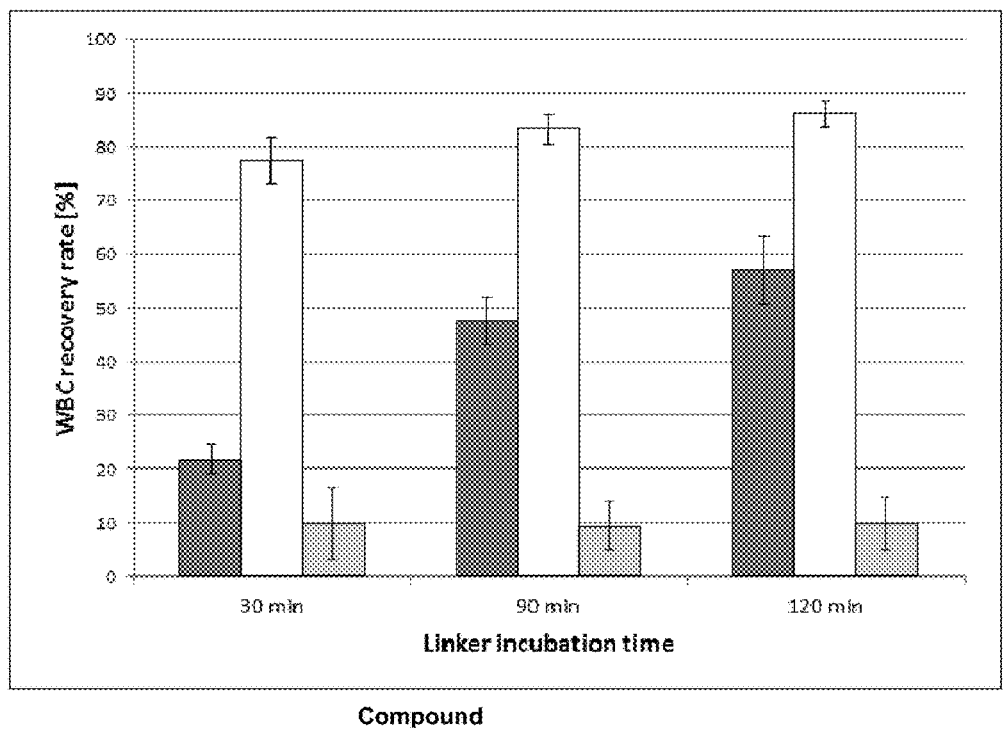
FIG. 4: shows the results of Example 6 after 30, 90 or 120 minutes incubation as a graph.
Figure 5:
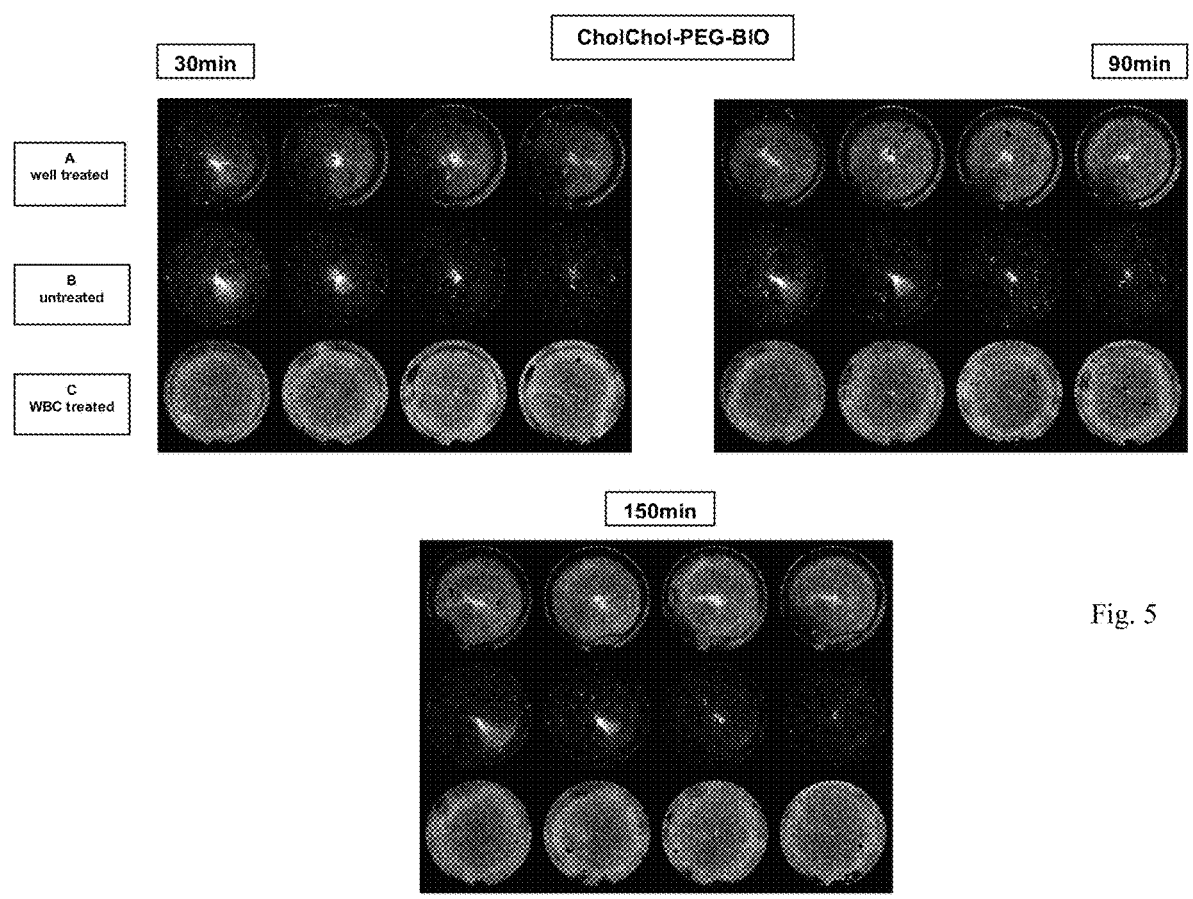
FIG. 5: shows the plates of Example 6 after 30, 90 or 150 minutes incubation.

It was surprisingly found that immobilization of cells is more efficient in case cells are treated with compounds as defined above prior to immobilizing the cells to a support, compared to immobilizing such compounds to a surface and immobilizing cells thereon subsequently (see e.g. FIGS. 3 to 5).

The method of the invention allows immobilizing a cell on a support.

The term "support" or "surface" refers to a material that interacts with reagents in the liquid phase by heterogeneous reactions. Preferably the support is a solid support.

The term "solid support" refers to a material in the solid-phase that interacts with reagents in the liquid phase by heterogeneous reactions. The use of solid supports is well known in the fields of chemistry, biochemistry, pharmacy and molecular biology. Many types of solid supports have been developed depending on the technical problem to be solved. Any of these may be used in the context of the present invention. For example, the solid support used in the methods of the present invention may include components of silica, cellulose acetate, nitrocellulose, nylon, polyester, polyethersulfone, polyolefin, or polyvinylidene fluoride, or combinations thereof. Further suitable solid supports include, but are not limited to, controlled pore glass, a glass plate or slide, polystyrene, and activated dextran. In other aspects, synthetic organic polymers such as polyacrylamide, polymethacrylate, and polystyrene are also illustrative support surfaces. In addition, polysaccharides such as cellulose and dextran, are further illustrative examples of support surfaces. Other support surfaces such as fibers are also operable.

The solid support may be contained in a vessel, wherein the vessel is a tube, such as a centrifuge tube or spin tube, syringes, cartridge, chamber, multiple-well plate, or test tube, or combinations thereof. The solid support may be pre-treated or functionalized in order to allow immobilization of cells. For example, a well-plate may be pre-treated with streptavidin as shown in the examples. In one embodiment, the solid support may be fibrous or particulate usually allowing for appropriate contacting. The size of the solid support suitable for use may vary. The cells may be bound to one solid support only (e.g. one vessel or multi-well plate) or may be bound to a multitude of solid supports (e.g. beads). The shape of the solid support suitable for use may be, for example, a sheet, a precut disk, cylinder, single fiber, or a solid support composed of particulates. In one preferred embodiment, the solid support is flat, or substantially flat with cavities. In one embodiment, the solid support may be fibrous or particulate. The size of the solid support may vary and may be chosen depending from the method or application to be carried out.

In some embodiments, the solid phase is a test strip, a chip, in particular a microarray or nanoarray chip, a microtiter-plate or a microparticle.

The basic principle of immobilizing cells of the compounds which can be used in a method of the invention is that a terminal hydrophobic part of a compound which can be used in a method of the invention anchors into the lipid bi-layer of a cell membrane of interest. The cell can then for example be afterwards attached to a specifically modified surface, and optionally be labeled for visualization and/or detection. Depending on the hydrophobic part, also preferential or exclusive binding to specific cells can be achieved.

In addition, the method of immobilization employs compounds which in addition exhibit advantageous stabilizing effects on cells as shown in detail in the Examples. This is in particular important in case cell viability and/or cell physiology of the immobilized cell is of interest and importance.

In particular, compounds comprising a cholesterol moiety as a hydrophobic moiety are especially preferred.

The stabilizing, in particular shear-protective effect is in particular proven for cholesterol, myristic acid and stearic acid as hybrophobic moieties in the compounds which can be used in a method of the invention (see Example 5).

A polyethylene glycol (PEG) moiety is understood as linear or branched, preferably linear moiety comprising at least one —O—$CH_2$—$CH_2$— moiety, preferably preferably 1 to 50, more preferably 4 to 30 —O—$CH_2$—$CH_2$— moieties.

The basic principle of stabilization—in addition to providing immobilization—is postulated to be that a terminal hydrophobic part of the binding molecule anchors into the lipid bi-layer of the cell membrane. This hydrophobic molecule immobilization decreases the plasma membrane fluidity and therefore stabilizes the cell.

The compounds employed in the method of the invention comprise a linking group.

A linking group is a moiety which is suitable for reversibly or irreversibly, and/or covalently or non-covalently immobilizing a compound to a surface or support, in particular a solid support. In a preferred embodiment, the linking group is an antibody or antigen-binding antibody fragment, a receptor or a binding site thereof, a ligand to a receptor, enzyme or a binding site thereof, a substrate to an enzyme, a tag-binding site, a tag, or a functional chemical group.

A functional chemical group may be for example a thiol group which can be bound to a gold-coated substrate surface by formation of a covalent, irreversible —S—S-bond.

The binding of biotin to streptavidin or antibody or antigen-binding antibody fragment is non-covalent and reversible. Such linking groups employing non-covalent binding to a solid support are preferred in case it is intended to again detach cells for further use, e.g. for administration in a an animal model.

In a preferred embodiment, the linking group may be e.g. a biotin-moiety which allows the non-covalent attachment to a streptavidin-coated surface or support, or a thiol-group which can be bound to a gold-coated substrate surface as solid support.

A particularly preferred linking group according to the present invention is biotin. Compounds comprising biotin as linking group were found to be particularly useful for immobilizing cells, as shown in the Examples.

A lipid is a hydrophobic small molecule selected from fats, waxes, sterols, fat-soluble, hydrophobic vitamins, such as vitamins A, D, E, and K, fatty acids monoglycerides, diglycerides, triglycerides and phospholipids.

A hydrophobic vitamin is a small molecule selected from the group consisting of vitamins A, D, E, and K. In a more preferred embodiment, the hydrophobic vitamin is α-tocopherol.

The compounds which can be used in a method of the invention comprise, preferably consist of, one or more hydrophobic domains, a hydrophilic domain, and a linking group.

Preferably, 1, 2, 3, 4, 5, 6, 7, 8, 9 or 10 hydrophobic domains are covalently bound to said hydrophilic domain.

As shown in the examples, a compound which is used in a method of the invention is contacted with a cell. As immobilization is preferably done with viable or potentially viable cells, the cells are typically present in an aqueous solution, which is preferably buffered and/or contains nutrients, e.g. the cells are suspended in PBS. The compound which is used in a method of the invention may be added to the cells, e.g. in form of a solution, e.g. as aqueous solution by methods known in the art, such as pipetting.

Typically, the compounds are added for example as aqueous solution to a cell suspension of interest. Typically, mixing is performed gently in order to maintain viability of the cells.

Typically, the contacting takes place at a temperature of about 1° C. to 45° C., preferably, 10° C. to 30° C., more preferably 22° to 38° C. Preferably, a temperature is chosen which does not affect viability of the cell.

Also, the contacting typically takes place at a pressure of about 900 to 1100 mbar in order to maintain cell viability.

Also, the cells are preferably incubated with the compounds for a sufficient time to allow for binding. Typically, the cells are preferably incubated with the compounds for 1 minute to 3 days, preferably 5 minutes to 24 h, even more preferably for 10 minutes to 8 hours.

Moreover, the aqueous solution is typically chosen not to affect the integrity and/or viability of a cell.

Such conditions allow the interaction of the compound with the membrane of the cell. Thereby the linking group is immobilized on the cell.

Step c) of the method of the invention relates to contacting the linking group immobilized on the cell with a support capable of binding the linking group, thereby immobilizing the cell on the support. Such contacting may be performed by adding the cells obtained in step b) to a suitable support, e.g. by pipetting the cells obtained in step b) to a suitable support. In this embodiment, the cells of step b) and the support are spatially separated prior to step c). For example a compound disclosed herein comprising a biotin moiety may be immobilized on a cell. After incubation, the cells obtained thereby can be pipetted or otherwise transferred to an array or well plate coated with streptavidin. The biotin and streptavidin moieties will bind, thereby immobilizing the cells to the surface.

Alternatively, the cells obtained in step b) are not spatially separated from the support. In such embodiment, the cells are already e.g. in a well plate, and a compound which can be used in a method of the invention comprising a linking group is added to the cells in suspension, or the compound which can be used in a method of the invention comprising a linking group is present in e.g. a well and the cells, which are suspended in a suitable buffer are added thereto. In this embodiment, the linking group is a moiety which allows binding only under specific conditions, thereby representing a molecular switch. For example, the linking group may be a functional chemical group which reacts with the support capable of binding the linking group only if a co-factor or reactant is added, or a member of a bioaffine binding pair which requires a co-factor for binding, thereby immobilizing the cell on the support.

Preferably, the compounds are contacted with the cells in step b) spatially separated from the surface or support. As shown in the examples, biotin and streptavidin may be used as binding pair. In the examples, biotin was used as linking group of the compounds, and the support capable of binding the linking group is a support coated with streptavidin.

The support capable of binding the linking group is a support which may either be untreated, if the support itself is capable of binding the linking group, as in the case of a gold surface capable of reacting with a thiol group, or may be pre-treated to contain a member of a suitable binding pair, or functional group to react with the linking group. The nature of pre-treatment depends on the chemical nature of the support and the moiety to be attached thereto suitable for binding the linking group. In a preferred embodiment, the support capable of binding the linking group is pretreated, and contains one member of a bioaffine binding pair, in particular the support contains an antibody or antigen-binding antibody fragment, a receptor or a binding site thereof, a ligand to a receptor, enzyme or a binding site thereof, a substrate to an enzyme, a tag-binding site, or a tag bound thereto, preferably covalently bound thereto.

It is understood that the moiety on a pre-treated support is chosen corresponding to the linking group, in order to obtain a support capable of binding the linking group.

In a preferred embodiment, the present invention relates to a method of the invention, wherein the compound comprises, preferably consists of, one or more hydrophobic domains and a hydrophilic domain, wherein the one or more hydrophobic domains are covalently bound to said hydrophilic domain, and wherein the one or more hydrophobic domains each comprise a linear lipid, a steroid or a hydrophobic vitamin, and wherein the hydrophilic domain comprises a compound of Formula (I):

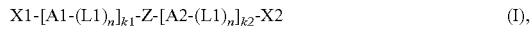

X1-[A1-(L1)$_n$]$_{k1}$-Z-[A2-(L1)$_n$]$_{k2}$-X2     (I), wherein

Z is linear polyethylene glycol (PEG) moiety containing 1 to 100, preferably 1 to 50, more preferably 4-30 —O—CH$_2$—CH$_2$— moieties, wherein the polyethylene glycol moiety optionally comprises 1 or more spacer moieties SP connecting two —O—CH$_2$—CH$_2$— moieties, and wherein the linear PEG moiety optionally comprises a linker moiety L3 at one or both ends, each L1 is a linker moiety selected independently from each other, each n is either 0 or 1, selected independently from each other, A1 and A2 are bifunctional or trifunctional moieties selected independently from each other, with the proviso that at least one A1 or A2 is trifunctional, k1 and k2 are integers between 0 and 10, selected independently from each other, with the proviso that at least one of k1 and k2 is not 0, X1 and X2 are independently selected from hydrogen or a protecting group, L3 is independently selected from a linear alkyl or alkenyl chain with 1 to 10 C atoms, which is optionally (i) interrupted by 1 to 3 N, O or S atoms, and/or (ii) substituted by 1 to 4 hydroxyl, carbonyl, amino or thiol groups, and wherein the one or more hydrophobic domains are covalently bound to said hydrophilic domain via the trifunctional domain(s), and wherein the compound further comprises a linking group, or a salt thereof.

For stabilizing effects, it was found advantageous that the compounds used in the methods of the invention preferably comprise 2 or 3 or more, more preferably 2 or 3 hydrophobic domains. With particular advantage, in a specific embodiment at least one lipid hydrophobic domain comprises a steroid.

In one preferred embodiment of the invention, 2 or 3 or more, more preferably 2 or 3 hydrophobic moieties hydrophobic domains are covalently bound to said hydrophilic domain.

For the general understanding herein, a "hydrophobic moiety" is comprised in and forms the major portion of a "hydrophobic domain", thus determining the hydrophobic character thereof.

The hydrophobic moieties for compounds comprising 2 or more hydrophobic moieties may be the same or may be different. For example, a compound used in the method of the invention comprising two hydrophobic domains may comprise 2 myristic acid moieties, or a myristic acid moiety and a cholesteryl moiety.

The hydrophobic domains each comprise, preferably consist of, a linear lipid, a steroid or a hydrophobic vitamin.

The linear lipid, steroid or hydrophobic vitamin may be bound directly to a trifunctional moiety or via a linker L2. An example for compounds wherein a linear lipid, steroid or hydrophobic vitamin is bound directly to a trifunctional moiety is compound myristic acid-myristic acid-(SpacerC18)7-Fluos-Biotin-TEG. An example for compounds wherein a linear lipid, steroid or hydrophobic vitamin is bound via a linker L2 to a trifunctional moiety is compound Cholesteryl-TEG-Cholesteryl-TEG-(SpacerC18)7-Fluos-Biotin-TEG. In this latter example, TEG (tetraethylenglycol) is the linker L2.

In one preferred embodiment, the hydrophobic domains each consist of a linear lipid, a steroid or a hydrophobic vitamin. In this event, it is apparent that the hydrophobic domain is hydrophobic, more preferably lipophilic as a linear lipid, a steroid or a hydrophobic vitamin is hydrophobic, more preferably lipophilic.

A hydrophobic moiety is understood as moiety that is repelled from a mass of water. Preferably, the moiety is lipophilic; i.e. it tends to dissolve in other non-polar lipophilic substances like fats or fatty acids.

In another preferred embodiment, the hydrophobic domains each comprise a linear lipid, a steroid or a hydrophobic vitamin and one or more further moieties. In this embodiment, the hydrophobic moiety as a whole is hydrophobic, more preferably lipophilic.

In an even more preferred embodiment, the hydrophobic domains of the compounds which can be used in a method of the invention comprising a linear lipid, a steroid or a hydrophobic vitamin, are able to insert into a cell membrane. This can be determined by methods known in the art.

In one preferred embodiment, the 2 or 3 hydrophobic moieties of compounds which can be used in a method of the invention are different hydrophobic domains, or in case of 3 hydrophobic moieties, two are different from the third or all three are different from each other.

In this preferred embodiment of the invention, a first hydrophobic domain comprises, preferably consists of, a saturated fatty acid, especially myristic acid, stearic acid or behenic acid, particularly myristic acid, and/or a second hydrophobic domain comprises, preferably consists of, cholesterol. In case of a third hydrophobic domain, this domain preferably comprises, preferably consists of, cholesterol or a saturated fatty acid, especially myristic acid, stearic acid or behenic acid, particularly myristic acid and/or is the same as the first or second hydrophobic domain.

This conformation was shown to have a higher binding affinity to the cells compared to monovalent molecules; i.e. molecules comprising one hydrophobic moiety of the invention. Therefore lower concentrations of the compounds useful in methods of the invention are needed to reach a shear protective effect compared to monovalent molecules.

The hydrophilic part of the molecule inhibits the internalization of the compound useful in methods of the invention and the shear protective effect is induced by incorporating of the hydrophobic part into the exterior plasma membrane. Experiments with labeled compounds useful in methods of the invention have confirmed that the compound just incorporates in the exterior plasma membrane without influencing the cell interior.

Regarding immobilization, it was found in the Examples that compounds with hydrophobic moieties show a targeting and tight retaining of all cell types (see in particular Example 2). In particular cholesterol, myristic acid, stearic acid, and behenic acid moieties are found to be in particular useful in compounds for use in a method of the invention.

Also, it was found that a method with compounds containing one, two or three hydrophobic moieties was proven in experiments to be advantageous for quantitative cell immobilization.

According to the present invention, a "cholesterol-dual linker molecule" is understood as compound useful in methods of the invention containing two hydrophobic moieties, which are both cholesterol. Accordingly, a "myristic acid-triple linker molecule" is understood as compound containing three hydrophobic moieties, which are all myristic acid.

According to the invention "asymmetric dual linker molecule" is understood as compound containing two hydrophobic moieties, wherein the two hydrophobic moieties are different from each other.

The compounds used in methods of the invention are described in the examples mostly in this modular, schematic way.

Figure 6A:
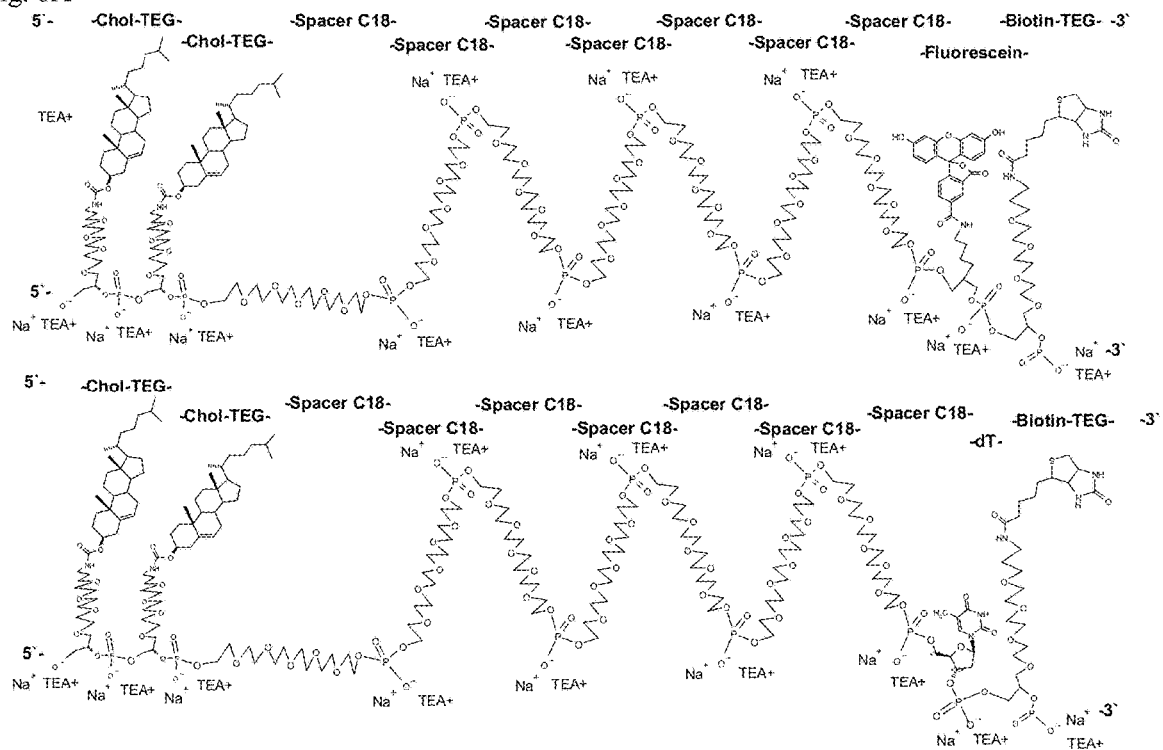
FIG. 6A: The chemical structures of exemplary compounds useful in methods of the invention.

According to the present invention, a compound "Cholesteryl-TEG-Cholesteryl-TEG-(SpacerC18)7-Fluos-Biotin-TEG" as shown in FIG. 6 A) is understood as a compound wherein two cholesterol moieties as hydrophobic moieties are bound to a trifunctional moiety via TEG (tetraethylenglycol).

In accordance with FIG. 6, which shows the modular description of the compounds in parallel to the chemical formula, "(SpacerC18)" is understood as PEG moiety of a length of 18 atoms followed by a phosphate moiety as spacer moiety. -(SpacerC18)7—is accordingly understood as a moiety consisting of 7 "(SpacerC18)" moieties.

According to the present invention "Fluos" is understood as fluorescein moiety bound directly to a trifunctional moiety A2.

According to the present invention "Biotin-TEG" is understood as biotin moiety bound via a linker TEG to a trifunctional moiety A2.

In case of the compounds used in methods of the invention disclosed in this schematic way, the trifunctional moiety A1 typically is glycerol for TEG bound-hydrophobic moieties (see FIG. 6 A). In addition, embodiments with serinol or 6-[(2-hydroxyethyl)amino]-1-Hexanol replacing glycerol as trifunctional moiety are equally disclosed. Other alternatives for such trifunctional moieties are available to the skilled artisan.

The trifunctional moiety A1 is serinol for the compound of FIG. 6 A, wherein the hydrophobic moieties are bound directly to a trifunctional moiety A1.

In an even more schematic way, "Cholesteryl-TEG-Cholesteryl-TEG-(SpacerC18)7-Fluos-Biotin-TEG" can be described to be of the structure "5'-XXYYYYYYYFZ-3'", wherein Y=is a PEG+spacer moiety, X is a hydrophobic moiety bound to the hydrophilic moiety via a trifunctional linker, F is a fluorescent label fluorescein, and Z is a linking group (biotin). 5' and 3' indicate the direction of synthesis by an automated synthesis as shown in the Examples in analogy to nucleotides.

Analogously, -PEG2000- is understood as a PEG2000 moiety; i.e. a polyethylenglycol (PEG) chain consisting of 45 $C_2H_6O_2$ subunits.

In the compounds used in methods of the invention described in the experimental part, L1 is present (n=1) and is phosphate if not explicitly indicated otherwise.

"Spacer" in the context of specifically disclosed compounds used in methods of the invention in the Examples is understood as PEG-moiety including a phosphate moiety. The length of the PEG moiety is determined by e.g. C9 or C12, which indicates that the PEG moiety has a length of 9 or 12 atoms, respectively.

"dT" is understood as thymidine, as exemplified in FIG. 6 B). This moiety dT can be used for determining the concentration of the compounds by absorption and is a bifunctional moiety according to the present invention.

In particular, it was found that a cholesterol-dual linker molecule, a myristic acid-dual or triple linker molecule as well as a stearic acid-dual linker molecule were suitable to achieve quantitative cell immobilization using white blood cells and different cultured cell lines. Moreover, a combination of a cholesterol-dual linker and a myristic-dual linker molecule show a weak increase of the immobilization rate of some cell types compared to the single dual linker molecules.

It has also been shown that an asymmetric dual linker containing both a cholesterol moiety and a myristic acid moiety also show a quantitative cell immobilization.

Moreover, compounds useful in methods of the invention containing 2 or 3 hydrophobic molecules covalently bound to the hydrophilic domain exhibit a tight binding of cells, potentially utilizing a cooperative binding effect. The binding of such molecules to cells is 100-1000 fold stronger compared to binding or immobilization using a compound containing only one hydrophobic molecule.

Furthermore, it is preferred in one embodiment, that the two or three hydrophobic molecules are separated spatially by using linker moieties L1. This is in particular useful for a quantitative immobilization of cells. Utilizing suitable linkers, tailored binding molecules are obtained, being ideally suited in methods of the invention for immobilizing all kinds of rare and regular cells from blood.

In such preferred embodiment, n=1, and L1 is therefore present.

The hydrophilic domain of compounds useful in methods of the invention comprises a PEG moiety and is therefore flexible.

The terminal hydrophobic part(s) of the compounds useful in methods of the invention is/are followed by a long flexible hydrophilic domain.

This hydrophilic domain allows a flexible folding around the cells of interest required for safe embedding of cells, thereby generating a cell-friendly, hydrogel-like environment which is important for keeping the cell morphology and functions alive.

It is possible to use different linear PEG moieties, which differ in length and/or in comprising Spacer moieties like phosphate between PEG moieties in order to achieve a flexible hydrophilic domain. For example a polyethylenglycole (PEG) chain consisting of 45 $C_2H_6O_2$ subunits (PEG2000) (see Example 6 B)) or PEG-moieties with phosphate spacers like—(SpacerC18)7—as described above may be used.

Suitable protecting groups are known in the art. Suitable protecting groups for phosphoramidite chemistry are for example (4,4'-dimethoxytrityl) (DMT), and fluorenomethoxycarbonyl (Fmoc). A particularly preferred protecting group is DMT (4,4'-dimethoxytrityl).

Figure 1:
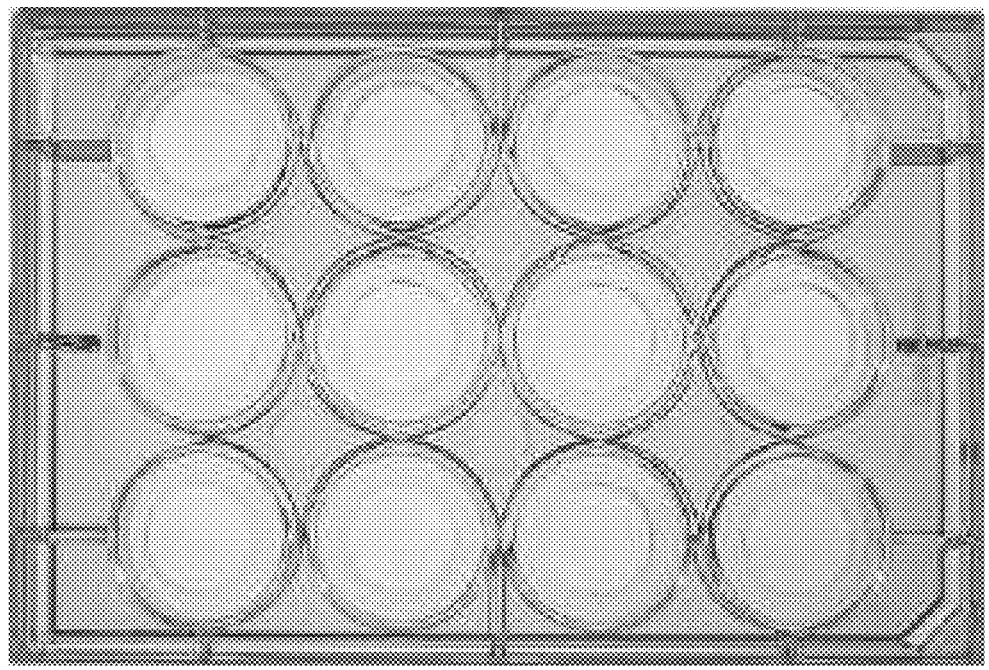
FIG. 1: Plate used in experiment of Example 6: Streptavidin treated MTP (Microcoat), 12 Well, NUNC, MC ID: 604 176, Lot Nr: 1665 C2.

Various salts of compounds used in methods of the invention can be used like Na+ and/or TEA+ salts of compounds useful in methods of the invention, as shown in FIG. 1.

Also other salts are possible and are known to a skilled person. Preferably, salts are used which do not affect or not substantially affect cell viability or function.

In a preferred embodiment of the present invention, the moiety Z in Formula (I) has the following structure:

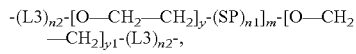

wherein

SP is a spacer moiety, each spacer moiety SP is selected independently from each other, each n1 is either 0 or 1, selected independently for each m moieties, each n2 is either 0 or 1, selected independently of each other, m is an integer from 1 to 100, preferably 1 to 50, more preferably 4 to 30, y is an integer from 1 to 100, preferably 1 to 50, more preferably 4 to 30, y1 is an integer from 0 to 30, preferably 0 to 10, more preferably 0 to 4, with the proviso that $y*m+y1 \leq 100$ and wherein L3 is as defined above.

In a further preferred embodiment of the present invention, n1 is identical for the m moieties —[O—CH$_2$—CH$_2$]$_y$-(SP)$_{n1}$]—.

As can be seen from the examples, n1 is typically either always 0 in compounds useful in methods of the invention, or always 1 in compounds useful in methods of the invention.

An exemplary compound wherein n1=1 is Cholesteryl-TEG-SpacerC12-Cholesteryl-TEG-(SpacerC18)7-Fluos-Biotin-TEG.

An exemplary compound wherein n1=0 is Cholesteryl-TEG-Cholesteryl-TEG-PEG2000-Fluos-Biotin-TEG.

In a further preferred embodiment of the present invention, y1 is 0.

An exemplary compound where y1=0 is Cholesteryl-TEG-SpacerC12-Cholesteryl-TEG-(SpacerC18)7-Fluos-Biotin-TEG.

In a further embodiment of the present invention, y1 is 1.

An exemplary compound where y1=1 is 5'-CholesterylTEG-CholesterylTEG-(SpacerC18)7-SpacerC3-dT-BiotinTEG-3'.

In a further preferred embodiment of the present invention, y is 3, 4, 5, or 6, and n1 is 1. Even more preferably m is 3, 4, 5, 6, 7, 8, 9 or 10.

In a further preferred embodiment of the present invention, the spacer moieties SP are independently from each other selected from the group consisting of a phosphate, and a bifunctional moiety.

It is preferred that all spacer moieties SP are the same. Even more preferably, all moieties SP are phosphate.

A bifunctional moiety according to the present invention is understood as moiety containing two functional groups prior to the synthesis of a compound used in methods of the invention. Such bifunctional moiety is therefore suitable for synthesis of linear compounds. Suitable bifunctional groups are preferably selected from the group consisting of a phosphate group, carbamate group, amide group, a moiety comprising a nucleobase, even more preferably dT, and a linear alkyl group having 1 to 10 C atoms, in particular 1, 2, 3, 4, 5, 6, 7, 8, 9 or 10 atoms, and which alkyl chain contains functional groups at the terminal C-atoms, in particular independently selected from amine, carbonyl, hydroxyl, thiol, carbonic acid groups. Examples of suitable linear alkyl groups with terminal functional groups are diaminoalkyl moieties such as $H_2N$—$(CH_2)_5$—$NH_2$ or hydroxyl-carbonyl moieties such as —C(O)—$(CH_2)_4$—O—.

A trifunctional moiety according to the present invention is understood as moiety containing three functional groups prior to the synthesis of a compound used in methods of the invention. Such trifunctional moiety is therefore suitable for synthesis of a branched compound. Suitable trifunctional moieties are preferably selected from a trifunctional moiety having 1 to 10 C atoms, in particular 1, 2, 3, 4, 5, 6, 7, 8, 9 or 10 C atoms and comprising at least one —OH, —SH and/or at least one —NH2 group, more preferably selected from an amino acid, such as lysine or serine, serinol, —O—CH2-CH(($CH_2)_4$—$NH_2$)—CH2-, glycerol, and a 1,3 diaminoglycerol moiety.

In a further preferred embodiment of the present invention, X1 and/or X2, preferably X1 or X2 is replaced by a hydrophobic domain. An exemplary compound wherein X1 is replaced by a hydrophobic domain is Biotin-PEG-Lys-(C18)2 as shown in the Examples.

In a further preferred embodiment of the present invention, n2 is both 0. In such embodiment, the central linear PEG moiety is directly bound to the moieties X1-[A1-(L1)n]k1 and [A2-(L1)n]k2-X2.

In a further preferred embodiment of the present invention, one or both n2=1, and L3 is an alkyl group with 1 to 10 C atoms which optionally contains an amide group, carbonyl group, carbamate, and/or NH group. In a further preferred embodiment of the present invention, L3 is an alkyl group with 1 to 10 C atoms which optionally contains an amide group, carbonyl group, carbamate, and/or NH group. For example one L3 may be —NH—$CH_2$—$CH_2$NHCO—$CH_2$—$CH_2$— as in the compound Biotin-PEG2000-Lys-(C18)$_2$ of the invention.

In a further preferred embodiment of the present invention, the linear lipid is (a) a saturated or unsaturated fatty acid, and/or (b) a fatty acid having from 8 to 26 C atoms, preferably from 12 to 22 C atoms, more preferably from 14 to 18 C atoms.

A fatty acid is a carboxylic acid with a long aliphatic tail (chain), which is either saturated or unsaturated. Most naturally occurring fatty acids have a chain of an even number of carbon atoms, from 4 to 28.

Examples of saturated fatty acids are caprylic acid, capric acid, lauric acid, myristic acid, palmitic acid, Stearic acid, arachidic acid, Behenic acid, lignoceric acid, and Cerotic acid.

Examples of suitable unsaturated fatty acids are:

| Common name | Δx | Chain length: Double bond |
|---|---|---|
| Myristoleic acid | cis-Δ9 | 14:1 |
| Palmitoleic acid | cis-Δ9 | 16:1 |
| Sapienic acid | cis-Δ6 | 16:1 |
| Oleic acid | cis-Δ9 | 18:1 |
| Elaidic acid | trans-Δ9 | 18:1 |
| Vaccenic acid | trans-Δ11 | 18:1 |
| Linoleic acid | cis,cis-Δ9,Δ12 | 18:2 |
| Linoelaidic acid | trans,trans-Δ9,Δ12 | 18:2 |
| α-Linolenic acid | cis,cis,cis-Δ9,Δ12,Δ15 | 18:3 |
| Arachidonic acid | cis,cis,cis,cis-Δ5,Δ8,Δ11,Δ14 | 20:4 |
| Eicosapentaenoic acid | cis,cis,cis,cis,cis-Δ5,Δ8,Δ11,Δ14,Δ17 | 20:5 |
| Erucic acid | cis-Δ13 | 22:1 |
| Docosahexaenoic acid | cis,cis,cis,cis,cis,cis-Δ4,Δ7,Δ10,Δ13,Δ16,Δ19 | |

In an even more preferred embodiment, the linear lipid is selected from the group consisting of oleic acid, myristic acid, stearic acid and behenic acid, more preferably selected from myristic acid and oleic acid.

In a further preferred embodiment a steroid can be used as hydrophobic moiety.

A steroid is a type of organic compound that contains a characteristic arrangement of four cycloalkane rings that are joined to each other. The core of steroids is composed of seventeen carbon atoms bonded together that take the form of four fused rings: three cyclohexane rings (designated as rings A, B and C) and one cyclopentane ring (the D ring). The steroids vary by the functional groups attached to this four-ring core and by the oxidation state of the rings. Sterols are special forms of steroids, with a hydroxyl group at position-3 and a skeleton derived from cholestane.

In a further preferred embodiment of the present invention,
  (a) the steroid is a sterol, or
  (b) the steroid is selected from the group consisting of cholesterol; a steroid hormone, preferably a gonadal steroid, more preferably an androgen, such as an anabolic steroid, androstenedione, dehydroepiandrosterone, dihydrotestosterone, or testosterone, an estrogen, such as estradiol, estriol, or estrone; a progestagen, such as progesterone or a progestine, a corticosteroid, particularly a glucocorticoid or a mineralcorticoid; an ecdysteroid such as ecdysterone; a phytosterol; a brassinosteroid; a hopanoid; and an ergosterol, more preferably the steroid is cholesterol, or
  (c) the hydrophobic vitamin is α-tocopherol.

In a further preferred embodiment of the present invention, one, two, three or four, preferably one, two or three hydrophobic domains are covalently bound to the hydrophilic domain.

In a further preferred embodiment of the present invention, the two or more hydrophobic domains covalently bound to the hydrophilic domain are different or identical.

In a further preferred embodiment of the present invention, the hybrophobic domain(s) consist of a linear lipid, a steroid or a hydrophobic vitamin.

In a further preferred embodiment of the present invention, the hybrophobic domain(s) comprise, preferably consist of a linear lipid, a steroid or a hydrophobic vitamin covalently bound to a trifunctional moiety A1 via a linker moiety L2.

Such bifunctional and trifunctional moieties were successfully employed in the compounds used in methods of the invention for binding the hydrophobic moieties either directly or via a linker L2.

The linker L2 is independently any linker moiety suitable for covalently binding the hydrophobic moiety to the hydrophilic moiety, and which linker has a length of 50, 30 or 20 atoms or less between the hydrophobic moiety and A1 or A2, respectively.

In one preferred embodiment, linker L2 comprises, preferably consists of, a phosphate group, a moiety —[O—CH$_2$—CH$_2$]$_{y2}$-(SP)$_n$]$_{m1}$-, wherein SP and n are as defined above, preferably n=0, y2 is an integer from 1 to 30, preferably 3 to 10, and m1 is an integer from 1 to 10, preferably 1 to 3, a glycerol moiety, a carbamate group, an amide group, a linear alkyl group having 1 to 10 C atoms, in particular 1, 2, 3, 4, 5, 6, 7, 8, 9 or 10 atoms, and which alkyl chain contains functional groups at the terminal C-atoms, in particular independently selected from amine, carbonyl, hydroxyl, thiol, carbonic acid groups which is optionally substituted by 1, 2, 3, 4 or 5 moieties R1, wherein R1 is independently a C1-C4 alkyl, a C1-C4 hydroxyalkyl, C1-C4 aminoalkyl, a C1-C4 cyanoalkyl, a hydroxyl, a thiol, an amino or a carbonyl moiety. Examples of suitable linear alkyl groups with terminal functional groups are diaminoalkyl moieties such as H$_2$N—(CH$_2$)$_5$—NH$_2$ or hydroxylcarbonyl moieties such as —C(O)—(CH2)4-O—. Preferably, the linear alkyl group is unsubstituted. Even more preferably, the linear lipid, steroid or hydrophobic vitamin is bound to a trifunctional moiety A1 via a linker moiety —(O—CH2-CH2)j-, wherein j is selected from 1, 2, 3, 4, 5, 6, 7, 8, 9 or 10, preferably j is 3, in particular tetraethylenglycol (TEG), a phosphate moiety or a moiety comprising a TEG, glycerol, and a phosphate moiety, or a moiety comprising or consisting of -TEG-glyceryl-phosphate-O—(CH$_2$)$_4$—C(O)—.

In a more preferred embodiment of the method of the invention, the compounds comprise a linear lipid, a steroid or a hydrophobic vitamin covalently bound to a trifunctional moiety A1 via a linker moiety L2, preferably wherein L2 is selected from the group consisting of a phosphate, amide, carbamate, an ester group and a moiety —[O—CH$_2$—CH$_2$]$y_2$-(SP)$_n$]$_{m1}$-, wherein
  SP and n are as defined above, preferably n=0,
  y2 is an integer from 1 to 30, preferably 3 to 10, and
  m1 is an integer from 1 to 10, preferably 1 to 3,
more preferably wherein the linear lipid, steroid or hydrophobic vitamin is bound to a trifunctional moiety A1 via the linker moiety tetraethylenglycol (TEG) or phosphate.

In a further preferred embodiment of the present invention, k1 is 1, 2 3, 4 or 5 preferably 1, 2 or 3.

In a particularly preferred embodiment of the present invention, the hydrophobic domain(s) are covalently bound to said hydrophilic domain only via the trifunctional moiety (s) A1 or via the domain X1-[A1-(L1)$_n$]$_{k1}$ described above. For such embodiments, the further preferred embodiments of the compounds used in methods of the invention also apply. In such compounds, the hydrophobic domains are exclusively localized on one terminal part of the molecule, whereas further groups like the linking group(s), and optionally label moiety(ies) are localized on the other terminal part, spatially separated therefrom.

In a further preferred embodiment of the present invention, k2 is 1, 2 3, 4, 5, or 6 preferably 1, 2 or 3.

In case the compound used in methods of the invention comprises a dT moiety as bifunctional moiety A2, k2 is preferably 3, 4, 5, or 6.

In another preferred embodiment of the invention, k1 is 0, and X1 is replaced by a hydrophobic domain, which preferably comprises a steroid, more preferably cholesterol. In a particularly preferred embodiment, Z is a moiety -(L3)$_{n2}$-TEG (L3)$_{n2}$-, wherein n2 is independently 0 or 1. In an even more preferred embodiment of the present invention, k2 is 1, 2 3, 4, 5, or 6 preferably 3, 4, 5 or 6. Even more preferably one or more, in particular one, further hydrophobic moiety(ies) are bound to moiety -[A2-(L1)n]k2-X2, wherein the further hydrophobic moiety(ies) comprises a steroid, more preferably cholesterol. Even more preferably, L2 is a linker moiety tetraethylenglycol (TEG), phosphate or a moiety comprising a TEG, glycerol, and phosphate moiety or a moiety comprising or consisting of -TEG-glyceryl-phosphate-O—(CH2)4-C(O)—. An exemplary compound used in methods of the invention is ChoI-TEG-ChoI-TEG-Doubler-Biotin-dT shown in FIG. 12.

In case a compound used in methods of the invention comprises a dT moiety as bifunctional moiety A2, k2 is preferably 3, 4, 5, or 6.

In a further preferred embodiment of a method of the present invention, the compound of step a) further comprises a label moiety. Thus, in a further preferred embodiment of the present invention, the compound comprises a label moiety and a linking group.

Such compounds are in particular suitable for methods of the invention where both immobilization and detection of cells is to be achieved, e.g. for localization of immobilized cells or for quantification of cells. An example of such compound is 5'-(Cholesteryl-TEG)2-PEG2000-Fluos-Biotin_TEG-3', which was successfully used in a method of the present invention to immobilize cells to a streptavidin-coated plate and to detect these cells.

Suitable label moieties are moieties suitable for in vitro detection and are known to a skilled person. The detection may be direct, as in the case of luminescence, in particular fluorescence, or indirect in case of an enzyme or substrate thereof.

Thus, both label moieties suitable for indirect or indirect detection may be employed.

"Label" or "label moiety" as used herein refers to any substance that is capable of producing a signal for direct or indirect detection. The label moiety thus may be detected directly or indirectly. For direct detection, a label moiety suitable for use in the present invention can be selected from any known detectable marker groups, like chromogens, chemiluminescent groups (e.g. acridinium esters or dioxetanes), electrochemiluminescent compounds, dyes, or fluorescent dyes (e.g. fluorescein, coumarin, rhodamine, oxazine, resorufin, cyanine and derivatives thereof), luminescent metal complexes, such as ruthenium or europium complexes and radioisotopes.

In indirect detection systems, a first partner of a bioaffine binding pair is a label moiety of the compounds used in methods of the invention; i.e. a first partner is covalently bound to and part of the compound used in methods of the invention. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g. steroid hormone receptor/steroid hormone. Preferred first binding pair members comprise hapten, antigen and hormone. Also preferred are haptens like a tag, digoxin and biotin and analogues thereof. The second partner of such binding pair, e.g. an antibody, streptavidin, etc., usually is labeled to allow for direct detection, e.g. by the label moieties as mentioned above.

Therefore, in a preferred embodiment, the label moiety is a label moiety for direct labeling, or for indirect labeling.

In one preferred embodiment, the label moiety is selected from (a) a direct labeling moiety selected from the group consisting of a chromogen, chemiluminescent group (e.g. acridinium ester or dioxetane), an electrochemiluminescent compound, a dye, a fluorescent dye (e.g. fluorescein, coumarin, rhodamine, oxazine, resorufin, cyanine and derivatives thereof), a luminescent metal complex, such as a ruthenium or europium complex, and a radioisotope; (b) or one of the partners of an indirect detection system, preferably wherein the label moiety is one of the members of the binding pairs selected from the group consisting of (i) hapten or antigen/antibody, (ii) biotin or biotin analogues such as aminobiotin, iminobiotin or desthiobiotin/avidin or streptavidin, (iii) sugar/lectin, (iv) nucleic acid or nucleic acid analogue/complementary nucleic acid, and (v) receptor or receptor fragment/ligand, e.g. steroid hormone receptor/steroid hormone.

Preferred first binding pair members as label moieties suitable for indirect detection comprise hapten, antigen and hormone. Also preferred are haptens like digoxin and biotin and analogues thereof. The second partner of such binding pair, e.g. an antibody, streptavidin, etc., is typically labeled to allow for direct detection, e.g. by the direct label moieties as mentioned above; however, it is also possible to employ an antibody in a compound used in methods of the invention and to use a labeled antigen or hapten for detection.

In the above description of binding pair members, the term antibody is understood to encompass both antibody and antigen-binding fragments thereof.

In a preferred embodiment, the label moiety is a label moiety for direct labeling, even more preferably the label moiety is a fluorescent moiety or dye.

Suitable fluorescent moieties (or dyes) are known in the art and encompass fluorescein, Cy 3, Cy5, Cy5.5, Cy2, Cy3.5, Cy3b, Cy7, an Alexa Fluor dye, a xanthene derivative such as rhodamine, Oregon green, eosin, or Texas red, a cyanine derivative such as cyanine, indocarbocyanine, oxacarbocyanine, thiacarbocyanine, and merocyanine, a naphthalene derivative such as dansyl and prodan derivatives, a coumarin derivative, an oxadiazole derivative, such as pyridyloxazole, nitrobenzoxadiazole and benzoxadiazole, a pyrene derivatives such as cascade blue, an oxazine derivative, such as Nile red, Nile blue, cresyl violet, oxazine 170, an acridine derivatives, such as proflavin, acridine orange, acridine yellow, an arylmethine derivative, such as auramine, crystal violet, malachite green, a tetrapyrrole derivative such as porphin, phthalocyanine and bilirubin.

In the examples, fluorescein was used as representative label. This allows sensitive detection of a label, allowing both localization of a label, and/or quantification. A fluorescent label is a particularly preferred label moiety of the invention.

Suitable radioactive isotopes or radioisotopes for labeling and methods for labeling a compound used in methods of the invention with such radiolabel are known to a skilled person. For example, one of the following isotopes may be used: $^{14}C$, $^{3}H$, $^{32}P$, $^{33}P$, $^{123}I$, $^{125}I$, and $^{131}I$.

In case an antibody or antigen-binding fragments are used as members of the indirect system antibody/antigen or hapten, either an antibody or antigen-binding fragment specific for the epitope or hapten may be part of the compound used in methods of the invention, or the epitope or hapten may be part of the compound useful in methods of the invention. Accordingly, the respective other member may be labeled directly, e.g. with a fluorescent label for subsequent detection. Suitable antibodies or antigen-binding fragments are described below in more detail.

In a preferred embodiment of the invention, the linking group and optionally a label moiety is bound to the moiety X2 [A2-(L1)$_n$]$_{k2}$-X2.

In a particularly preferred embodiment of the present invention, the hydrophobic domain(s) are covalently bound to said hydrophilic domain only via the trifunctional moiety(s) A1 (or via the domain X1-[A1-(L1)$_n$]$_{k1}$ described above), and the linking group and optionally the label moiety is bound to the moiety [A2-(L1)$_n$]$_{k2}$-X2. This ensures spatial separation of the hydrophobic domains for insertion into a cell membrane, and the moieties for immobilization and optionally labelling.

In a more preferred embodiment of the present invention, the compound further comprises a label moiety, wherein a label moiety is covalently bound via the trifunctional moiety A2. For example, such label moiety is a fluorescent dye.

Such compounds are in particular suitable for use in methods of the invention for labelling and detection in addition to immobilization.

In another preferred embodiment of the present invention, the one or more moiety(s) A2 are a label moiety, more preferably wherein a moiety A2 a moiety comprising a nucleobase, even more preferably wherein a moiety A2 is dT, as in case of certain compounds described in the examples.

In another preferred embodiment of the invention, the compound further comprises a label moiety, wherein a label moiety is covalently bound via the trifunctional moiety A2. For example, such label moiety is a fluorescent dye, and one or more moiety(s) A2 are a label moiety, more preferably wherein a moiety A2 a moiety comprising a nucleobase, even more preferably wherein a moiety A2 is dT.

Such compounds comprising dT were used for determination concentration of the compound in the Examples.

In such embodiments, a compound to be used in a method of the invention may comprise a fluorescein and a dT moiety.

In a further preferred embodiment, the linking group is covalently bound via the trifunctional moiety A2, for example the linking group is biotin.

In an even more preferred embodiment, the linking group is covalently bound via the trifunctional moiety A2, and a label moiety is covalently bound via the trifunctional moiety A2.

In a further particularly preferred embodiment of the present invention, the hydrophobic domain(s) are covalently bound to said hydrophilic domain only via the trifunctional moiety(s) A1 (or via the domain X1-[A1-(L1)$_n$]$_{k1}$ described above), and a linking group and label moiety is bound to the moiety [A2-(L1)$_n$]$_{k2}$-X2.

Such compounds further allow both immobilization and labelling, detection and quantification.

In a yet further particularly preferred embodiment of the present invention, the hydrophobic domain(s) are covalently bound to said hydrophilic domain only via the trifunctional moiety(s) A1 (or via the domain X1-[A1-(L1)$_n$]$_{k1}$ described above), and a linking group, but not a label moiety is bound to the moiety [A2-(L1)$_n$]$_{k2}$-X2.

Such compounds can be used if only immobilization of cells bound is intended.

In an even more preferred embodiment of the present invention, a compound used in methods of the invention comprises a label moiety and a linking group, wherein the label moiety is a fluorescent label and the linking group is biotin.

In another preferred embodiment of the present invention, the compound does not further contain a label moiety. An exemplary compound is 5'-CholesterylTEG-CholesterylTEG-PEG2000-BiotinTEG-3.

In a further preferred embodiment of the present invention, the linkers L1 are independently selected from the group consisting of a phosphate, amide, carbamate, and an ester group.

In a further preferred embodiment of the present invention, the moieties A1 and A2 are independently selected from a bifunctional group selected from the group consisting of a phosphate group, carbamate group, amide group, a moiety comprising a nucleobase, even more preferably dT, and a linear alkyl group having 1 to 10 C atoms and which alkyl chain contains functional groups at the terminal C-atoms, in particular independently selected from amine, carbonyl, hydroxyl, thiol, carbonic acid groups, and a trifunctional moiety having 1 to 10 C atoms and comprising at least one —OH, —SH and/or at least one —NH$_2$ group, preferably selected from lysine, serine, serinol, —O—CH$_2$—CH ((CH$_2$)$_4$—NH$_2$)—CH$_2$—, a glycerol, and a 1,3 diaminoglycerol moiety.

In a further more preferred embodiment of the present invention, the linkers L2 are independently selected from the group consisting of a phosphate, amide, carbamate, an ester group and a moiety

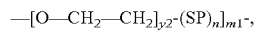

wherein
SP and n are as defined above, preferably n=0,
y2 is an integer from 1 to 30, preferably 3 to 10, and
m1 is an integer from 1 to 10, preferably 1 to 3.

Figure 6C:
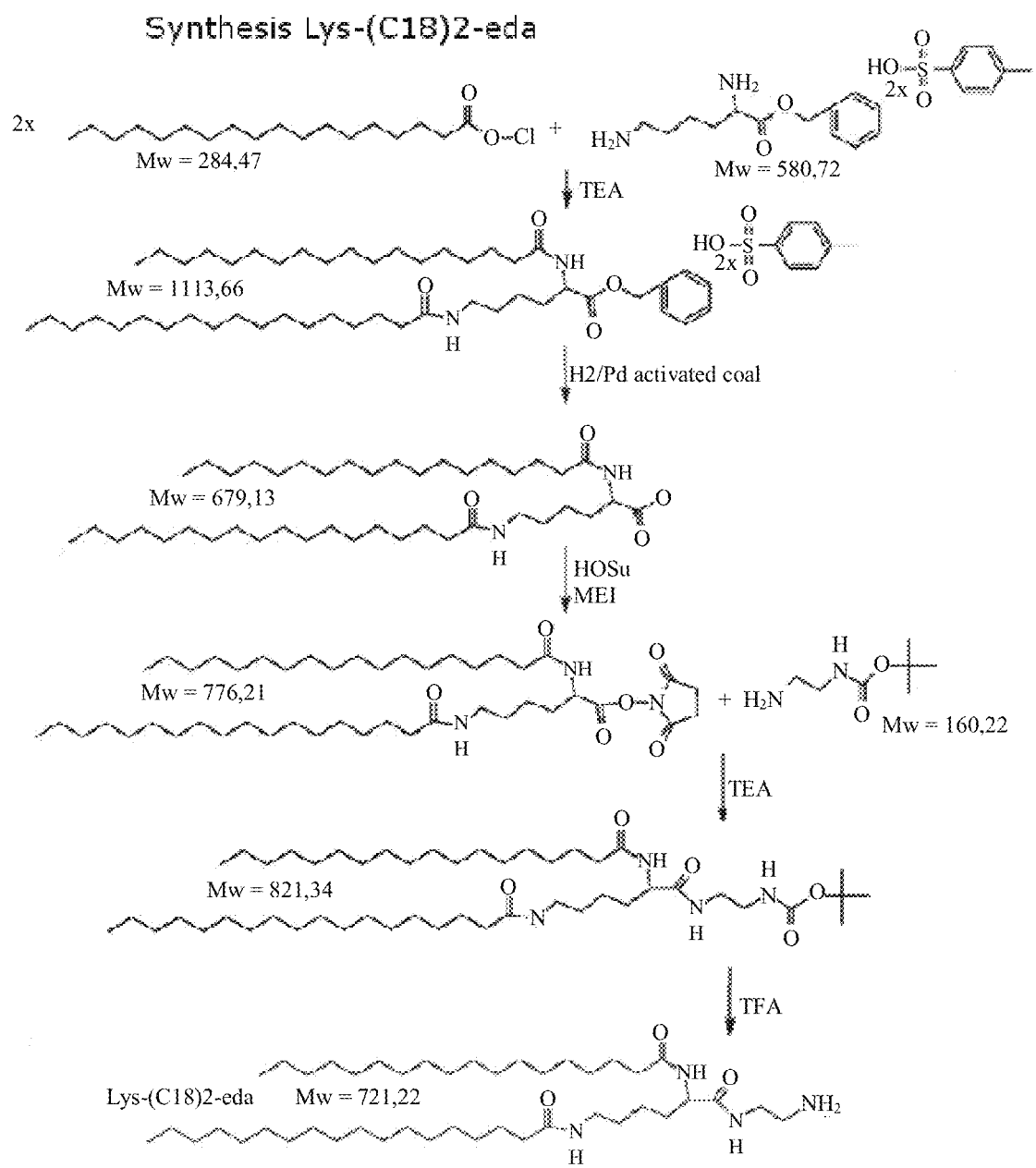
FIG. 6C: The synthesis of Biotin PEG Lys (C18) as well as side products of the synthesis.
Figure 7A:
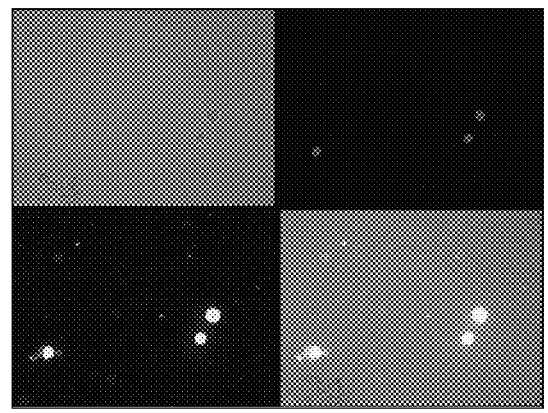
FIG. 7A: shows staining of cell with cholesteryl-containing compound with internal reference 29.891180. Representative pictures according to Example 3 throughout FIGS. 7A-7E.
Figure 7B:
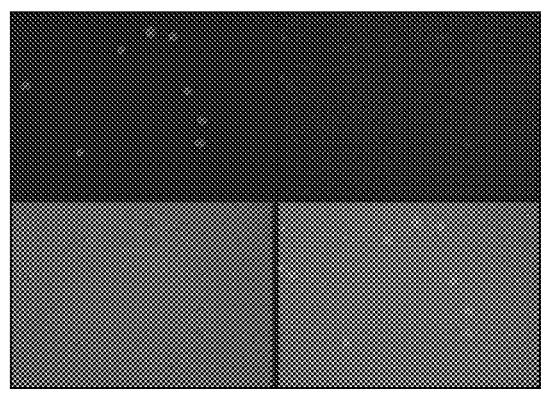
FIG. 7B: shows staining of cell with myristic acid containing compound with internal reference 29.891194.
Figure 7C:
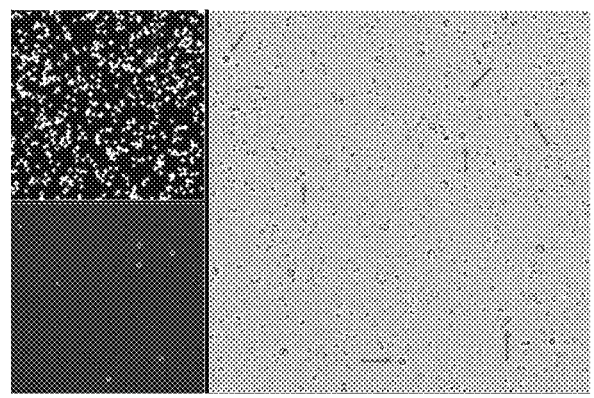
FIG. 7C: shows staining of cells with MDA-MB468.
Figure 7D:
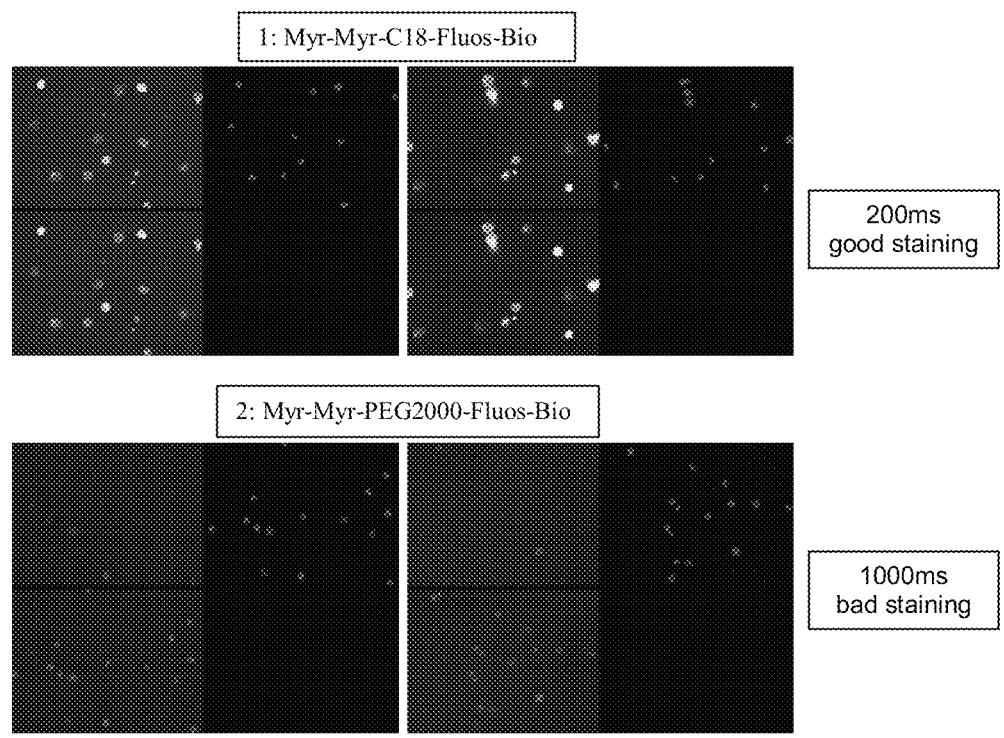
FIG. 7D: shows staining of cells staining of cells for different exposure times with different compounds indicated schematically.
Figure 7E:
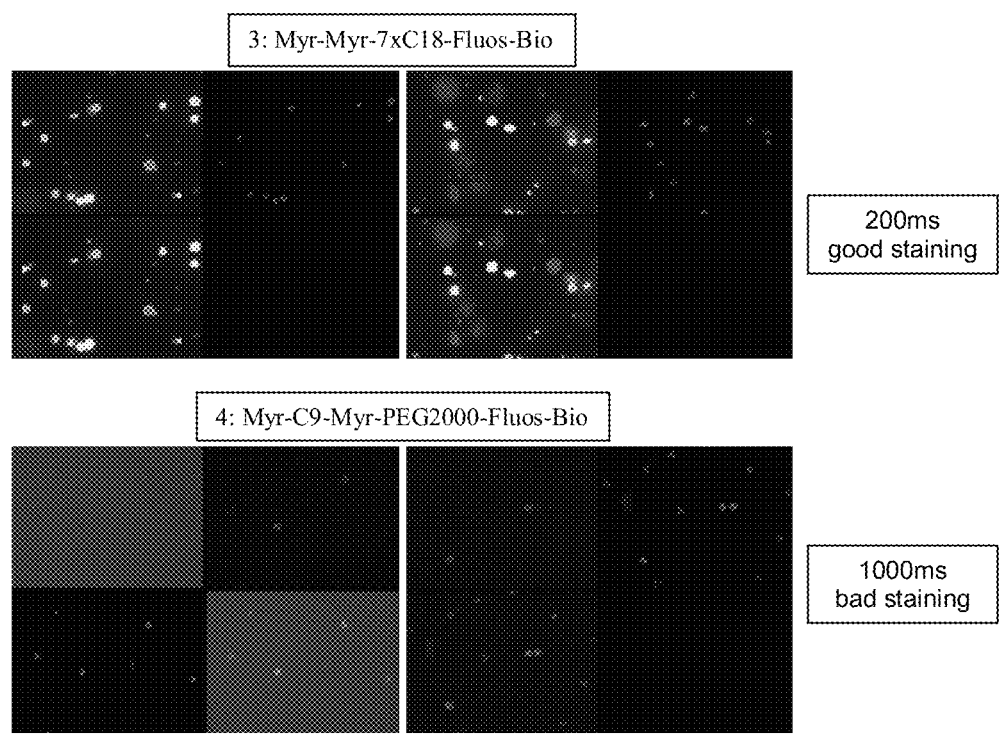
FIG. 7E: shows staining of cells staining of cells for different exposure times with different compounds indicated schematically.
Figure 8A:
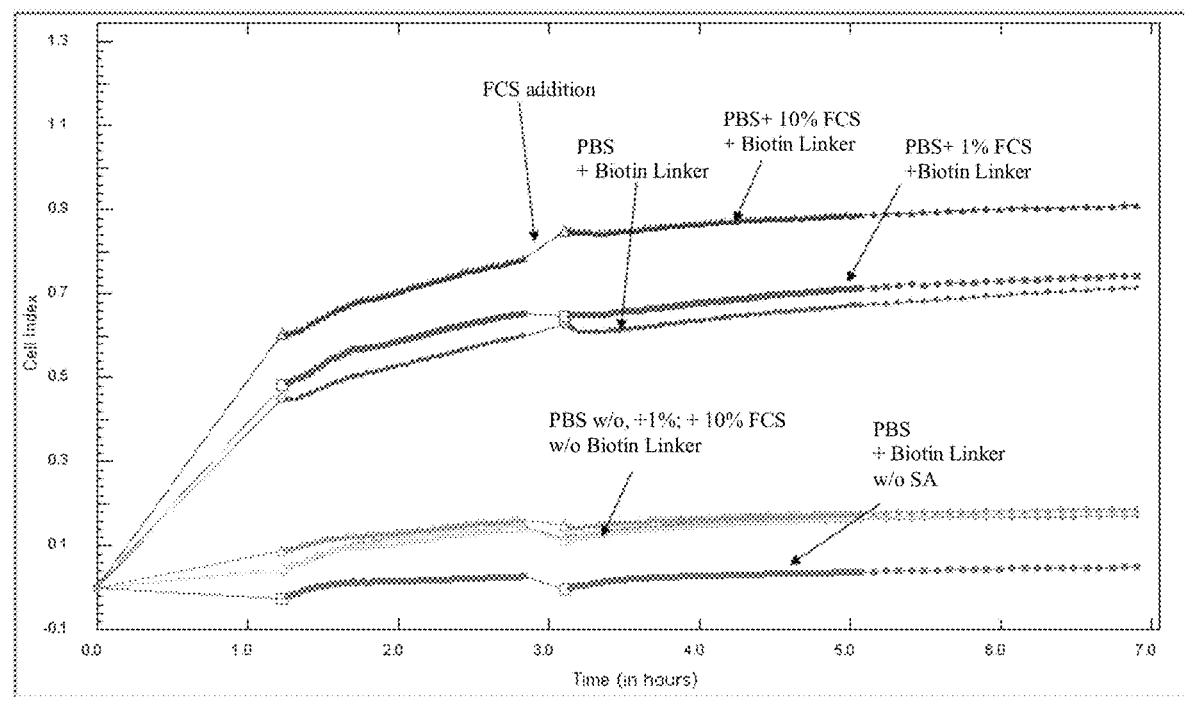
FIG. 8A: shows the results of the xCelligence experiments with Jurkat cells according to Example 3.
Figure 8B:
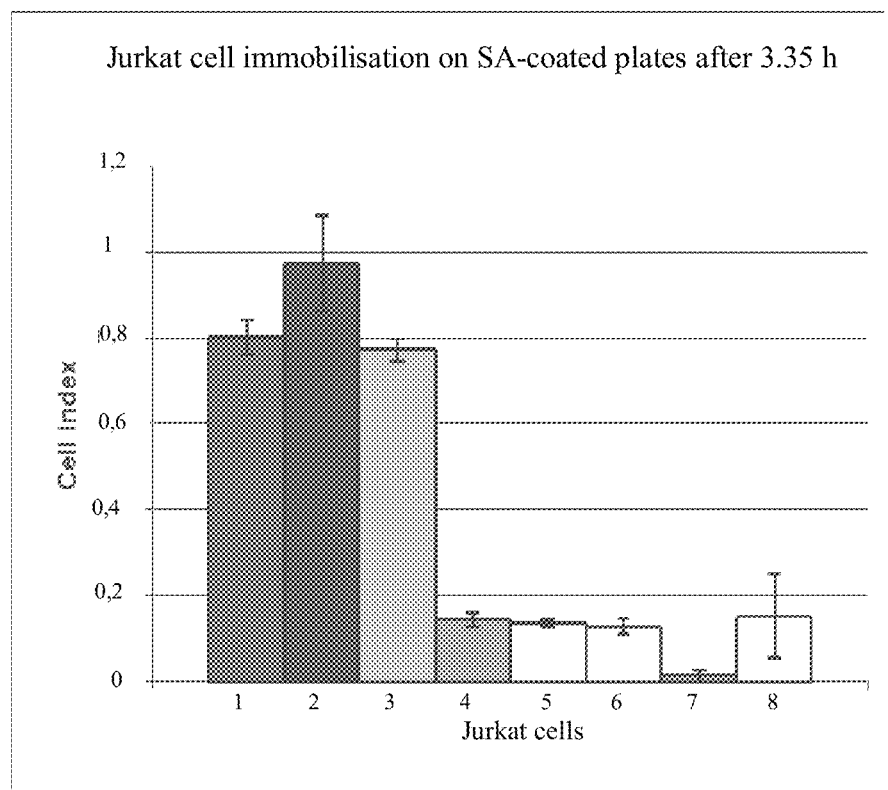
FIG. 8B: shows the results of the xCelligence experiments with Jurkat cells according to Example 3, specifically showing Jurkat cell immobilization on SA-coated plates after 3.35 hours. Column 1: PBS+ Biotin Linker; Column 2: PBS+10% FCS+ Biotin linker; Column 3: PBS+1% FCS+ Biotin linker; Column 4: PBS w/o Biotin linker; Column 5: PBS+10% FCS w/o Biotin linker; Column 6: PBS+1% FCS w/o Biotin linker; Column 7: PBS+ Biotin linker w/o SA; Column 8: PBS w/o Biotin linker w/o SA.
Figure 9A:
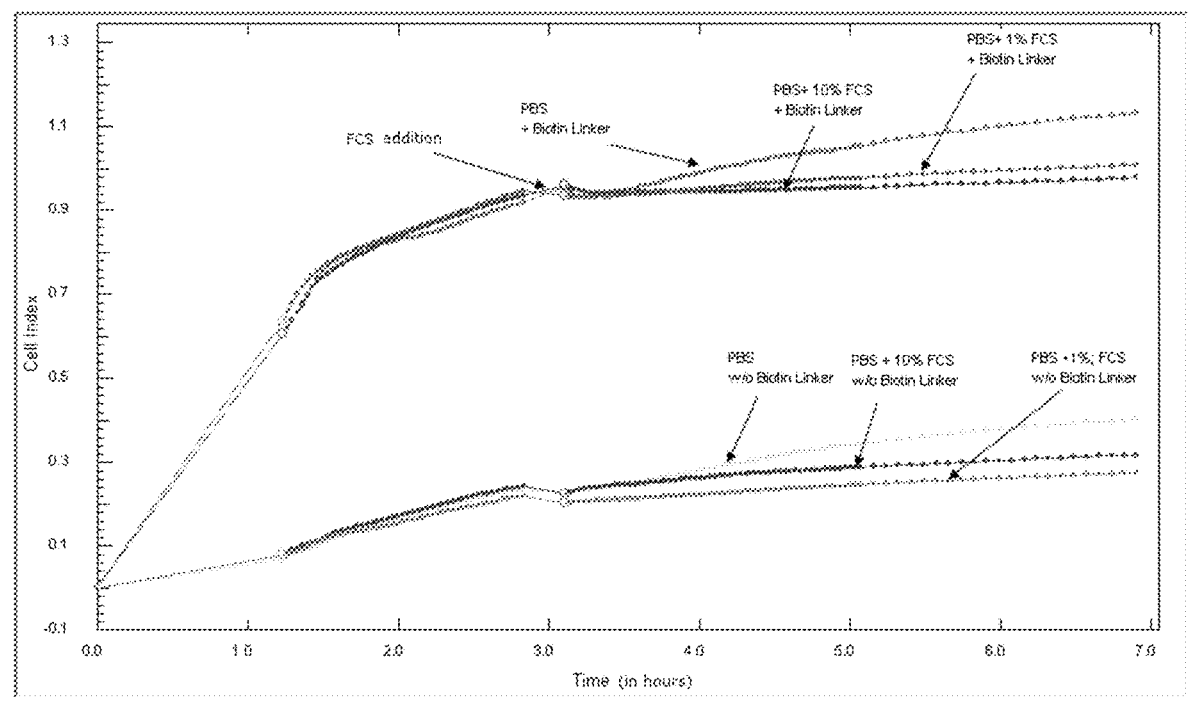
FIG. 9A: shows the results of the xCelligence experiments with WBC cells according to Example 3.
Figure 9B:
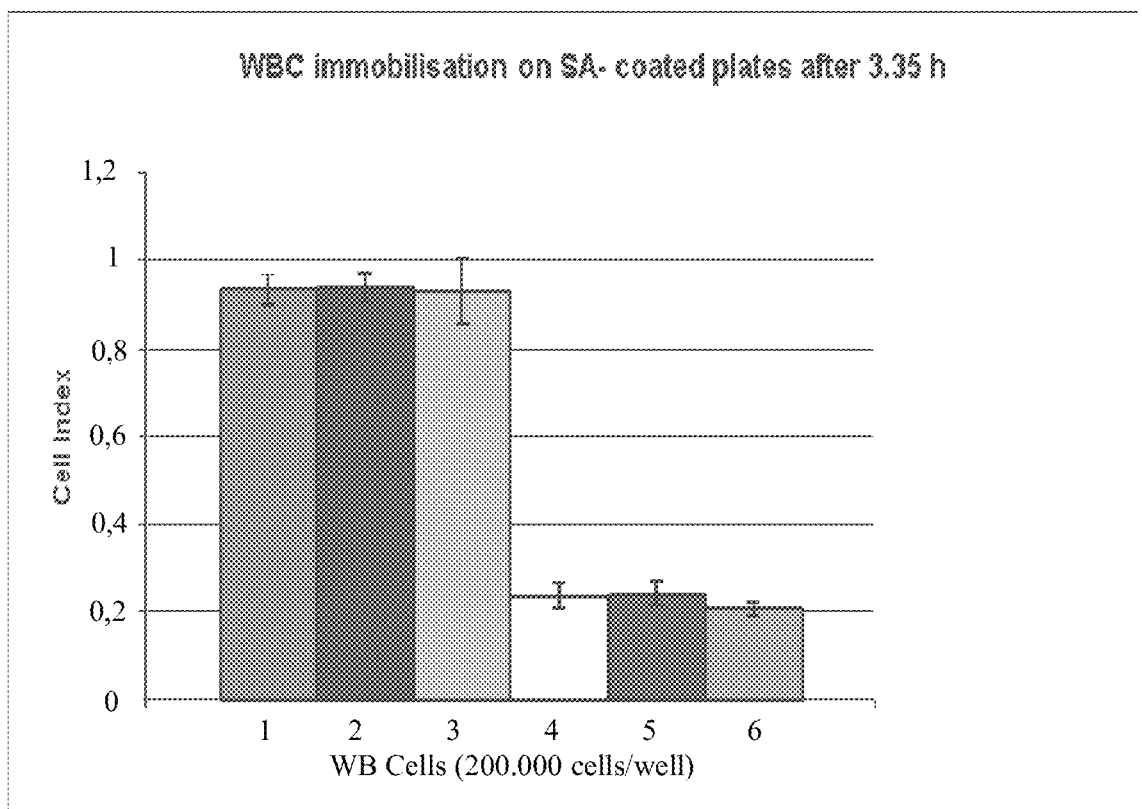
FIG. 9B: shows the results of the xCelligence experiments with WBC cells according to Example 3, specifically showing WBC immobilization onf SA-coated plates after 3.35 hours. Column 1: PBS+ Biotin Linker; Column 2: PBS+10% FCS+ Biotin linker; Column 3: PBS+1% FCS+ Biotin linker; Column 4: PBS w/o Biotin linker; Column 5: PBS+ 10% FCS w/o Biotin linker; Column 6: PBS+1% FCS w/o Biotin linker.
Figure 10:
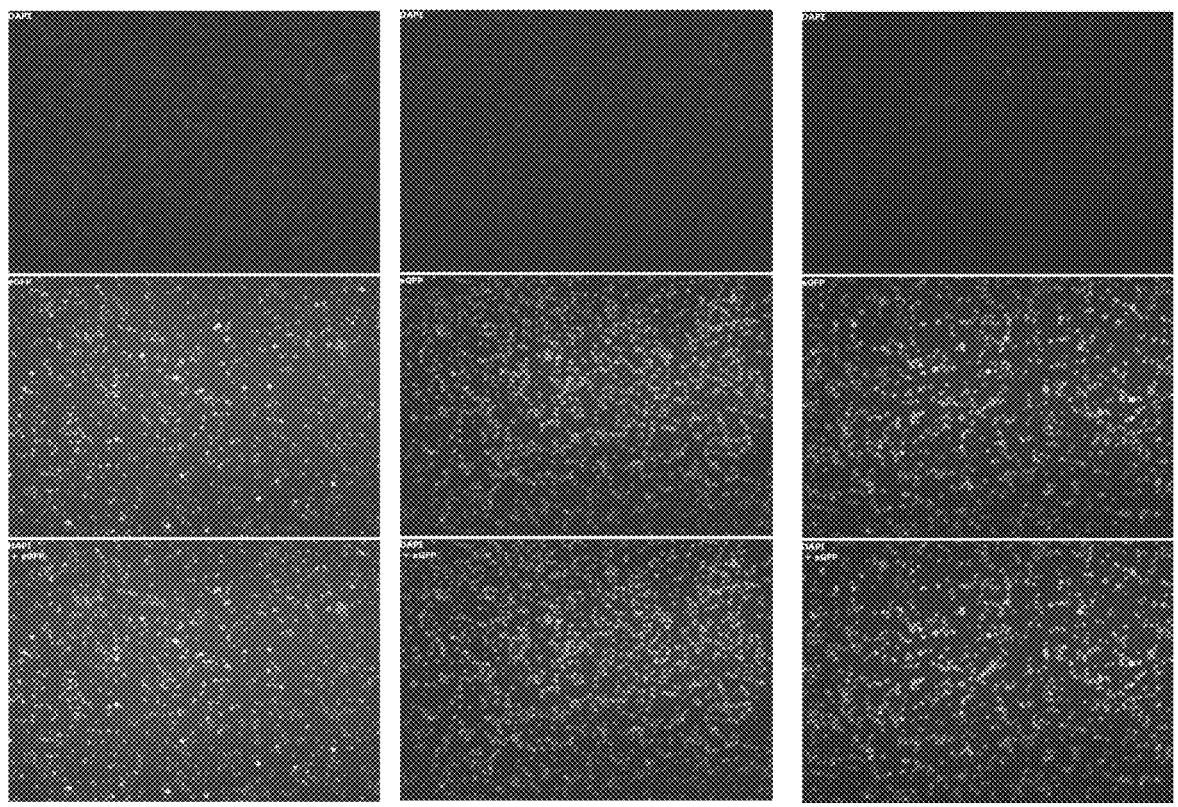
FIG. 10: shows the staining of immobilized cells, in accordance with Example 3. Left column: DA-MB468-antibody: K5/8. Middle column: MDA-MB468-antibody: EpCAM Miltenyi FITC. Right column: MDA-MB468-antibody: EGFR.
Figure 11:
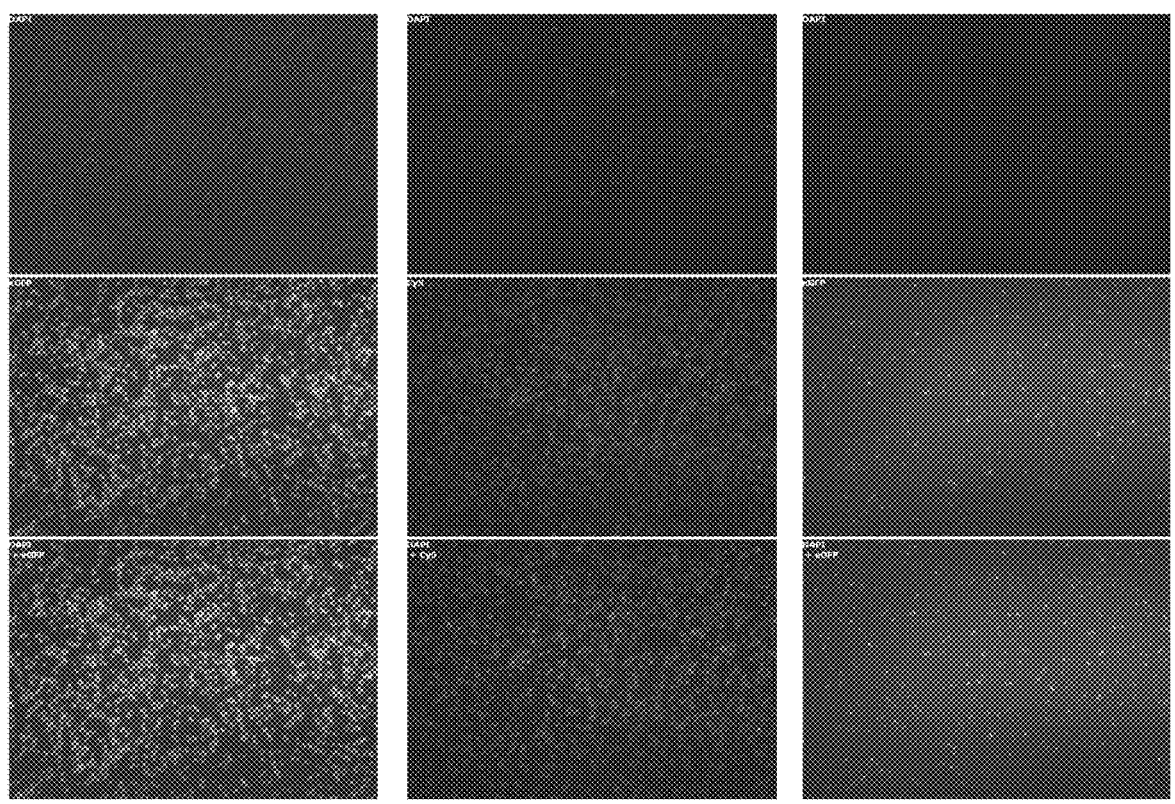
FIG. 11: shows the staining of immobilized cells, in accordance with Example 3. Left column: MDA-MB468-antibody: EpCAM Biolegend. Middle column: MDA-MB468-antibody: EpCAM Miltenys APC. Right column: WBCs-antibody: CD45 Biolegend.
Figure 13:
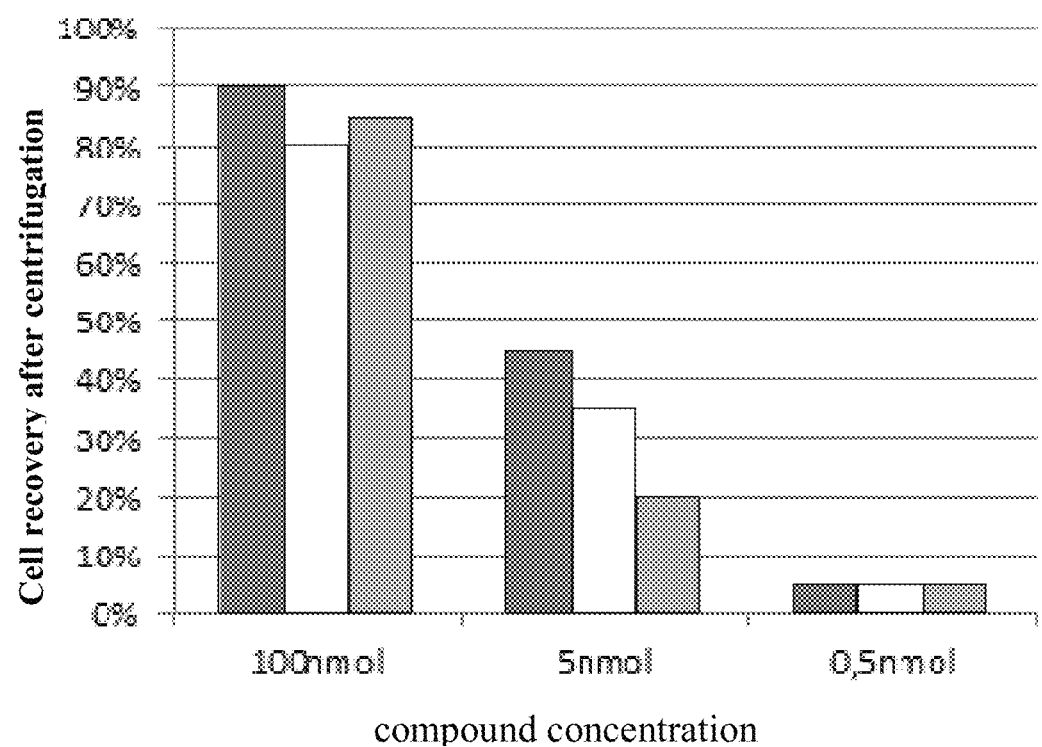
FIG. 13: shows WBC recovery rate after centrifugation and cell immobilization using different molecules. Molecule probes HH1749*, HH1750* and HH1755* (*Biotin-PEG-Lysin-(C18)2) show different performance concerning recovery rate after centrifugation: The higher the concentration of the molecule, the higher the cell recovery rate after centrifugation. Centrifugation characteristics: 10 min, 300× g.

PEG-based linkers, namely TEG-linkers were shown to be useful in the exemplary compounds useful in methods of the invention. An exemplary compound is 5'-CholesterylTEG-CholesterylTEG-(SpacerC18)7-Fluos-Biotin-TEG-K The compounds useful in methods of the invention as well as the intermediates thereof can be prepared by methods known to a skilled person. An exemplary synthesis of a compound useful in methods of the invention is shown in FIG. 6C. Also, intermediates used in the synthesis of compounds useful in methods of the invention are shown in FIG. 12. Further, the general concept of the syntheses is shortly described in Example 1 for the compounds. The compounds can be prepared on solid phase analogous to the phosphoramidite-based synthesis of nucleotides. The compounds may be synthesized by synthesis on a solid support like CPG as described in the Examples. In particular, the compounds may be synthesized by subsequent coupling steps under conditions known to a skilled person, and cleavage from the solid support (in the examples: CPG (controlled pore glass)). Also other solid supports such as macroporous polystyrene may be used for synthesis. The synthesis may be performed by retaining a protecting group or by cleaving of the protecting group. In particular, the compounds may be synthesized in either DMT on or DMT off modus, leaving the DMT molecule on the end of the molecule designated as 3' end, or by cleaving off the DMT group. The compounds are optionally further purified e.g. by dialysis.

The synthesis of Biotin-PEG-Lys-(C18)2 is described in detail in FIG. 6 C).

The other compounds useful in methods of the invention can be prepared in an analogous manner according to methods known in the art.

As explained above, the compounds employed in the methods of the invention may be contacted in step b) as a composition, e.g. as aqueous solution.

In one preferred embodiment, a composition comprising more than one compound described above may be used.

In a more preferred embodiment, the compound or salt thereof is in a composition comprising one or more compounds as described above.

Thus, in one embodiment, the present invention relates to a method of immobilizing a cell on a surface, the method comprising
a) providing composition comprising a compound or salt thereof comprising, preferably consisting of, one or more hydrophobic domains attached to a hydrophilic domain, wherein the one or more hydrophobic domains are covalently bound to said hydrophilic domain, and
wherein the one or more hydrophobic domains each comprise a linear lipid, a steroid or a hydrophobic vitamin, and wherein the hydrophilic domain comprises a polyethylene glycol (PEG) moiety, and
wherein the compound comprises a linking group;
b) contacting a cell with the composition comprising the compound under conditions allowing the interaction of the compound with the membrane of the cell, thereby immobilizing the linking group on the surface of the cell; and c) contacting the linking group immobilized on the cell with a surface capable of binding the functional domain, thereby immobilizing the cell on the surface.

In an even more preferred embodiment, the composition comprises at least three different compounds as described above, and wherein (i) the different compounds differ at least in their hydrophobic domains and (ii) the different compounds comprise a label moiety.

In an even more preferred embodiment, the composition comprises at least four, five, six, seven, eight, nine or ten different compounds.

The invention further relates to a composition comprising at least one compound useful in methods of the invention bound to at least one cell, preferably a viable cell. Such composition is useful for immobilization and optionally detection of the cell, respectively.

In one preferred embodiment, such composition further comprises a solid support, to which at least one compound useful in a method of the invention is bound via a linking group. In such embodiment, at least one cell is immobilized to a solid support via a compound useful in a method of the invention. In case the compound further contains a label moiety, localization, detection and quantification of the cell(s) is possible.

In another preferred embodiment, a composition comprising at least one compound useful in a method of the invention bound to at least one cell comprises an aqueous, buffered solution, wherein at least one cell to which at least one compound useful in a method of the invention is bound, is suspended. Such composition is suitable for adequately stabilizing the cells therein, e.g. during FACS or centrifugation e.g. prior an immobilization step, or after an immobilization step and subsequent detachment.

The compounds useful in a method of the invention are suitable for binding to any cells which contain a lipid bilayer. Preferably, the cells are eukaryotic cells, more preferably animal, even more preferably vertebrate cells, most preferably human cells.

In a preferred embodiment, the cell is a cell in suspension and/or wherein the cell is an animal or human cell, particularly a vertebrate cell, especially a mammalian cell. Even more preferably, the cell is a cell in suspension and is an animal or human cell, particularly a vertebrate cell, especially a mammalian cell.

For example, the cell is a white blood cell, a rare cell, a tumor cell or a mutated cell, more preferably a vertebrate or human white blood cell, rare cell, tumor cell or mutated cell.

In a further embodiment the present invention relates to a method of the invention wherein a composition comprising one or more compounds useful in a method of the invention are used.

It could be shown that some compositions comprising two or more different compounds useful in a method of the invention of the invention are in particular useful for cell-type-independent immobilization and labeling.

Therefore, in another embodiment, the present invention relates a method of the invention wherein a composition comprising at least three different compounds useful in a method of the invention is used, wherein the different compounds differ at least in their hydrophobic domains and wherein the different compounds comprise a label moiety.

By using a variety of compounds useful in a method of the invention of which at least two differ at least in their hydrophobic domain(s), a composition can be obtained which binds all cell types, thereby providing a cell-type independent immobilization.

In an even more preferred embodiment, the composition thus comprises at least four, five, six, seven, eight, nine or ten different compounds useful in a method of the invention. In an even more preferred embodiment, two, three, four, five, six, seven, eight, nine, ten or all compounds of such composition differ at least in their hydrophobic domains.

Preferred hydrophobic domains which are suitable are those as defined above.

In a more preferred embodiment, a hydrophobic domain of at least one compound comprises, preferably consists of, a saturated fatty acid, especially myristic acid, stearic acid or behenic acid, particularly myristic acid, and/or a hydrophobic domain of at least one compound comprises, preferably consists of, a steroid, in particular cholesterol, or a hydrophobic vitamin, in particular α-tocopherol.

In preferred embodiment, the present invention relates a method of the invention wherein an aqueous solution comprising one or more compounds useful in a method of the invention are used.

The aqueous solution used in a method of the invention is preferably buffered. For example a solution may be a phosphate buffered saline solution (PBS), Tris, and/or Hepes-buffered solution.

The pH of the solution for use in a method of the invention is preferably about 5.5 to 8.5, more preferably 6.5 to 7.5.

In yet further embodiment, the present invention relates to the use of a kit comprising at least one compound or composition as disclosed above for immobilizing cells.

The kit may further comprise two or more compounds for use in methods of the invention stored separately, e.g. in a vessel or syringe. They may be stored in dry form, e.g. freeze-dried or dried, or as solution, or in frozen form, e.g. as frozen solution.

In one of the embodiment, the method of the invention can be used for immobilization, and optionally detection and/or characterization of rare cells, preferably for one rare cell characterization.

Therefore, in another embodiment, the present invention relates to a method of immobilizing a population of cells comprising a cell of interest on a surface, the method comprising a) providing a compound or salt thereof comprising, preferably consisting of, one or more hydrophobic domains attached to a hydrophilic domain, wherein the one or more hydrophobic domains are covalently bound to said hydrophilic domain, and
   wherein the one or more hydrophobic domains each comprise a linear lipid, a steroid or a hydrophobic vitamin, and wherein the hydrophilic domain comprises a polyethylene glycol (PEG) moiety, and
   wherein the compound comprises a linking group;

b) contacting the population of cells with the compound under conditions allowing the interaction of the compound with the membrane of the cells, thereby immobilizing the linking group on the surface of the cells;

c) contacting the linking group immobilized on the cell with a surface capable of binding the linking group, thereby immobilizing the cells on the surface; and d) optionally detecting the cell of interest immobilized on the surface.

A population of cells is a composition comprising at least two cells, which contains or is suspected to contain at least two different cells. Such different cells may be e.g. T cells and B cells, different T cell subsets, or tumor cells and non-tumor cells, or endothelial cells and epithelial cells, respectively.

The "membrane of the cell" according to the invention is understood as cytoplasmic membrane.

For this method of the invention, the same embodiments apply as for the method for immobilizing a cell on a surface of the invention described above. Therefore, also a composition comprising suitable compounds may be employed as described above.

In a particularly preferred embodiment, the cell of interest is a white blood cell, particularly a rare cell such as a circulating tumor cell, endothelial cell or epithelial cell.

Even more preferably, the cell is a cell in suspension and/or the cell is an animal or human cell, particularly a vertebrate cell, especially a mammalian cell.

The detecting the cell of interest immobilized on the surface can be performed by using a specific detection agent for such cell of interest, e.g. an antibody or antigen-binding fragment thereof recognizing a specific cell surface marker, or a plurality of antibodies or antigen-binding fragments thereof recognizing a plurality of specific cell surface marker, as e.g. for detecting specific T cell subset populations, or recognizing specific tumor marker(s) for detecting a specific tumor cell type. As described above, and as known to a skilled person, such detection agent like an antibody or antigen-binding fragment thereof may then be detected directly or indirectly. In case of direct detection, the detection agent itself is labeled with a directly detectable label, such as a fluorescent dye. Alternatively, an indirectly detectable label can be used, e.g. a secondary antibody may be detected with a label moiety, such as a fluorescent moiety. Fluorescence may then be detected.

The detectable label for detecting the cell of interest is preferably different from the label moiety of a compounds used in steps a) and b) of the invention, in order to allow for specific detection of the cell of interest. In case fluorescent dyes are used, the respective dyes preferably exhibit distinct excitation and/or emission spectra.

In such embodiment of immobilizing cells of interest, e.g. nucleated cells isolated from whole blood can be immobilized on a defined support or surface by performing a method of the invention, in particular on an array, more preferably microarray or nanoarray. Rare cells within this population of nucleated cells, for example within a population of white blood cells (WBCs) e.g. circulating tumor cells, endothelial cells, or epithelial cells, can be quantitatively bound to this surface or support and identified via an antibody or specific binding molecule against an antigen or biochemical property specific for the rare cell population.

This enables the exact localization and re-localization for further characterization steps if required.

Therefore, in a preferred embodiment of the invention, step d) detecting the cell of interest immobilized on the surface is performed.

In a further embodiment of the present invention a compound useful in a method of the invention further comprising a label moiety is employed. This allows detection of the cell population as such, and allows obtaining information about the cells of interest in comparison to the population of cells.

Therefore, the present invention also relates to the use of a method of the invention for one rare cell characterization.

Therefore, in a further embodiment of the present invention, one rare cell characterization is performed as further step e), e.g. by detection of cell surface markers.

In a further embodiment, the method of the invention can be used for immobilization of suspension cells, in particular for screening purposes like for antibody screening. For example, immobilized cells presenting an antibody or antigen-binding fragment on the surface may be screened for binding to an antigen by methods known in the art.

Screening of antibodies or antigen-binding fragments thereof on culture cell lines is a general application in antibody development. One application comprises the binding of the antibody to a specific receptor molecule on the cell surface. Using a secondary antibody (sandwich effect) binding characteristics of the first antibody can be investigated. Using suspension cells it is difficult to perform such experiments. The methods of the invention allow the careful immobilization of suspension cells without loosing any physiological cell properties and can be therefore used to perform such screening assays.

Also, suspension cells can be immobilized for functional cell assays using the methods of the invention. Assays studying cellular function in vitro or in vivo are of importance: Functional cellular assays are generally used in pharmaceutical, agrochemical and biotechnological research and development to investigate small molecule compounds or biologicals or to identify classes of small molecules in high throughput screening. Some functional assays are based on surface-dependent assays and are therefore generally performed with adherent cells. The methods of the invention can be performed for immobilization of suspension cells to apply such functional assays as subsequent step.

Therefore, in a further embodiment of the present invention, the method further comprises a step e) screening of the immobilized cells, e.g. antibody screening of the immobilized cells.

In a yet further embodiment of the present invention, the method further comprises a step e) performing a functional cellular assay with the immobilized cells.

Therefore, the present invention also relates to the use of a method of the invention for immobilization of suspension cells, preferably for screening, even more preferably for screening with antibodies or antigen-binding antibody fragments or binding molecules of other formats.

Therefore, the present invention also relates to the use of a method of the invention, for performing functional cellular assays.

In one preferred embodiment, the methods of the invention are in vitro methods.

Moreover, methods of the invention can be followed by a subsequent step of detachment of the cells. For example, the method of the invention can be performed for immobilizing living cells to a solid support or surface, followed by detachment off the support or surface and implantation into mouse models. These kinds of functional assays are of major importance, e.g. for studying the tumor-inducing potential of circulating abnormal cells.

In this embodiment, the detachment can be performed after step c): contacting the linking group immobilized on the cell with a surface capable of binding the linking group, thereby immobilizing the cells on the surface; or after step d): detecting the cell of interest immobilized on the surface, of the invention, preferably after step d): detecting the cell of interest immobilized on the surface, of the invention.

In a further preferred embodiment, a screening step and/or rare cell characterization step and/or functional cellular assay step is performed before detachment of the cells.

Therefore, in a further embodiment of the present invention, the method further comprises a step relating to subsequent detachment of the immobilized cells.

The methods of the invention can be performed as a lab on a chip: To investigate cell morphology or cell function of few cells like 2 to 50 cells, or single cells, a support or surface can be selectively and systematically spotted with a compound useful in a method of the invention. This spotting allows a targeted immobilization of few cells or single cells on such spot. This allows molecular analysis directly on the support or surface (chip).

Therefore, in one embodiment, 2, 3, 4, or more methods of the invention are performed in parallel, in particular on a solid substrate, like a chip. The chip may be an array, in particular microarray or nanoarray. For example 50, 1000 or 10000 immobilization methods are performed in parallel.

Such solid substrate may be a particle like a nanoparticle, in particular magnetic nanoparticle, a column, or a flat substrate, an array or a well plate, in particular oligo- or multi-well plate. In a preferred embodiment, the array is a microarray or nanoarray.

The compounds used in methods of the invention are also useful for cell stabilization, e.g. during conditions representing shear stress.

Therefore, the present invention also relates to the use of a method of the invention for stabilizing at least one cell during immobilization or during cultivation prior to step a) of a method of the invention.

The compounds useful in methods of the invention are moreover useful for cell stabilization in biotechnology, for example in large scale animal cell cultivation: it has been published that shear sensitivity of mammalian cells can be a relevant problem which can complicate the development of large scale animal cell cultivation. The compounds reduce these problems.

The compounds useful in methods of the invention are moreover useful for cell stabilization in flow cytometry and/or fluorescence activated cell sorting:

Flow cytometry is a very commonly used method to separate specific cell population. Within this process, cells are exposed to high shear stresses dependent on the flow speed. The compounds useful in methods of the invention reduce this shear stress.

The compounds useful in methods of the invention are moreover useful for cell stabilization in bead-based cell separation processes:

Cell populations with a distinct phenotype can be separated by specific antibodies coupled to magnetic beads. Within this process cells are exposed to high shear stresses dependent on the bead size. The compounds useful in methods of the invention reduce this shear stress.

Regarding the antibodies and antigen-binding antibody fragments, skilled person is aware of such molecules: Naturally occurring antibodies are globular plasma proteins (~150 kDa (http://en.wikipedia.org/wiki/Dalton_unit)) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM. In the present invention, examples of suitable formats include the format of naturally occurring antibodies including antibody isotypes known as IgA, IgD, IgE, IgG and IgM.

In addition to naturally occurring antibodies, artificial antibody formats including antibody fragments have been developed. Some of them are described in the following.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs).

Because CDRs from both VH and VL domains contribute to the antigen-binding site, it is the combination of the heavy and the light chains, and not either alone, that determines the final antigen specificity.

Accordingly, the term "antibody", as used herein, means any polypeptide which has structural similarity to a naturally occurring antibody and is capable of specific binding to the respective target, wherein the binding specificity is determined by the CDRs. Hence, "antibody" is intended to relate to an immunoglobulin-derived structure with binding to the respective target including, but not limited to, a full length or whole antibody, an antigen binding fragment (a fragment derived, physically or conceptually, from an antibody structure), a derivative of any of the foregoing, a chimeric molecule, a fusion of any of the foregoing with another polypeptide, or any alternative structure/composition which selectively binds to the respective target. The antibody or functionally active parts thereof may be any polypeptide which comprises at least one antigen binding fragment. Antigen binding fragments consist of at least the variable domain of the heavy chain and the variable domain of the light chain, arranged in a manner that both domains together are able to bind to the specific antigen.

"Full length" or "complete" antibodies refer to proteins that comprise two heavy (H) and two light (L) chains inter-connected by disulfide bonds which comprise: (1) in terms of the heavy chains, a variable region and a heavy chain constant region which comprises three domains, CH1, CH2 and CH3; and (2) in terms of the light chains, a light chain variable region and a light chain constant region which comprises one domain, CL.

"Antigen-binding antibody fragments" or "Antigen-binding fragments thereof" also contain at least one antigen binding fragment as defined above, and exhibit essentially the same function and binding specificity as the complete antibody of which the functionally active part (or fragment) is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Variable domains (Fvs) are the smallest fragments with an intact antigen-binding domain consisting of one VL and one VH. Such fragments, with only the binding domains, can be generated by enzymatic approaches or expression of the relevant gene fragments, e.g. in bacterial and eukaryotic cells. Different approaches can be used, e.g. either the Fv fragment alone or 'Fab'-fragments comprising one of the upper arms of the "Y" that includes the Fv plus the first constant domains. These fragments are usually stabilized by introducing a polypeptide link between the two chains which results in the production of a single chain Fv (scFv). Alternatively, disulfide-linked Fv (dsFv) fragments may be used. The binding domains of fragments can be combined with any constant domain in order to produce full length antibodies or can be fused with other proteins and polypeptides.

A recombinant antibody fragment is the single-chain Fv (scFv) fragment. Dissociation of scFvs results in monomeric scFvs, which can be complexed into dimers (diabodies), trimers (triabodies) or larger aggregates such as TandAbs and Flexibodies.

Antibodies with two binding domains can be created either through the binding of two scFv with a simple polypeptide link (scFv)2 or through the dimerization of two monomers (diabodies). The simplest designs are diabodies that have two functional antigen-binding domains that can be either the same, similar (bivalent diabodies) or have specificity for distinct antigens (bispecific diabodies).

Also, antibody formats comprising four variable domains of heavy chains and four variable domains of light chains have been developed. Examples of these include tetravalent bispecific antibodies (TandAbs and Flexibodies, Affimed Therapeutics AG, Heidelberg. Germany). Flexibodies are a combination of scFv with a diabody multimer motif resulting in a multivalent molecule with a high degree of flexibility for joining two molecules which are quite distant from each other on the cell surface. If more than two functional antigen-binding domains are present and if they have specificity for distinct antigens, the antibody is multi-specific.

In summary, specific immunoglobulin types which represent antibodies or antigen-binding fragments thereof include but are not limited to the following antibody: a Fab (monovalent fragment with variable light (VL), variable heavy (VH), constant light (CL) and constant heavy 1 (CHI) domains), a F(ab')2 (bivalent fragment comprising two Fab fragments linked by a disulfide bridge or alternative at the hinge region), a Fv (VL and VH domains), a scFv (a single chain Fv where VL and VH are joined by a linker, e.g., a peptide linker), a bispecific antibody molecule (an antibody molecule with specificity as described herein linked to a second functional moiety having a different binding specificity than the antibody, including, without limitation, another peptide or protein such as an antibody, or receptor ligand), a bispecific single chain Fv dimer, a diabody, a triabody, a tetrabody, a minibody (a scFv joined to a $CH_3$).

The antibody may be a monoclonal antibody, a chimeric antibody or a humanised antibody.

A tag is a peptide motif used for recognition in biotechnology. A well-known tag is the His-tag (6xHistidine) which can be bound to a $Ni^{2+}$-column.

In case a nucleic acid or nucleic acid analogue/complementary nucleic acid is used as binding pair, any nucleic acid sequence and its complementary sequence may be used.

The lectins are carbohydrate-binding proteins that are highly specific for sugar moieties. As a suitable lectin, Concanavalin A may be used which binds to α-D-mannosyl and α-D-glucosyl residues, branched α-mannosidic structures (high α-mannose type, or hybrid type and biantennary complex type N-Glycans.

As receptor/ligand binding pair, e.g. steroid hormone receptor/steroid hormone may be used. For example, estrogen may be used as steroid, and a receptor thereof as respective binding partner.

Example 1: Synthesis of Compounds Useful in Methods of the Invention

The following compounds useful in methods of the invention were synthesized:

| Internal No. | Scale | chemical structure (modular) | Yield |
|---|---|---|---|
| BMO 29.891131 | 10 µMol Scale | 5'-alphaTocopherolTEG-PEG2000-Fluos-3' | 58 pMol/µL-234 nMol |
| | | DMTrON-Synthesis/all 20 min. Coupling/Standard-CPG-Cleavage/DMTrOFF/Dialysis/no Purification/Crude product/Fluos-Conc. | |
| BMO 29.891132 | 10 µMol Scale | 5'-Cholesteryl-TEG-PEG2000-Fluos-3' | 61 pMol/µL-216 nMol |
| | | DMTrON-Synthesis/all 20 min. Coupling/Standard-CPG-Cleavage/DMTrOFF/Dialysis/no Purification/Crude product/Fluos-Conc. | |
| BMO 29.891133 | 10 µMol Scale | 5'-CholesterylTEG-CholesterylTEG-PEG2000-Fluos-3' | 43 pMol/µL-153 nMol |
| | | DMTrON-Synthesis/all 20 min. Coupling/Standard-CPG-Cleavage/DMTrOFF/Dialysis/no Purification/Crude product/Fluos-Conc. | |
| BMO 29.891137 | 10 µMol Scale | 5'-CholesterylTEG-CholesterylTEG-PEG2000-BiotinTEG-3' | 111 pMol/µL-200 nMol |
| | | DMTrOFF-Synthesis/all 20 min. Coupling/Standard-CPG-Cleavage/Dialysis/no Purification/Crude product/Conc. estimated | |
| BMO 29.891180 | 10 µMol Scale | 5'-CholesterylTEG-CholesterylTEG-PEG2000-Fluos-BiotinTEG-3' | 3577 pMol/µL-6440 nMol |
| | | DMTrOFF-Synthesis/all 20 min. Coupling/Standard-CPG-Cleavage/Dialysis/no Purification/Crude product/Fluos-Conc. | |
| BMO 29.891194_Ch01 | 1 µMol Scale | 5'-Myristic acid-Myristic acid-PEG2000-Fluos-BiotinTEG-3' | 10 pMol/µL-12 nMol |
| | | DMTrON-Synthesis/Coupling: 1 + 2 = 10 min – 3 = 2 × 8 min – 4 + 5 = 10 min/Standard-CPG-Cleavage/C18-Purification/DMTrOFF/Dialysis/ F30-39-TEA+/Fluos-Conc. | |
| BMO 29.891194_Ch02 | 1 µMol Scale | 5'-Myristic acid-Myristic acid-PEG2000-Fluos-BiotinTEG-3 | 22 pMol/µL-24 nMol |
| | | DMTrON-Synthesis/Coupling: 1 + 2 = 10 min – 3 = 2 × 8 min – 4 + 5 = 15 min/Standard-CPG-Cleavage/C18-Purification/ F89-98-TEA+/evaporate/DMTrOFF/Fluos-Conc. | |
| BMO 29.891194_Ch03 | 1 µMol Scale | 5'-Myristic acid-Myristic acid-PEG2000-Fluos-BiotinTEG-3' | 11 pMol/µL-11 nMol |
| | | DMTrON-Synthesis/all 20 min. Coupling/Standard-CPG-Cleavage/C18-Purification/F69-79-TEA+/evaporate/DMTrOFF/Fluos-Conc. | |
| BMO 29.891197 | 1 µMol Scale | 5'-Myristic acid-SpacerC9-Myristic acid-PEG2000-Fluos-BiotinTEG-3' | 0.5 pMol/µL-0.7 nMol |
| | | DMTrON-Synthesis/all 20 min. Coupling/Standard-CPG-Cleavage/C18-Purification/F67-72-TEA+/evaporate/DMTrOFF/Fluos-Conc. | |
| BMO 29.891213_Ch01 | 10 µMol Scale | 5'-Myristic acid-Myristic acid-SpacerC18-Fluos-BiotinTEG-3' | 538 pMol/µL-808 nMol |
| | | DMTrON-Synthesis/all 20 min. Coupling/Standard-CPG-Cleavage/T1-C18-Purification/T1 = F40-44-TEA+/evaporate/Fluos-Conc. | |
| BMO 29.891213_Ch02 | | 5'-Myristic acid-Myristic acid-SpacerC18-Fluos-BiotinTEG-3' | 613 pMol/µL-919 nMol |
| | | T2-C18-Purification/T2 = F73-99-TEA+/evaporate/DMTrOFF/Fluos-Conc. | |
| BMO 29.891214 | 1 µMol Scale | 5'-Myristic acid-Myristic acid-(SpacerC18)7-Fluos-BiotinTEG-3' | 100 pMol/µL-100 nMol |
| | | DMTrON-Synthesis/all 10 min. Coupling/Standard-CPG-Cleavage/C18-Purification/F49-53-TEA+/evaporate/DMTrOFF/Fluos-Conc. | |
| BMO 29.891218 | 1 µMol Scale | 5'-Myristic acid-SpacerC9-Myristic acid-(SpacerC18)7-Fluos-BiotinTEG-3' | 40 pMol/µL-44 nMol |
| | | DMTrON-Synthesis/Coupling: 1 + 2 = 20 min – 3 – 9 = 5 min – 10 – 12 = 20 min/Standard-CPG-Cleavage/C18-Purification/ F30-35-TEA+/evaporate/DMTrOFF/Fluos-Conc. | |
| BMO 29.891219 | 1 µMol Scale | 5'-Myristic acid-SpacerC12-Myristic acid-(SpacerC18)7-Fluos-BiotinTEG-3 | 15 pMol/µL-22 nMol |
| | | DMTrON-Synthesis/Coupling: 1 + 2 = 20 min – 3 – 9 = 5 min – 10 – 12 = 20 min/Standard-CPG-Cleavage/C18-Purification/ F28-32-TEA+/evaporate/DMTrOFF/Fluos-Conc. | |

-continued

| Internal No. | Scale | chemical structure (modular) | Yield |
|---|---|---|---|
| BMO 29.891220 | 1 μMol Scale | 5'-Myristic acid-SpacerC18-Myristic acid-(SpacerC18)7-Fluos-BiotinTEG-3' | 56 pMol/μL-79 nMol |
| | | DMTrON-Synthesis/Coupling: 1 + 2 = 20 min – 3 – 9 = 5 min – 10 – 12 = 20 min/Standard-CPG-Cleavage/C18-Purification/ F34-38-TEA+/evaporate/DMTrOFF/Fluos-Conc. | |
| BMO 29.891221 | 1 μMol Scale | 5'-Myristic acid-Myristic acid-Myristic acid-(SpacerC18)7-Fluos-BiotinTEG-3' | 38 pMol/pL-42 nMol |
| | | DMTrON-Synthesis/Coupling: 1 + 2 = 20 min – 3 – 9 = 5 min – 10 – 12 = 20 min/Standard-CPG-Cleavage/C18-Purification/ F32-41-TEA+/evaporate/DMTrOFF/Fluos-Conc. | |
| BMO 29.891222_Ch03 | 1 μMol Scale | 5'-CholesterylTEG-CholesterylTEG-(SpacerC18)7-Fluos-BiotinTEG-3' | 12 pMol/μL-14 nMol |
| | | DMTrON-Synthesis/Coupling: 1 + 2 = 2 × 10 min – 3 – 9 = 5 min – 10 – 12 = 2 × 10 min/Standard-CPG-Cleavage/C8-Purification/ F69-73-TEA+/evaporate/DMTrOFF/Fluos-Conc. | |
| BMO 29.891222_Ch04 | 1 μMol Scale | 5'-CholesterylTEG-CholesterylTEG-(SpacerC18)7-Fluos-BiotinTEG-3' | 6 pMol/μL-7 nMol |
| | | DMTrON-Synthesis/Coupling: 1 + 2 = 2 × 15 min – 3 – 9 = 5 min – 10 – 12 = 2 × 15 min/Standard-CPG-Cleavage/C4-Purification/ F10-13-TEA+/evaporate/DMTrOFF/Fluos-Conc. | |
| BMO 29.891222_Ch05 | 1 μMol Scale | 5'-CholesterylTEG-CholesterylTEG-(SpacerC18)7-Fluos-BiotinTEG-3' | 13 pMol/μL-17 nMol |
| | | DMTrOFF-Synthesis/Coupling: 1 + 2 = 2 × 15 min – 3 – 9 = 5 min – 10 – 12 = 2 × 15 min/Standard-CPG-Cleavage/C4-Purification/ F60-64-TEA+/evaporate/Fluos-Conc. | |
| BMO 29.891224 | 1 μMol Scale | 5'-CholesterylTEG-SpacerC12-CholesterylTEG-(SpacerC18)7-Fluos-BiotinTEG-3 | 74 pMol/μL-81 nMol |
| | | DMTrON-Synthesis/Coupling: 1 + 2 = 20 min – 3 – 9 = 5 min – 10 – 12 = 20 min/Standard-CPG-Cleavage/C18-Purification/ F26-33-TEA+/evaporate/DMTrOFF/Fluos-Conc. | |
| BMO 29.891225 | 1 μMol Scale | 5'-CholesterylTEG-SpacerC18-CholesterylTEG-(SpacerC18)7-Fluos-BiotinTEG-3' | 5 pMol/μL-6 nMol |
| | | DMTrON-Synthesis/Coupling: 1 + 2 = 20 min – 3 – 9 = 5 min – 10 – 12 = 20 min/Standard-CPG-Cleavage/C18-Purification/ F14-19-TEA+/evaporate/DMTrOFF/Fluos-Conc. | |
| BMO 29.891227 | 1 μMol Scale | 5'-Myristic acid-CholesterylTEG-(SpacerC18)7-Fluos-BiotinTEG-3' | 20 pMol/μL-21 nMol |
| | | DMTrON-Synthesis/Coupling: 1 + 2 = 20 min – 3 – 9 = 5 min – 10 – 12 = 20 min/Standard-CPG-Cleavage/C18-Purification/ F34-40-TEA+/evaporate/DMTrOFF/Fluos-Conc. | |
| BMO 29.891228_Ch02 | 1 μMol Scale | 5'-CholesterylTEG-Myristic acid-(SpacerC18)7-Fluos-BiotinTEG-3' | 9 pMol/μL-11 nMol |
| | | DMTrON-Synthesis/Coupling: 1 + 2 = 20 min – 3 – 9 = 5 min – 10 – 12 = 20 min/Standard-CPG-Cleavage/C18-Purification/ F28-31-TEA+/evaporate/DMTrOFF/Fluos-Conc. | |
| BMO 29.891234_Ch03 | 10 μMol Scale | 5'-CholesterylTEG-CholesterylTEG-(SpacerC18)7-dT(Determ. of concentration)-BiotinTEG-3' | 239 pMol/μL-358 nMol |
| | | DMTrOFF-Synthesis-1000A-Universal-CPG/Coupling: 1 = 20 min – 3 – 8 = 5 min – 9 – 11 = 20 min/CPG-Cleavage = NH3-Isoprop/C8-Purification/F65-70-TEA+/evaporate/260 nm Conc. | |
| BMO 29.891234_Ch04 | 10 μMol Scale | 5'-CholesterylTEG-CholesterylTEG-(SpacerC18)7-dT(Determ. of concentration)-BiotinTEG-3 | 204 pMol/μL-307 nMol |
| | | DMTrOFF-Synthesis-Universal-PS/Coupling: 1 = 20 min – 3 – 8 = 5 min – 9 – 11 = 20 min/CPG-Cleavage = NH3-Isoprop/C8-Purification/ F83-88-TEA+/evaporate/260 nm Conc. | |
| BMO 29.891234_Ch07 | 10 μMol Scale | 5'-CholesterylTEG-CholesterylTEG-(SpacerC18)9bis10-dT(Determ. of concentration)-BiotinTEG-3' | 277 pMol/μL-415 nMol |
| | | DMTrOFF-Synthesis-Universal-PS + Hyazinthactivator/SpacerC18 = 0.2M/Coupling: 1 + 2 = 3 min-3 = 2 × 5 min – 4 – 11 = 3 min/ CPG-Cleavage = NH3-Isoprop/C8-Purification/F55-59-Na+/Vivaspin 2000/260 nm Conc. | |
| BMO 29.891234_Ch08 | 10 μMol Scale | 5'-CholesterylTEG-CholesterylTEG-(SpacerC18)9bis10-dT(Determ. of concentration)-BiotinTEG-3' | 306 pMol/μL-460 nMol |
| | | DMTrOFF-Synthesis-Universal-PS + Hyazinthactivator/SpacerC18 = 0.2M/Coupling: 1 + 2 = 3 min-3 = 2 × 5 min – 4 – 11 = 3 min/ CPG-Cleavage = NH3-Isoprop/C8-Purification/F37-41-Na+/Vivaspin 2000/260 nm Conc. | |
| BMO 29.891234_Ch09 | 10 μMol Scale | 5'-CholesterylTEG-CholesterylTEG-(SpacerC18)7-SpacerC3-dT(Determ. of concentration)-BiotinTEG-3' | see below |
| | | DMTrOFF-Synthesis-1000A-Universal-CPG + Hyazinthactivator/SpacerC18 = 0.2M/Coupling: 1 + 2 = 3 min-3 + 4 = 2 × 10 min – 5 – 10 = 10 min – 11 + 12 = 3 min/CPG-Cleavage = NH3-Isoprop/crude und C8-Purification/F = see below/Vivaspin 2000/260 nm Conc. | |
| | T1_crude | | 1'356 pMol/μL-2'033 nMol |
| | T2_crude_Na | | 1'165 pMol/μL-1'747 nMol |
| | T3_F38-40 | | 53 pMol/μL-80 nMol |
| | T4_F38-40_Na | | 51 pMol/μL-77 nMol |
| BMO 29.891236_Ch10 | 10 μMol Scale | 5'-CholesterylTEG-CholesterylTEG-(SpacerC18)7-SpacerC3-dT(Determ. of concentration)-BiotinTEG-3' | see below |
| | | DMTrOFF-Synthesis-1000A-Universal-CPG + Hyazinthactivator/SpacerC18 = 0.2M/Coupling: 1 + 2 = 3 min – 3 + 4 = 2 × 10 min – 5 – 10 = 10 min – 11 + 12 = 3 min/CPG-Cleavage = NH3-Isoprop/CRUDE und C8-Purification/F = see below/Vivaspin 2000/260 nm Conc. | |
| | T1_crude | | 2'430 pMol/A-3'645 nMol |
| | T2_F37-39_Na | | 227 pMol/μL-341 nMol |
| BMO 29.891237_Ch11 | 10 μMol Scale | 5'-CholesterylTEG-CholesterylTEG-(SpacerC18)7-dT(Determ. of concentration)-BiotinTEG-p-3' | see below |
| | | DMTrOFF-Synthesis-2000A-dT-CPG/SpacerC18 = 0.2M/Coupling: 1 + 2 = 20 min – 3 + 4 = 2 × 10 min – 5 – 10 = 10 min – 11 + 12 = 20 min/ CPG-Cleavage = NH3-Isoprop/CRUDE und C8-Purification/F = see below/Vivaspin 2000/260 nm Conc. | |
| | F42-45_Na | | 166 pMol/μL-248 nMol |
| | F47-49_Na | | 100 pMol/μL-150 nMol |
| BMO 29.891237Ch12 | 10 μMol Scale | 5'-CholesterylTEG-CholesterylTEG-(SpacerC18)7-dT(Determ. of concentration)-BiotinTEG-p-3' | see below |
| | | DMTrOFF-Synthesis-2000A-dT-CPG/SpacerC18 = 0.2M/Coupling: 1 + 2 = 20 min – 3 + 4 = 2 × 10 min – 5 – 10 = 10 min – 11 + 12 = 20 min/ CPG-Cleavage = NH3-Isoprop/CRUDE und C8-Purification/F = see below/Vivaspin 2000/260 nm Conc. | |
| | F51-53_Na | | 216 pMol/μL-324 nMol |
| | F56-59_Na | | 160 pMol/μL-250 nMol |

Exemplary Syntheses performed and results thereof:

A)

| | | | | | | | | | | |
|---|---|---|---|---|---|---|---|---|---|---|
| DK1194Ch02 | 1 µMol Scale | 5'- | | Myristic acid | Myristic acid | PEG-2000 | 6CarboxyFluos | Biotin-TEG | -3' | 11 pMol/µL | synthesized and determined |
| DK1197 | 1 µMol Scale | 5'- | Myristic acid | SpacerC9 | Myristic acid | PEG-2000 | 6CarboxyFluos | Biotin-TEG | -3' | 0.5 pMol/µL | synthesized and determined |
| DK1213 | 10 µMol Scale | 5'- | | Myristic acid | Myristic acid | SpacerC18 | 6CarboxyFluos | Biotin-TEG | -3' | 538 pMol/µL | 2 charges synthesized and determined |
| DK1214 | 1 µMol Scale | 5'- | | Myristic acid | Myristic acid | (SpacerC18) × 7 | 6CarboxyFluos | Biotin-TEG | -3' | 100 pMol/µL | synthesized and determined |

B)

| ID | Scale | End | Mod1 | Mod2 | Mod3 | Mod4 | Spacer | Label1 | Label2 | End2 | Amount | Notes |
|---|---|---|---|---|---|---|---|---|---|---|---|---|
| DK1213 | 10 µMol Scale | 5' | | | | Myristic acid | | 6CarboxyFluos | Biotin-TEG | -3' | 538 pMol/µL | 2 Charges synthesized and determined |
| DK1214 | 1 µMol Scale | 5' | | | | Myristic acid | (SpacerC18) × 7 | 6CarboxyFluos | Biotin-TEG | -3' | 100 pMol/µL | synthesized and determined |
| DK1218 | 1 µMol Scale | 5' | | Myristic acid | SpacerC9 | Myristic acid | (SpacerC18) × 7 | 6CarboxyFluos | Biotin-TEG | -3' | 40 pMol/µL | |
| DK1219 | 1 µMol Scale | 5' | | Myristic acid | SpacerC12 | Myristic acid | (SpacerC18) × 7 | 6CarboxyFluos | Biotin-TEG | -3' | 15 pMol/µL | |
| DK1220 | 1 µMol Scale | 5' | | Myristic acid | SpacerC18 | Myristic acid | (SpacerC18) × 7 | 6CarboxyFluos | Biotin-TEG | -3' | 56 pMol/µL | |
| DK1221 | 1 µMol Scale | 5' | | Myristic acid | Myristic acid | Myristic acid | (SpacerC18) × 7 | 6CarboxyFluos | Biotin-TEG | -3' | 38 pMol/µL | |
| DK1222 | 1 µMol Scale | 5' | | Cholesteryl-TEG | Cholesteryl-TEG | Cholesteryl-TEG | (SpacerC18) × 7 | 6CarboxyFluos | Biotin-TEG | -3' | 12 + 6 + 13 pMol/µL | synthesis difficulties |
| DK1223 | 1 µMol Scale | 5' | | Cholesteryl-TEG | SpacerC9 | Cholesteryl-TEG | (SpacerC18) × 7 | 6CarboxyFluos | Biotin-TEG | -3' | 74 pMol/µL | |
| DK1224 | 1 µMol Scale | 5' | | Cholesteryl-TEG | SpacerC12 | Cholesteryl-TEG | (SpacerC18) × 7 | 6CarboxyFluos | Biotin-TEG | -3' | 5 pMol/µL | |
| DK1225 | 1 µMol Scale | 5' | | Cholesteryl-TEG | SpacerC18 | Cholesteryl-TEG | (SpacerC18) × 7 | 6CarboxyFluos | Biotin-TEG | -3' | | synthesis difficulties |
| DK1226 | 1 µMol Scale | 5' | | Cholesteryl-TEG | Cholesteryl-TEG | Cholesteryl-TEG | (SpacerC18) × 7 | 6CarboxyFluos | Biotin-TEG | -3' | 20 pMol/µL | |
| DK1227 | 1 µMol Scale | 5' | | | Myristic acid | Myristic acid | (SpacerC18) × 7 | 6CarboxyFluos | Biotin-TEG | -3' | 9 pMol/µL | |
| DK1228 | 1 µMol Scale | 5' | | Cholesteryl-TEG | Cholesteryl-TEG | Cholesteryl-TEG | SpacerC3 | Cholesteryl-TEG | (SpacerC3) × 7 | 6CarboxyFluos | -3' | Biotin-TEG | |
| DK1229 | 1 µMol Scale | 5' | | Cholesteryl-TEG | SpacerC9 | SpacerC3 | Cholesteryl-TEG | Myristic acid | (SpacerC18) × 7 | 6CarboxyFluos | Biotin-TEG | -3' | |
| | 1 µMol Scale | 5' | | Cholesteryl-TEG | SpacerC12 | SpacerC9 | Myristic acid | (SpacerC18) × 7 | 6CarboxyFluos | Biotin-TEG | -3' | | |
| | 1 µMol Scale | 5' | | Cholesteryl-TEG | SpacerC12 | SpacerC12 | Myristic acid | (SpacerC18) × 7 | 6CarboxyFluos | Biotin-TEG | -3' | | |

-continued

| 1 µMol Scale | 5'- | Cholesteryl-TEG | SpacerC18 columns | Myristic acid | (SpacerC18) × 7 | 6CarboxyFluos | Biotin-TEG | -3' |
|---|---|---|---|---|---|---|---|---|
| DK1193 Biotin-TEG Myristic acid | CPG PA-1 | 11 | | 0.5 g | | 4.50 mL ACN | | |
| 10-1975 Cholesteryl-TEG | PA-2 | 13 | 0.1M | 1 × 0.25 g + 1 × 100 à µMol 11 + 4 Couplings | | 3.10 mL ACN | | |
| 10-1964 6CarboxyFluos | PA-3 | 11 | 0.1M | 1 × 0.25 g + 1 × 100 à µMol 11 + 4 Couplings | | 3.20 mL ACN | | |
| 10-1909 SpacerC9 | PA-4 | 2 | 0.1M | 1 × 100 µMol | | 1.00 mL ACN | | |
| 10-1928 SpacerC12 | PA-5 | 2 | 0.1M | 1 × 100 µMol | | 1.00 mL ACN | | |
| 10-1918 Spacer-C18 | PA-6 | 79 | 0.1M | 5 × 0.25 g 18 Couplings | | 16.00 mL ACN | | |

C)

| | | | | | | | | |
|---|---|---|---|---|---|---|---|---|
| DK1213 | 10 μMol Scale | 5'- | | Myristic acid | SpacerC18 | 6CarboxyFluos | Biotin-TEG | -3' | 538 pMol/μL | 2 Charges synthesized and determined |
| DK1214 | 1 μMol Scale | 5'- | | Myristic acid | (SpacerC18) x 7 | 6CarboxyFluos | Biotin-TEG | -3' | 100 pMol/μL | synthesized and determined |
| DK1218 | 1 μMol Scale | 5'- | Myristic acid | SpacerC9 | (SpacerC18) x 7 | 6CarboxyFluos | Biotin-TEG | -3' | 40 pMol/μL | |
| DK1219 | 1 μMol Scale | 5'- | Myristic acid | SpacerC12 | (SpacerC18) x 7 | 6CarboxyFluos | Biotin-TEG | -3' | 15 pMol/μL | |
| DK1220 | 1 μMol Scale | 5'- | Myristic acid | SpacerC18 | (SpacerC18) x 7 | 6CarboxyFluos | Biotin-TEG | -3' | 56 pMol/μL | |
| DK1221 | 1 μMol Scale | 5'- | Myristic acid | Myristic acid | (SpacerC18) x 7 | 6CarboxyFluos | Biotin-TEG | -3' | 38 pMol/μL | |
| DK1222 | 1 μMol Scale | 5'- | | Cholesteryl-TEG | (SpacerC18) x 7 | 6CarboxyFluos | Biotin-TEG | -3' | 12 + 6 + 13 pMol/μL | |
| DK1223 | 1 μMol Scale | 5'- | Cholesteryl-TEG | SpacerC9 | (SpacerC18) x 7 | 6CarboxyFluos | Biotin-TEG | -3' | synthesis difficulties | |
| DK1224 | 1 μMol Scale | 5'- | Cholesteryl-TEG | SpacerC12 | (SpacerC18) x 7 | 6CarboxyFluos | Biotin-TEG | -3' | 74 pMol/μL | |
| DK1225 | 1 μMol Scale | 5'- | Cholesteryl-TEG | SpacerC18 | (SpacerC18) x 7 | 6CarboxyFluos | Biotin-TEG | -3' | 5 pMol/μL | |
| DK1226 | 1 μMol Scale | 5'- | Cholesteryl-TEG | Cholesteryl-TEG | (SpacerC18) x 7 | 6CarboxyFluos | Biotin-TEG | -3' | synthesis difficulties | |
| DK1227 | 1 μMol Scale | 5'- | | Myristic acid | (SpacerC18) x 7 | 6CarboxyFluos | Biotin-TEG | -3' | 20 pMol/μL | |
| DK1228 | 1 μMol Scale | 5'- | | Cholesteryl-TEG | (SpacerC18) x 7 | 6CarboxyFluos | Biotin-TEG | -3' | 9 pMol/μL | |
| DK1229 | 1 μMol Scale | 5'- | Cholesteryl-TEG | SpacerC3 | SpacerC3 | Cholesteryl-TEG | (SpacerC3) x 7 | 6CarboxyFluos | -3' | |
| | 1 μMol Scale | 5'- | Cholesteryl-TEG | SpacerC9 | Myristic acid | 6CarboxyFluos | Biotin-TEG | -3' | no Synthesis | |
| | 1 μMol Scale | 5'- | Cholesteryl-TEG | SpacerC12 | Myristic acid | 6CarboxyFluos | Biotin-TEG | -3' | no Synthesis | |
| | 1 μMol Scale | 5'- | Cholesteryl-TEG | SpacerC18 | Myristic acid | 6CarboxyFluos | Biotin-TEG | -3' | no Synthesis | |
| DK1234 | 10 μMol Scale | 5'- | | Cholesteryl-TEG | Cholesteryl-TEG | dT (determination of concentration) | Biotin-TEG | -3' | 239 + 307 pMol/μL | |

D) Chemical Structures of the Exemplary Compounds Useful in Methods of the Invention as Well as Side Products The chemical structures of the exemplary compounds useful in methods of the invention as well as side products of synthesis are depicted in FIGS. 6 A and B.

E) Synthesis of Biotin-PEG-Lys-(C18)2

The synthesis of Biotin-PEG-Lys-(C18)2 of the invention is shown in FIG. 6 C.

F) Structures of Further Compounds Useful in Methods of the Invention and Reference Compounds, as Well as Intermediates Thereof For synthesis of compounds useful in methods of the invention and reference compounds, following intermediates were used:

cholesteryl-TEG-CE-PA (GlenResearch 10-1975),
myristic acid-CE-PA (inhouse production),
biotin-TEG-CE-PA (GlenResearch 10-1955),
biotin-dT-CE-PA (Glen Research 10-1038),
dT-CE-PA (GlenResearch 10-1030),
symmetric doubler-CE-PA (GlenResearch 10-1920),
PEG-200-CED-PA (ChemGenes CLP-2119),
6-Fluorescein-CE-PA (GlenResearch 10-1964) and
universal-CPG (Proligo 1000A M401010).

Structures of further compounds useful in methods of the invention and reference compounds, as well as intermediates are shown in FIG. 12.

2. Labelling of Cells Using Compounds Useful in Methods of the Invention

| | Linol (1,1'-dilinoleyl-3,3,3',3'-tetramethyl-indocarbocyanine perchlorate, Invitrogen) | Oleyl (NOF-BAM) | PKH26 (Myristic acid, behenic acid; SIGMA) | PKH67 (SIGMA) | PKH2 (SIGMA) | Phosphatidyl-ethanolamine (N-(4,4-difluoro-5,7-dimethyl-4-bora-3a,4a-diaza-s-indacene-3-propionyl)-1,2-dihexadecanoyl-sn-glycero-3-phosphoethanol-amine, triethyl-ammonium salt, Invitrogen) | Sphingomyelin (N-(4,4-difluoro-5,7-dimethyl-4-bora-3a,4a-diaza-s-indacene-3-penta-noyl)sphingosyl phosphocholine; Invitrogen) |
|---|---|---|---|---|---|---|---|
| WBCs | is taken up by most cells (more in comparison to other molecules (Exposure time: 20-50 ms) ✓ | is not taken up by all cells (granulocytes potentially negative) ✓ | stains granulocytes and almost all other blood cells (1 Exp.: 3 cells not stained) ✓ | stains almost all cells; apparently no monocytes, combination of linol and PKH67– all cells stained ✓ | does not stain all cells, other PKHs better ✓ | x | (x)- very bad |
| U937 | ✓ | | ✓ | | | | |
| MDA-MB468 | ✓ | ✓ not all | ✓ | | | | |
| Jurkats | ✓ | ✓ | ✓ | | | x | x |
| CHO | ✓ | | ✓ | | | x | x very weak |
| COS 7 | ✓ | | ✓ | | | x | x |
| Hela | ✓ | | ✓* | | | x/✓ very weak | ✓ |
| NIH 3T3 | ✓ | | ✓ | | | x | x |
| Epithelial cells | ✓ | ✓ | ✓ not all | ✓ | | ✓ not all | x | ✓ |

| | Cholesterol (Invitrogen; cholesteryl 4,4-difluoro-5-(2-pyrrolyl)-4-bora-3a,4a-diaza-s-indacene-3-undecanoate) | BMO 29.891133 ID: 3882 5'-XXYZ-3' X = Cholesteryl-TEG Y = PEG2000 Z = Fluos | BMO: 29.891132 ID: 3880 5'-XYZ-3' X = Cholesteryl-TEG Y = PEG2000 Z = Fluos | BMO: 29.891131 ID: 3879 5'-XYZ-3' X = a-Tocopherol-TEG Y = PEG2000 Z = Fluos | 1,1'-Dioctadecyl-3,3,3',3'-tetramethyl-indocarbocyanin perchlorate Sigma 42364 –100 mg | BMO: 15.000078 Sulfo-JA133-phenylboronic acid |
|---|---|---|---|---|---|---|
| WBCs | x | taken up by most cells (more in comparison to other molecules (Exposure time: 50-200 ms) ✓ | ✓ not all | ✓ not all | ✓ not all | ✓ not all |
| U937 | | ✓ | ✓ | ✓ | ✓ | |
| MDA-MB468 | | ✓ | ✓ | ✓ | ✓ | |
| Jurkats | x | ✓ | ✓ | ✓ | ✓ | |
| CHO | x | ✓ | ✓ | ✓ | ✓ | |
| COS 7 | x | ✓ | ✓ | ✓ | ✓ | |
| Hela | x/✓ | ✓ | ✓ | ✓ | ✓ | |
| NIH 3T3 | x | ✓ | | | ✓* | |
| Epithelial cells | x very weak | ✓ | ✓ | ✓ | ✓ | ✓ |

*one cell stained weakly
*one cell not stained

Example 3: Results of Experiments Relating to the Immobilization of Cells

The following applies for modular description of the compounds below:

X=hydrophobic moiety, Y=PEG2000, Z=Biotin-TEG, F=Fluos=fluorescein

In the following experiment, the recovery rate of cells was determined.

A)

| tested compound | modular structure | Internal Reference number | Recovery Rate | cells | concentration |
|---|---|---|---|---|---|
| Sunbright(OE-080CS)DADOO-Biotin | | 15.260250 | | | |
| BAM-SH | | 15.260254 | 28.0% | WBCs | |
| Cholesteryl-TEG-Cholesteryl-TEG-PEG2000-Biotin-TEG | 5'-XXYZ-3' | 29.891137 | 77.1% | WBCs | |
| Biotin-PEG2000-Boronic acid | | 15.260267 | 16.3% | WBCs | |
| Cholesteryl-TEG-Cholesteryl-TEG-PEG2000-Fluos-Biotin-TEG | 5'-XXYFZ-3' | 29.891180 | 71-90% 77.7% 62.3% 95.8% 77.9% 88.5% 69.7% 79.2% 72.5% | WBCs WBCs WBCs WBCs WBCs WBCs WBCs WBCs WBCs | 350 pmol/10e6 cells 350 pmol/10e6 cells 350 pmol/10e6 cells 350 pmol/10e6 cells 350 pmol/10e6 cells 350 pmol/10e6 cells 350 pmol/10e6 cells 350 pmol/10e6 cells 350 pmol/10e6 cells |
| 1,2 Distearoyl-sn-glycero-3-phosphoethanolamine-N-[biotinyl(PEG2000)] | DSPE-PEG(2000) Biotin (Avantilipids) | | 54-83% | WBCs | 350 pmol/10e6 cells |
| Myristic acid-Myristic acid-PEG2000-Fluos-Biotin-TEG | 5'-XXYFZ-3' | 29.891194 | 21-26% | WBCs | 350 pmol/10e6 cells |
| Biotin-PEG-lys-(C14)2 | | 15.260268 | 52-86% | WBCs | |
| Myristic acid-Myristic acid-(SpacerC18)7-Fluos-Biotin-TEG | 5'-XXYYYYYYFZ-3' (Y = Spacer) | 29.891214 | 78.9% 68.7% 90.5% 81.1% 65.9% 84.9% 85.1% | WBCs WBCs WBCs WBCs WBCs WBCs WBCs | 350 pmol/10e6 cells 350 pmol/10e6 cells 350 pmol/10e6 cells 350 pmol/10e6 cells 350 pmol/10e6 cells 350 pmol/10e6 cells 350 pmol/10e6 cells |
| Myristic acid-Myristic acid-SpacerC18-Fluos-Biotin-TEG | 5'-XXYFZ-3' (Y = Spacer) | 29.891213 | 67.4% 61.9% 80.2% 70.4% | WBCs WBCs WBCs WBCs | 350 pmol/10e6 cells 350 pmol/10e6 cells 350 pmol/10e6 cells 350 pmol/10e6 cells |

-continued

| tested compound | modular structure | Internal Reference number | Recovery Rate | cells | concentration | |
|---|---|---|---|---|---|---|
| Myristic acid-SpacerC9-Myristic acid-PEG2000-Fluos-Biotin-TEG | 5'-XSXYFZ-3' (S = Spacer) | 29.891197 | not enough material; staining not good | WBCs | | |
| Myristic acid-SpacerC9-Myristic acid-(SpacerC18)7-Fluos-Biotin-TEG | 5'-XXXYYYYYYYFZ-3' (Y = Spacer) | 29.891218 | 50.3% | WBCs | 350 pmol/10e6 cells | |
| | | | 55.1% | WBCs | 350 pmol/10e6 cells | |
| Myristic acid-Cholesteryl-TEG-(SpacerC18)7-Fluos-Biotin-TEG | 5'-XEYYYYYYYFZ-3' (Y = Spacer; X = Myr.; E = Chol.)) | 29.891227 | 64.9% | WBCs | 350 pmol/10e6 cells | |
| | | | 69.6% | WBCs | 350 pmol/10e6 cells | |
| | | | 77.8% | WBCs | 350 pmol/10e6 cells | |
| | | | 77.8% | WBCs | 350 pmol/10e6 cells | |
| (Myristic acid)3-(SpacerC18)7-Fluos-Biotin-TEG | 5'-XXXYYYYYYYFZ-3' (Y = Spacer) | 29.891221 | 46.0% | WBCs | 350 pmol/10e6 cells | |
| | | | 79.4% | WBCs | 350 pmol/10e6 cells | |
| | | | 68.8% | WBCs | 350 pmol/10e6 cells | |
| | | | 76.5% | WBCs | 350 pmol/10e6 cells | |
| | | | 83.4% | WBCs | 350 pmol/10e6 cells | |
| Myristic acid-SpacerC12-Myristic acid-(SpacerC18)7-Fluos-Biotin-TEG | 5'-XVXYYYYYYYFZ-3' (V = Spacer C12, Y = Spacer C18) | 29.891219 | 46.3% | WBCs | 350 pmol/10e6 cells | |
| | | | 39.4% | WBCs | 350 pmol/10e6 cells | |
| | | | 53.7% | WBCs | 350 pmol/10e6 cells | |
| | | | 56.6% | WBCs | 350 pmol/10e6 cells | |
| Myristic acid-SpacerC18-Myristic acid-(SpacerC18)7-Fluos-Biotin-TEG | 5'-XXXYYYYYYYFZ-3' (Y = Spacer C18) | 29.891220 | 35.8% | WBCs | 350 pmol/10e6 cells | |
| | | | 41.4% | WBCs | 350 pmol/10e6 cells | |
| | | | 55.9% | WBCs | 350 pmol/10e6 cells | |
| | | | 63.5% | WBCs | 350 pmol/10e6 cells | |
| Cholesteryl-TEG-Cholesteryl-TEG-(SpacerC18)7-Fluos-Biotin-TEG | 5'-XXXYYYYYYYFZ-3' (Y = Spacer C18) | 29.891222 | 52.6% | WBCs | 350 pmol/10e6 cells | |
| | | | 76.3% | WBCs | 350 pmol/10e6 cells | |
| | | | 80.3% | WBCs | 350 pmol/10e6 cells | |
| | | | 70.4% | WBCs | 350 pmol/10e6 cells | |
| | | | 71.3% | WBCs | 350 pmol/10e6 cells | |
| | | | 80.3% | WBCs | 350 pmol/10e6 cells | |
| | | | 4.1% | WBCs | 350 pmol/10e6 cells | |
| | | | 38.8% | WBCs | 350 pmol/10e6 cells | |
| | | | 13.0% | WBCs | 350 pmol/10e6 cells | |
| | | | 11.0% | WBCs | 350 pmol/10e6 cells | undiluted |
| | | | 77.0% | WBCs | 350 pmol/10e6 cells | 1:1 diluted |
| | | | 79.0% | WBCs | 350 pmol/10e6 cells | undiluted |
| | | | 23.0% | WBCs | 350 pmol/10e6 cells | 1:1 diluted |
| | | | 17.0% | WBCs | 350 pmol/10e6 cells | untreated |
| | | | 68.0% | WBCs | 350 pmol/10e6 cells | US + 10' 98° C. |
| | | | 61.0% | WBCs | 350 pmol/10e6 cells | untreated |
| | | | | | | US + 10' 98° C. |

-continued

| tested compound | modular structure | Internal Reference number | Recovery Rate | cells | concentration | |
|---|---|---|---|---|---|---|
| Cholesteryl-TEG-SpacerC12-Cholesteryl-TEG-(SpacerC18)7-Fluos-Biotin-TEG | 5'-XWXYYYYYYFZ-3' (W = Spacer C12, Y = Spacer C18) | 29.891224 | 119.4% | WBCs | 350 pmol/10e6 cells | |
| | | | 60.6% | WBCs | 350 pmol/10e6 cells | |
| | | | 64.4% | WBCs | 350 pmol/10e6 cells | |
| | | | 70.3% | WBCs | 350 pmol/10e6 cells | |
| | | | 78.1% | WBCs | 350 pmol/10e6 cells | |
| Cholesteryl-TEG-SpacerC18-Cholesteryl-TEG-(SpacerC18)7-Fluos-Biotin-TEG | 5'-XXXYYYYYYFZ-3' (Y = Spacer C18) | 29.891225 | 38.8% | WBCs | 350 pmol/10e6 cells | |
| | | | 46.5% | WBCs | 350 pmol/10e6 cells | |
| Cholesteryl-Myristic acid-TEG-(SpacerC18)7-Fluos-Biotin-TEG | 5'-EXYYYYYYFZ-3' (Y = Spacer; X = Myr.; E = Chol.) | 29.891228 | 76.1% | WBCs | 350 pmol/10e6 cells | |
| | | | 64.0% | WBCs | 350 pmol/10e6 cells | |
| | | | 17.4% | WBCs | 350 pmol/10e6 cells | |
| | | | 52.1% | WBCs | 350 pmol/10e6 cells | |
| Cholesteryl-TEG-Cholesteryl-TEG-(SpacerC18)7-Biotin-TEG | 5'-XXYYYYYYYTZ-3' (Y = Spacer C18) | 29.891234 | 9.6% | WBCs | 10 pmol/10e6 cells | |
| | | | 18.8% | WBCs | 100 pmol/10e6 cells | |
| | | | 24.9% | WBCs | 500 pmol/10e6 cells | |
| | | | 35.4% | WBCs | 1000 pmol/10e6 cells | |
| | | | 12.0% | WBCs | 350 pmol/10e6 cells | |
| | | | 22.0% | WBCs | 350 pmol/10e6 cells | |
| | | | 17.0% | WBCs | 350 pmol/10e6 cells | |
| | | | 27.0% | WBCs | 350 pmol/10e6 cells | |
| | | | 10.0% | WBCs | 350 pmol/10e6 cells | undiluted |
| | | | 12.0% | WBCs | 350 pmol/10e6 cells | 1:1 diluted |
| | | | 22.0% | WBCs | 350 pmol/10e6 cells | untreated |
| | | | 22.0% | WBCs | 350 pmol/10e6 cells | US + 10' 98° C. |
| | | | 12.0% | WBCs | 350 pmol/10e6 cells | 0.001% Tween20 |
| | | | 14.0% | WBCs | 350 pmol/10e6 cells | 0.0003% Tween20 |
| | | | 13.0% | WBCs | 350 pmol/10e6 cells | 0.0001% Tween21 |
| | | | 11.0% | WBCs | 350 pmol/10e6 cells | 0.00003% Tween20 |
| | | | 26.8% | WBCs | 300 pmol/10e6 cells | 0.000001% Tween21 |
| | | | 41.7% | WBCs | 1 nmol/10e6 cells | 0.000003% Tween22 |
| | | | 99.7% | WBCs | 10 nmol/10e6 cells | 0.0% Tween22 |
| | | | 36.0% | WBCs | 350 pmol/10e6 cells | undiluted |
| | | | 25.0% | WBCs | 350 pmol/10e6 cells | 1:1 diluted |
| | | | 13.0% | WBCs | 350 pmol/10e6 cells | untreated |
| | | | 23.0% | WBCs | 350 pmol/10e6 cells | US + 10' 98° C. |
| | | | 15.0% | WBCs | 350 pmol/10e6 cells | 0.001% Tween20 |
| | | | 18.0% | WBCs | 350 pmol/10e6 cells | 0.0003% Tween22 |
| | | | 28.0% | WBCs | 350 pmol/10e6 cells | 0.0001% Tween21 |
| | | | 36.0% | WBCs | 350 pmol/10e6 cells | 0.00003% Tween20 |
| | | | 20.0% | WBCs | 350 pmol/10e6 cells | 0.000003% Tween22 |
| | | | 23.0% | WBCs | 350 pmol/10e6 cells | 0.000001% Tween21 |
| | | | 25.0% | WBCs | 350 pmol/10e6 cells | 0.000003% Tween20 |
| | | | 35.0% | WBCs | 350 pmol/10e6 cells | 0.0% Tween22 |

-continued

| tested compound | modular structure | Internal Reference number | Recovery Rate | cells | concentration | |
|---|---|---|---|---|---|---|
| Biotin-PEG-Lysin-C18 (Stearic acid) | | 15.260271 | 21.0% | WBCs | 350 pmol/10e6 cells | also not better at higher concentrations |
| Biotin-PEG-Lysin-C22 (Behenic acid) | | | 27.0% | WBCs | 350 pmol/10e6 cells | also not better at higher concentrations |
| Biotin-PEG-Lysin-(C18)2 dissolved in | | | 4.8% | WBCs | 10 pmol/10e6 cells | |
| | | | 6.8% | WBCs | 100 pmol/10e6 cells | |
| | | | 21.8% | WBCs | 1 nmol/10e6 cells | |
| | | | 60.6% | WBCs | 10 nmol/10e6 cells | |
| | | | 43.0% | WBCs | 10 nmol/10e6 cells | |
| | | | 69.0% | WBCs | 50 nmol/10e6 cells | |
| | | | 81.8% | WBCs | 100 nmol/10e6 cells | |
| | | | 29.6% | WBCs | 1 nmol/10e6 cells | |
| | | | 68.5% | WBCs | 10 nmol/10e6 cells | |
| | | | 83.9% | WBCs | 100 nmol/10e6 cells | |
| | | | 9.0% | WBCs | 350 pmol/10e6 cells | 0.001% Tween20 |
| | | | 10.0% | WBCs | 350 pmol/10e6 cells | 0.0003% Tween20 |
| | | | 10.0% | WBCs | 350 pmol/10e6 cells | 0.0001% Tween21 |
| | | | 15.0% | WBCs | 350 pmol/10e6 cells | 0.00003% Tween22 |
| | | | 75.0% | WBCs | 100 nmol/10e6 cells | |
| | | | 44.0% | WBCs | 5 nmol/10e6 cells | |
| | | | 25.0% | WBCs | 0.5 nmol/10e6 cells | |
| | | | 66.0% | WBCs | 100 nmol/10e6 cells | |
| | | | 34.0% | WBCs | 5 nmol/10e6 cells | |
| | | | 27.0% | WBCs | 0.5 nmol/10e6 cells | |
| | | | 33.0% | WBCs | 100 nmol/10e6 cells | may be to due 1.5-2 h exposure of plate |
| | | | 16.0% | WBCs | 5 nmol/10e6 cells | |
| | | | 38.0% | WBCs | 0.5 nmol/10e6 cells | |
| Cholesteryl-TEG-Cholesteryl-TEG-(SpacerC18)7-Biotin-TEG | 5'-XXYYYYYYYTZ-3' (Y = Spacer C18) | 29.891234 | 18.0% | WBCs | 350 pmol/10e6 cells | not evaporated, VIVA Spin |
| | | | 42.0% | WBCs | 1000 pmol/10e6 cells | nicht not evaporated, VIVA Spin |
| Cholesteryl-TEG-Cholesteryl-TEG-(SpacerC18)7-Biotin-TEG | 5'-XXYYYYYYYTZ-3' (Y = Spacer C18) | 29.891234 | 19.0% | WBCs | 350 pmol/10e6 cells | not evaporated, VIVA Spin |
| | | | 45.0% | WBCs | 1000 pmol/10e6 cells | not evaporated, VIVA Spin |

-continued

| tested compound | modular structure | Internal Reference number | Recovery Rate | cells | concentration |
|---|---|---|---|---|---|
| 5'-(Cholesteryl-TEG)2-(SpacerC18)7-dT-Biotin-TEG-3' | 5'-YYXXXXXXXTZ-3' (X = SpacerC18) | 29.891234 | 7.0%<br>13.0% | WBCs<br>WBCs | 350 pmol/10e6 cells<br>1 nmol/10e6 cells |
| 5'-(Cholesteryl-TEG)2-(SpacerC18)7-dT-Biotin-TEG-3' | 5'-YYXXXXXXXTZ-3' (X = SpacerC18) | 29.891234 | 63.0%<br>71.0% | WBCs<br>WBCs | 350 pmol/10e6 cells<br>1 nmol/10e6 cells |
| 5'-(Cholesteryl-TEG)2-(SpacerC18)7-dT-Biotin-TEG-3' | 5'-YYXXXXXXXTZ-3' (X = SpacerC18) | 29.891234 | 52.0%<br>78.0% | WBCs<br>WBCs | 350 pmol/10e6 cells<br>1 nmol/10e6 cells |
| 5'-(Cholesteryl-TEG)2-(SpacerC18)7-SpacerC3-dT-Biotin-TEG-3' | 5'-YYXXXXXXXWTZ-3' (W = Spacer C3, X = SpacerC18) | 29.891234 | 33.0%<br>44.0% | WBCs<br>WBCs | 350 pmol/10e6 cells<br>1 nmol/10e6 cells |
| 5'-(Cholesteryl-TEG)2-(SpacerC18)7-SpacerC3-dT-Biotin-TEG-3' | 5'-YYXXXXXXXWTZ-3' (W = Spacer C3, X = SpacerC18) | 29.891236 | 46.0%<br>64.0% | WBCs<br>WBCs | 350 pmol/10e6 cells<br>1 nmol/10e6 cells |
| 5'-(Cholesteryl-TEG)2-(SpacerC18)7-SpacerC3-dT-Biotin-TEG-3' | 5'-YYXXXXXXXWTZ-3' (W = Spacer C3, X = SpacerC18) | 29.891237 | 37.0%<br>47.0% | WBCs<br>WBCs | 350 pmol/10e6 cells<br>1 nmol/10e6 cells |
| 5'-(Cholesteryl-TEG)2-(SpacerC18)7-dT-Biotin-TEG-3' | 5'-YYXXXXXXXWTZ-3' (W = Spacer C3, X = SpacerC18) | 29.891237 | 8.1%<br>15.1%<br>41.3%<br>59.1% | WBCs<br>WBCs<br>WBCs<br>WBCs | 10 pmol/10e6 cells<br>100 pmol/10e6 cells<br>1 nmol/10e6 cells<br>10 nmol/10e6 cells |
| 5'-(Cholesteryl-TEG)2-(SpacerC18)7-dT-Biotin-TEG-3' | 5'-YYXXXXXXXWTZ-3' (W = Spacer C3, X = SpacerC18) | 29.891244 | 10.5%<br>16.4%<br>35.4%<br>62.0% | WBCs<br>WBCs<br>WBCs<br>WBCs | 10 pmol/10e6 cells<br>100 pmol/10e6 cells<br>1 nmol/10e6 cells<br>10 nmol/10e6 cells |
| 5'-(Cholesteryl-TEG)-(SpacerC18)7-dT-Biotin-TEG-3' | 5'-XYXXXXXXXTZ-3' (W = Spacer C3, X = SpacerC18) | 29.891244 | 14.00%<br>27.00%<br>51.00%<br>57.00% | WBCs<br>WBCs<br>WBCs<br>WBCs | 10 pmol/10e6 cells<br>100 pmol/10e6 cells<br>1 nmol/10e6 cells<br>10 nmol/10e6 cells |
| 5'-(Cholesteryl-TEG)2-(SpacerC18)7-dT-Biotin-TEG-3' | 5'-YYXXXXXXXWTZ-3' (W = Spacer C3, X = SpacerC18) | 29.891246 | 9.50%<br>20.50%<br>50.70%<br>68.90% | | 10 pmol/10e6 cells<br>100 pmol/10e6 cells<br>1 nmol/10e6 cells<br>10 nmol/10e6 cells |

-continued

| tested compound | modular structure | Internal Reference number | Recovery Rate | cells | concentration |
|---|---|---|---|---|---|
| 5'-(SpacerC18)7-dT-Biotin-TEG-3' | 5'-XXXXXXXTZ-3'<br>(W = Spacer C3,<br>X = SpacerC18) | 29.891245 | 9.30%<br>6.20%<br>8.40%<br>27.50% | | 10 pmol/10e6 cells<br>100 pmol/10e6 cells<br>1 nmol/10e6 cells<br>10 nmol/10e6 cells |
| 5'-(Cholesteryl-TEG)2-(SpacerC18)7-dT-Biotin-TEG-3' | 5'-YYXXXXXXXTZ-3'<br>(W = Spacer C3,<br>X = SpacerC18) | 29.891246 | 74.50% | | 10 nmol/10e6 cells |
| 5'-(Cholesteryl-TEG)-(SpacerC18)7-dT-Biotin-TEG-3' | 5'-YXXXXXXXTZ-3'<br>(W = Spacer C3,<br>X = SpacerC18) | 29.891244 | 51.70% | | 10 nmol/10e6 cells |
| 5'-(SpacerC18)7-dT-Biotin-TEG-3' | 5'-XXXXXXXTZ-3'<br>(W = Spacer C3,<br>X = SpacerC18) | 29.891245 | 24.70% | | 10 nmol/10e6 cells |
| Mixture of 44 + 45 + 46 | | | 66.90% | | 10 nmol/10e6 cells |
| 5'-(Cholesteryl-TEG)2-(SpacerC18)7-dT-Biotin-TEG-3' | 5'-YYXXXXXXXTZ-3'<br>(W = Spacer C3,<br>X = SpacerC18) | 29.891246 | 87.16% | | 10 nmol/10e6 cells |
| 5'-(Cholesteryl-TEG)-(SpacerC18)7-dT-Biotin-TEG-3' | 5'-YXXXXXXXTZ-3'<br>(W = Spacer C3,<br>X = SpacerC18) | 29.891244 | 63.70% | | 10 nmol/10e6 cells |
| 5'-(SpacerC18)7-dT-Biotin-TEG-3' | 5'-XXXXXXXTZ-3'<br>(W = Spacer C3,<br>X = SpacerC18) | 29.891245 | 26.50% | | 10 nmol/10e6 cells |
| Mixture of 44 + 45 + 46 | | | 79.46% | | 10 nmol/10e6 cells |
| 5'-(Cholesteryl-TEG)-dT-Biotin-TEG-3' | 5'-XTZ-3'<br>(W = Spacer 03,<br>X = SpacerC18) | 29891240 | 12.80%<br>14.90% | | 1 nmol/10e6 cells<br>10 nmol/10e6 cells |
| 5'-(Cholesteryl-TEG)2-(SpacerC18)7-dT-Biotin-TEG-3' | 5'-YYXXXXXXXTZ-3'<br>(W = Spacer C3,<br>X = SpacerC18) | 29.891246 | 85.50% | | 1 nmol 1C18 +<br>10 nmol CholChol |
| Mix | | | 83.22% | | 10 nmol 1C18 +<br>10 nmol CholChol |

-continued

| tested compound | modular structure | Internal Reference number | Recovery Rate | cells | concentration |
|---|---|---|---|---|---|
| 1,2 Distearoyl-sn-glycero-3-phosphoethanolamine-N-[biotinyl(PEG2000) | DSPE-PEG(2000) Biotin (Avantilipids) | | 70.80% | | 10 nmol/10^6 Distearine without EDTA-K |
| | | | 71.60% | | 10 nmol/10^6 Distearine 0.3 mM EDTA-K |
| | | | 76.50% | | 10 nmol/10^6 Distearine 1 mM EDTA-K |
| | | | 72.00% | | 10 nmol/10^6 Distearine 3 mM EDTA-K |
| | | | 78.30% | | 10 nmol/10^6 Distearine without EDTA-K |
| | | | 82.70% | | 10 nmol/10^6 Distearine 0.3 mM EDTA-K |
| | | | 88.50% | | 10 nmol/10^6 Distearine 1 mM EDTA-K |
| | | | 81.80% | | 10 nmol/10^6 Distearine 3 mM EDTA-K |
| | | | 68.90% | | 10 pmol/10e6 cells |
| | | | 69.60% | | 100 pmol/10e6 cells |
| | | | 68.90% | | 1 nmol/10e6 cells |
| | | | 95.90% | | 10 pmol/10e6 cells |
| | | | 84.40% | | 10 pmol/10e6 cells |
| | | | 90.80% | | 10 pmol/10e6 cells |
| 1,2-Dioleyl-sn-Glycero-3-Phosphoethanolamin-N-(Cap-Biotin)-Na | Avantilipids | | 66.30% | | 10 pmol/10e6 cells |
| | | | 91.10% | | 100 pmol/10e6 cells |
| | | | 95.80% | | 1 nmol/10e6 cells |
| | | | 20.60% | | without Linker |
| | | | 74.40% | | 10 pmol/10e6 cells |
| | | | 107.10% | | 100 pmol/10e6 cells |
| | | | 101.76% | | 1 nmol/10e6 cells |
| | | | 26.85% | | without Linker |
| | | | 81.00% | | 100 pmol/10e6 cells |
| | | | 80.10% | | 100 pmol/10e6 cells |
| | | | 64.90% | | 100 pmol/10e6 cells |
| | | | 80.55% | | 100 pmol/10e6 cells |
| | | | 70.85% | | 100 pmol/10e6 cells |
| | | | 80.74% | | 100 pmol/10e6 cells |
| | | | 53.97% | | 100 pmol/10e6 cells |
| | | | 69.60% | | 100 pmol/10e6 cells |
| | | | 80.16% | | 500 pmol/10e6 cells |
| | | | 95.94% | | 500 pmol/10e6 cells |

-continued

| tested compound | modular structure | Internal Reference number | Recovery Rate | cells | concentration |
|---|---|---|---|---|---|
| Dipalmityl-sn-Glycero-3-Phosphoethanolamin-N-(Cap-Biotin)-Na | Avantilipids | | 89.19% | | 10 nmol/10e6 cells |
| | | | 105.12% | | 10 nmol/10e6 cells |
| | | | 54.30% | | 10 pmol/10e6 cells |
| | | | 72.20% | | 100 pmol/10e6 cells |
| | | | 84.90% | | 1 nmol/10e6 cells |
| | | | 11.10% | | without Linker |
| | | | 45.40% | | 10 pmol/10e6 cells |
| | | | 86.10% | | 100 pmol/10e6 cells |
| | | | 89.30% | | 1 nmol/10e6 cells |
| | | | 14.10% | | without Linker |
| | | | 51.80% | | 300 pmol/10e6 cells |
| | | | 55.90% | | 300 pmol/10e6 cells |
| | | | 52.60% | | 300 pmol/10e6 cells |
| | | | 73.07% | | 300 pmol/10e6 cells |
| | | | 61.27% | | 300 pmol/10e6 cells |
| | | | 71.40% | | 300 pmol/10e6 cells |
| 5'-(Cholesteryl-TEG)2-PEG2000-Fluos-Biotin_TEG-3' | purified | 29.891.247 | 13.38% | | 10 pmol/10e6 cells |
| | | | 15.26% | | 100 pmol/10e6 cells |
| | | | 13.27% | | 1 nmol/10e6 cells |
| | | | 45.75% | | 10 nmol/10e6 cells |
| 5'-(Cholesteryl-TEG)2-Spacer C18-Fluos-Biotin_TEG-3' | purified | 29.891.251 | 25.57% | | 10 pmol/10e6 cells |
| | | | 57.82% | | 100 pmol/10e6 cells |
| | | | 89.71% | | 1 nmol/10e6 cells |
| | | | 92.63% | | 10 nmol/10e6 cells |
| | | | 68.57% | | 100 nmol/10e6 cells |
| | | | 82.61% | | 1 nmol/10e6 cells |
| 5'-(Cholesteryl-TEG)2-PEG2000-Fluos-Biotin_TEG-3' INVERS | purified | 29.891248 | 32.80% | | 10 pmol/10e6 cells |
| | | | 65.36% | | 100 pmol/10e6 cells |
| | | | 83.99% | | 1 nmol/10e6 cells |
| | | | 81.10% | | 10 nmol/10e6 cells |
| | | | 70.75% | | 100 pmol/10e6 cells |
| | | | 86.03% | | 1 nmol/10e6 cells |
| 5'-(Cholesteryl-TEG)2-Spacer C18-Fluos-Biotin_TEG-3' INVERS | purified | 29.891254 | 40.30% | | 10 pmol/10e6 cells |
| | | | 64.60% | | 100 pmol/10e6 cells |
| | | | 92.50% | | 1 nmol/10e6 cells |
| | | | 83.60% | | 10 nmol/10e6 cells |
| | | | 57.63% | | 100 pmol/10e6 cells |
| | | | 82.19% | | 1 nmol/10e6 cells |
| | | | 65.69% | | 100 pmol/10e6 cells |
| | | | 81.79% | | 1 nmol/10e6 cells |
| | | | 70.07% | | 100 pmol/10e6 cells |
| | | | 81.28% | | 100 pmol/10e6 cells |
| | | | 74.68% | | 1 nmol/10e6 cells |

-continued

| tested compound | modular structure | Internal Reference number | Recovery Rate | cells | concentration | |
|---|---|---|---|---|---|---|
| 3'-(Myristic acid) 2-PEG2000-dT-Biotin-TEG-5' INVERS | unpurified | 29.891255 | 24.70%<br>50.61%<br>87.55%<br>83.53% | | 10 pmol/10e6 cells<br>100 pmol/10e6 cells<br>1 nmol/10e6 cells<br>10 nmol/10e6 cells | |
| 3'-(Myristic acid) 2-PEG2000-Fluos-Biotin-TEG-5' INVERS | unpurified | 29.891256 | 35.79%<br>73.42%<br>85.13% | | 10 pmol/10e6 cells<br>100 pmol/10e6 cells<br>1 nmol/10e6 cells | |
| 5'-(Cholesteryl-TEG)2-PEG2000-dT-Biotin_TEG-3' | unpurified | 29.891249 | 11.38%<br>16.16%<br>37.73%<br>61.04% | | 10 pmol/10e6 cells<br>100 pmol/10e6 cells<br>1 nmol/10e6 cells<br>10 nmol/10e6 cells | |
| 5'-(Cholesteryl-TEG)2-Spacer C18-dT-Biotin_TEG-3' INVERS | unpurified | 29.891252 | 28.56%<br>55.41%<br>71.99%<br>88.05%<br>16.03%<br>52.46%<br>80.83%<br>85.47% | | 10 pmol/10e6 cells<br>100 pmol/10e6 cells<br>1 nmol/10e6 cells<br>10 nmol/10e6 cells<br>10 pmol/10e6 cells<br>100 pmol/10e6 cells<br>1 nmol/10e6 cells<br>10 nmol/10e6 cells | |
| 5'-(Cholesteryl-TEG)2-Spacer C12-dT-Biotin_TEG-3' INVERS | unpurified | 29.891253 | 47.42%<br>73.46%<br>96.84%<br>102.36%<br>41.44%<br>72.13%<br>62.59%<br>79.02% | | 10 pmol/10e6 cells<br>100 pmol/10e6 cells<br>1 nmol/10e6 cells<br>10 nmol/10e6 cells<br>10 pmol/10e6 cells<br>100 pmol/10e6 cells<br>1 nmol/10e6 cells<br>10 nmol/10e6 cells | |
| 5'-(Chol-TEG)1-Doubler-dT-Biotin-3' | | 29.891272 | 65.03%<br>83.08%<br>87.93%<br>Cells lysed<br>56.49%<br>72.13%<br>62.11%<br>82.47%<br>82.01% | | 10 pmol/10e6 cells<br>100 pmol/10e6 cells<br>1 nmol/10e6 cells<br>10 nmol/10e6 cells<br>10 pmol/10e6 cells<br>100 pmol/10e6 cells<br>1 nmol/10e6 cells<br>10 nmol/10e6 cells<br>100 pmol/10e6 cells | Vesicle formation |

-continued

| tested compound | modular structure | Internal Reference number | Recovery Rate | cells | concentration |
|---|---|---|---|---|---|
| 5'-(Cholesteryl-TEG)2-PEG2000-dT-Biotin_TEG-3' | purified | 29.891249 | 50.49%<br>87.24% | | 100 pmol/10e6 cells<br>1 nmol/10e6 cells |
| 5'-(Cholesteryl-TEG)2-PEG2000-Fluos-Biotin_TEG-3' INVERS | purified | 29.891250 | 48.66%<br>81.29% | | 100 pmol/10e6 cells<br>1 nmol/10e6 cells |
| 5'-(Cholesteryl-TEG)2-Spacer C18-dT-Biotin_TEG-3' INVERS | purified | 29.891252 | 28.18%<br>61.88% | | 100 pmol/10e6 cells<br>1 nmol/10e6 cells |
| 5'-(Cholesteryl-TEG)2-Spacer C12-dT-Biotin_TEG-3' INVERS | purified | 29.891253 | 71.41%<br>86.21% | | 100 pmol/10e6 cells<br>1 nmol/10e6 cells |

B)

| Molecule/combination thereof tested | Internal number | Recovery rate treated cells (SA-plate) | Recovery rate untreated cells (SA plate) | Recovery rate treated cells (untreated-plate) | Recovery rate untreated cells (ntreated plate) | Remarks |
|---|---|---|---|---|---|---|
| Cholesterol- Compound (5'-XXYFZ-3') | 29.891180 | 73.2% | 16.3% | 56.7% | 68.7% | strong staining |
| Boronic acid- Compound (single) | 15.260267 | 16.3% | 13.0% | 32.5% | 41.3% | |
| Cholesterol- Compound (5'-XXYFZ-3') | 29.891180 | 71.7% | 24.4% | | | |
| Distearoyl- Compound (Avanti) | | 53.8% | | | | |
| Chol-Compound + Distearoyl-Compound | 29.891180 | 74.7% | | | | |
| Cholesterol- Compound (5'-XXYFZ-3') | 29.891180 | 83.2% | 30.6% | | | |
| Distearoyl- compound (Avanti) | | 66.7% | | | | |
| Chol-Compound + Distearoyl-Compound | 29.891180 | 80.2% | | | | |
| Cholesterol- Compound 200 µl Zellsus. | 29.891180 | 67.6%/71.9% | | | | |
| Cholesterol- Compound 400 µl Zellsus. | 29.891180 | 78.4%/84.1% | | | | |
| Cholesterol- Compound 800 µl Zellsus. | 29.891180 | 81.1%/86.4% | | | | |
| Cholesterol- Compound (5'-XXYFZ-3') | 29.891180 | 80.9% | 30.8% | | | |
| Distearoyl- Compound (Avanti) | | 50.6% | | | | |
| Chol-Compound + Distearoyl-Compound | 29.891180 | 77.8% | | | | |
| Myristic acid-Compound (5'-XXYFZ-3')C1 | 29.891194 | 20.7% | 21.6% | | | weak Staining |
| Myristic acid-Compound (5'-XXYFZ-3')C2 | 29.891194 | 22.1% | | | | |
| Myristic acid-Compound (5'-XXYFZ-3')C1 | 29.891194 | 33.1% | 19.5% | | | stronger Staining |
| Myristic acid-Compound (C14-Lys-PEG) | 15.260268 | 47.7% | 19.5% | | | |
| Cholesterol- Compound (5'-XXYFZ-3') | 29.891194 | 63.4% | 10.7% | | | |
| Myristic acid-Compound (C14-Lys-PEG) | 15.260268 | 53.9% | | | | |
| Chol-Compound + Myr.-Compound | 29.891194/15.260268 | 43.6% | | | | |
| Chol-Compound + Myr.-Compound | 29.891194/15.260268 | 43.6% | | | | |
| Chol-Compound 2.16 µg/2 × 10e6 WBCs | 29.891180 | 78.6% | | | | |
| Chol-Compound 21.6 µg/2 × 10e6 WBCs | 29.891180 | 68.6% | | | | |
| Chol-Compound 216 µg/2 × 10e6 WBCs | 29.891180 | 50.1% | | | | |
| Myr-Compound 2.16 µg/2 × 10e6 WBCs | 15.260268 | 39.6% | | | | higher conc. will be tested again |
| Myr-Compound 21.6 µg/2 × 10e6 WBCs | 15.260268 | 46.7% | | | | |
| Myr-Compound 216 µg/2 × 10e6 WBCs | 15.260268 | 51.8% | | | | |
| Cholesterol- Compound (5'-XXYFZ-3') | 29.891194 | 89.6% | | | | |
| Distearoyl- Compound (Avanti) | | 82.6% | | | | |
| Myristic acid.-Compound (C14-Lys-PEG) | 15.260268 | 85.7% | | | | |
| Chol-Compound + Distearoyl-Compound | 29.891194 | 84.3% | | | | |
| Chol-Compound + Myr.-Compound | 29.891194/15.260268 | 91.3% | | | | |
| Chol + Distearoyl + Myr | 29.891194/15.260268 | 87.0% | | | | |
| Cholesterol- Compound (5'-XXYFZ-3') | 29.891194 | 74.0% | | | | |
| Distearoyl- Compound (Avanti) | | 53.5% | | | | |
| Myristic acid.-Compound (C14-Lys-PEG) | 15.260268 | 45.6% | | | | |
| Chol-Compound + Distearoyl-Compound | 29.891194 | 71.7% | | | | |
| Chol-Compound + Myr.-Compound | 29.891194/15.260268 | 68.4% | | | | |
| Chol + Distearoyl + Myr | 29.891194/15.260268 | 64.9% | | | | |
| Chol- Compound 10 min 4° C. | 29.891194 | 81.6% | | | | |
| Chol- Compound 60 min 4° C. | 29.891194 | 81.7% | | | | |
| Chol- Compound 10 min RT | 29.891194 | 88.3% | | | | |

| Molecule/combination thereof tested | Internal number | Recovery rate treated cells (SA-plate) | Recovery rate untreated cells (SA plate) | Recovery rate treated cells (untreated-plate) | Recovery rate untreated cells (ntreated plate) | Remarks |
|---|---|---|---|---|---|---|
| Chol- Compound 60 min RT | 29.891194 | 85.5% | | | | |
| Chol- Compound 10e4 MDAs in WBCs | 29.891194 | 99.0% | | | | |
| Chol- Compound 5 × 10e5 WBCs | 29.891194 | 70.0% | | | | |
| Chol- Compound 20e3 MDAs in WBCs | 29.891194 | 102.0% | | | | |
| Chol- Compound 5 × 10e5 WBCs | 29.891194 | 70.8% | | | | |
| Chol- Compound 40e3 MDAs in WBCs | 29.891194 | 102.0% | | | | |
| Chol- Compound 10e6 WBCs | 29.891194 | 69.4% | | | | |
| Myr-Myr-C18-Fluos | 29.891213 | 67.4% | | | | strong staining |
| Myr-Myr-PEG-Fluos | 29.891194 | 24.4% | | | | weak staining |
| Myr-Myr-7 × C18-Fluos | 29.891214 | 78.9% | | | | strong staining |
| Myr-C9-Myr-PEG-Fluos | 29.891197 | not enough material | | | | weak staining |

C) Comparison of Results Obtained Upon Pretreatment of Either the Wells of the Plate or the Cells with Molecules Useful in Methods of the Invention The experiments were performed for different incubation times, as shown below:

| 30 min Well | target: 300.000 WBC | | MW | Standard deviation | Mean % | Standard deviation % |
|---|---|---|---|---|---|---|
| a1 | Well treated | 61470 | | | 21.64 | 2.71 |
| a2 | Well treated | 67259 | | | | |
| a3 | Well treated | 74951 | | | | |
| a4 | Well treated | 55956 | 64909 | 8131.2 | | |
| b1 | untreated | 55575 | | | | |
| b2 | untreated | 32017 | | | 9.69 | 6.56 |
| b3 | untreated | 17166 | | | | |
| b4 | untreated | 11481 | 29059.75 | 19683.1 | | |
| c1 | WBC treated | 213072 | | | | |
| c2 | WBC treated | 237475 | | | 77.28 | 4.39 |
| c3 | WBC treated | 243445 | | | | |
| c4 | WBC treated | 233327 | 231829.75 | 13176.7 | | |

| 90 min Well | target: 300.000 WBC | | MW | Standard deviation | Mean % | Mean % |
|---|---|---|---|---|---|---|
| a1 | Well treated | 124492 | | | | |
| a2 | Well treated | 143548 | | | 47.62 | 4.33 |
| a3 | Well treated | 154212 | | | | |
| a4 | Well treated | 149208 | 142865 | 13000.28 | | |
| b1 | untreated | 46601 | | | | |
| b2 | untreated | 29206 | | | 9.32 | 4.58 |
| b3 | untreated | 21199 | | | | |
| b4 | untreated | 14882 | 27972 | 13732.98 | | |
| c1 | WBC treated | 237185 | | | | |
| c2 | WBC treated | 252944 | | | 83.12 | 2.72 |
| c3 | WBC treated | 254697 | | | | |
| c4 | WBC treated | 252559 | 249346.25 | 8160.72 | | |

| 120 min Well | target: 300.000 WBC | | MW | Standard deviation | Mean % | Mean % |
|---|---|---|---|---|---|---|
| a1 | Well treated | | 167671 | | | |
| a2 | Well treated | | 177678 | | 57.02 | 6.37 |
| a3 | Well treated | | 192194 | | | |
| a4 | Well treated | | 146708 | 171062.75 | 19104.5 | |
| b1 | untreated | 46402 | | | | |
| b2 | untreated | 35669 | | | 9.74 | 4.88 |
| b3 | untreated | 20989 | | | | |
| b4 | untreated | 13798 | 29214.5 | 14633.3 | | |
| c1 | WBC treated | 256949 | | | | |
| c2 | WBC treated | 268552 | | | 86.23 | 2.43 |
| c3 | WBC treated | 258291 | | | | |
| c4 | WBC treated | 250979 | 258692.75 | 7300.9 | | |

The results on immobilization are summarized as follows:

| | 30 min | | 90 min | | 120 min | |
|---|---|---|---|---|---|---|
| | WBC recovery rate [%] | Standard deviation | WBC recovery rate [%] | Standard deviation | WBC recovery rate [%] | Standard deviation |
| molecule useful in methods invention bound to surface | 21.64 | 2.71 | 47.6 | 4.33 | 57.02 | 6.37 |
| molecule useful in methods of invention + cells | 77.28 | 4.39 | 83.1 | 2.72 | 86.23 | 2.43 |
| untreated | 9.69 | 6.56 | 9.3 | 4.58 | 9.74 | 4.88 |

| | 30 min | 90 min | 120 min |
|---|---|---|---|
| molecule useful in methods of invention bound to surface | 21.64 | 47.6 | 57.02 |
| molecule useful in methods of invention + cells | 77.28 | 83.1 | 86.23 |
| untreated | 9.69 | 9.3 | 9.74 |

D) Determination of Recovery Rate for Exemplary Compound Biotin-PEG-Lys-(C14)2:

The following recovery rate was determined for compound Biotin-PEG-lys-(C14)2:

M=2708.90 g/mol
5.4 mg/10 ml EtOH
c=n/V=m/M*V c=5.4 g/(2708.9 g/mol*10 l)=1.99 10e-4 mol/l
1.99*10e-4 mol/l=7.96 nmol/4 μl
4 μl=4.5*10e6 Cells
→1.77 nmol/10e6 Cells
Recovery rate in this experiment: 85.72

Example 4: Comparison of Compounds Useful in Methods of the Invention Containing One Vs. Two Hydrophobic Moieties Aim of this experiment: Testing of the white blood cell immobilization on a streptavidin-coated surface using different molecules useful in methods of the invention. In particular, the performance of a single cholesterol-molecule and different dual-linker molecules (i.e. containing two hydrophobic moieties) was tested. In detail, immobilization of white blood cells (WBCs) on a Streptavidin-coated surface using different linker molecules was tested on a 12-well plate: 300 000 WBCs/well. This was followed by the measurement of the cell recovery rate after immobilization and washing of the cells using the Cellavista instrument (10× Nuclei Operator s9s5).

| Molecule tested | Characteristics | Internal No | Structure |
|---|---|---|---|
| 5'-(Cholesterol-TEG)1-Doubler-dT-Biotin-3' | Mono-linker | 29.891272 | 5'-Y\\<br>　　XZ-3'<br>　　/<br>5'-<br>Y = Cholesteryl-TEG<br>X = Doubler<br>Z = dTBiotin |
| 5'-(Cholesteryl-TEG)2-Spacer C12-dT-Biotin_TEG-3' INVERS | Dual linker | 29.891253 | 3'-YYXTZ-5'<br>Y = Cholesteryl-TEG<br>X = Spacer C12<br>Z = Biotin-TEG |
| 5'-(Cholesteryl-TEG)2-Spacer C18-Fluos-Biotin_TEG-3' INVERS | Dual linker | 29.891254 | 3'-YYXWZ-5'<br>Y = Cholesteryl-TEG<br>X = Spacer C18<br>W = Fluorescein<br>Z = Biotin-TEG |

The results are as follows:
Sample 1

| | compound internal reference No. | | Mean | standard deviation | Recovery rate | standard deviation |
|---|---|---|---|---|---|---|
| A1 | 29.891253 | 105061 | | | | |
| B1 | 29.891253 | 128195 | 17632.25 | | 41.44% | 5.88% |
| C1 | 29.891253 | 139678 | | | | |
| A2 | 29.891254 | 157660 | | | | |
| B2 | 29.891254 | 190148 | 16339.42 | | 57.63% | 5.45% |
| C2 | 29.891254 | 170850 | | | | |
| A3 | 29.891272 | 147132 | | | | |
| B3 | 29.891272 | 179643 | 19366.19 | | 56.49% | 6.46% |
| C3 | 29.891272 | 181620 | | | | |

-continued

| compound internal reference No. | Mean | standard deviation | Recovery rate | standard deviation |
|---|---|---|---|---|
| compound concentration: 1 nmol/10e6 WBCs | | | | |
| A1 | 29.891253 | 218861 | | |
| B1 | 29.891253 | 221471 | | |
| C1 | 29.891253 | 208802 | 6689.53 | 72.13% | 2.23% |
| A2 | 29.891254 | 244649 | | |
| B2 | 29.891254 | 234262 | | |
| C2 | 29.891254 | 260760 | 13351.64 | 82.19% | 4.45% |
| A3 | 29.891272 | 199973 | | |
| B3 | 29.891272 | 220701 | | |
| C3 | 29.891272 | 228481 | 14735.92 | 72.13% | 4.91% |

Sample 2

A) compound concentration: 100 pmol/10e6 WBCs

| compound internal reference No. | Mean | Mean standard deviation | Recovery rate | standard deviation |
|---|---|---|---|---|
| A1 | 29.891253 | 178919 | | | |
| B1 | 29.891253 | 197130 | | 62.59% | 3.04% |
| C1 | 29.891253 | 187224 | 187757.67 | 9117.22 | |
| A2 | 29.891254 | 185100 | | | |
| B2 | 29.891254 | 200184 | | 65.69% | 3.58% |
| C2 | 29.891254 | 205917 | 197067.00 | 10752.84 | |
| A3 | 29.891272 | 161504 | | | |
| B3 | 29.891272 | 201424 | | 62.11% | 7.22% |
| C3 | 29.891272 | 196021 | 186316.33 | 21657.26 | |

B) compound concentration: 1 nmol/10e6 WBCs

| compound internal reference No. | Mean | Mean standard deviation | Recovery rate | standard deviation |
|---|---|---|---|---|
| A1 | 29.891253 | 239105 | | | |
| B1 | 29.891253 | 240632 | | 79.02% | 1.65% |
| C1 | 29.891253 | 231420 | 237052.33 | 4937.14 | |
| A2 | 29.891254 | 244396 | | | |
| B2 | 29.891254 | 244304 | | 81.79% | 0.59% |
| C2 | 29.891254 | 247428 | 245376.00 | 1777.68 | |
| A3 | 29.891272 | 241232 | | | |
| B3 | 29.891272 | 254894 | | 82.47% | 2.31% |
| C3 | 29.891272 | 246129 | 247418.33 | 6921.66 | |

Conclusion: The Cholesterol-mono linker molecule (i.e. a compound containing a single hydrophobic moiety cholesterol) shows similar cell immobilization characteristics compared dual linker molecules (i.e. compounds containing two hydrophobic moieties).

Example 5: Stabilization of Cells Using Compounds Useful in Methods of the Invention The effect of compounds useful in methods of the invention on stabilizing cells and on immobilization was determined.

Figure 14:
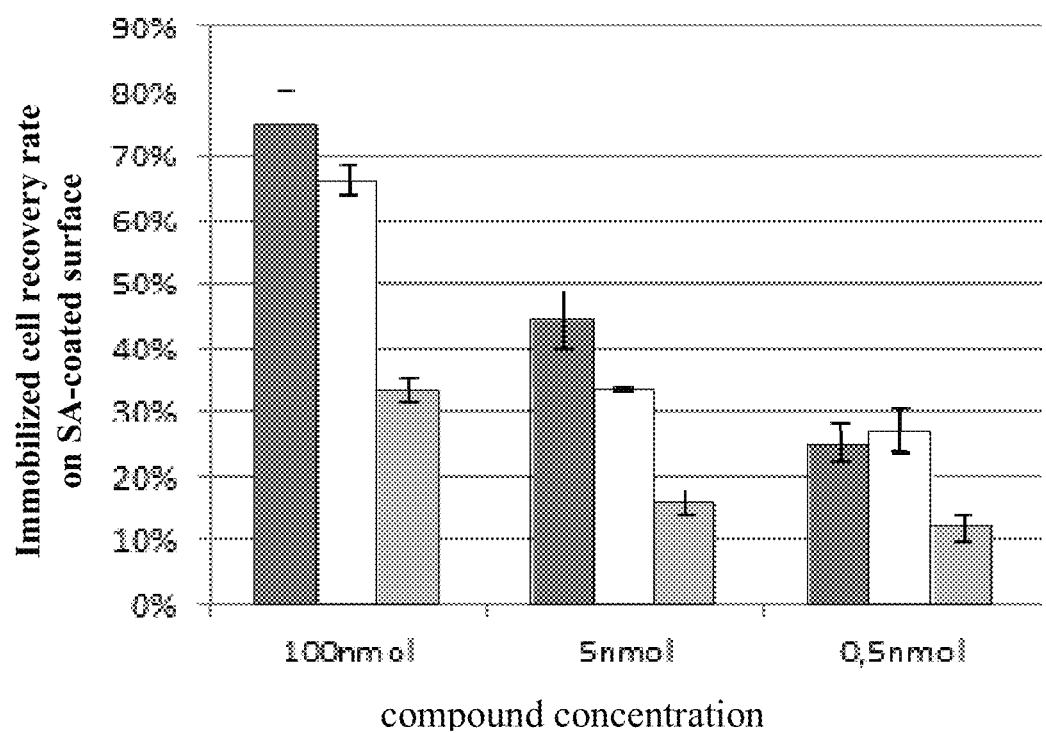
FIG. 14: shows WBC recovery rate after centrifugation and cell immobilization using different molecules. Molecule probes HH1749*, HH1750* and HH1755* show different performance concerning cell immobilization rate at different concentrations. The higher the linker concentration, the higher the cell immobilization rate.
Figure 15:
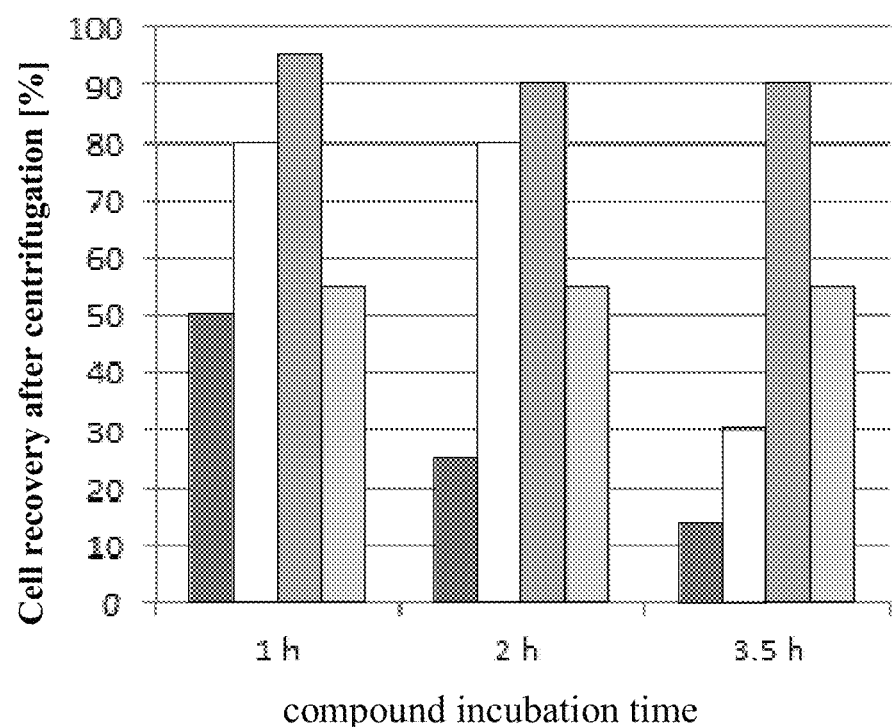
FIG. 15: shows WBC recovery rate after centrifugation using different compounds useful in methods of the invention at different points of time. Molecules A and B (A: Cholesteryl-TEG-Cholesteryl-TEG-(SpacerC18)7-Fluos-Biotin-TEG; B: Biotin-PEG-Lysin-(C18)2) show different performance concerning recovery rate after centrifugation. Respective left column: w/o compound of invention; respective second column from left: 0.35 nmol molecule A; respective third column from left: 100 nmol molecule B; respective right column: 0.5 nmol molecule B. The higher the molecule concentration, the higher the cell recovery rate after centrifugation. Molecule B enables cell immobilization within 3.5 hours. Centrifugation characteristics: 10 min, 300×g.

A) WBC Recovery Rate after Centrifugation and Cell Immobilization Using Different Molecules As shown in FIG. 14, molecule probes HH1749*, HH1750* and HH1755* (*Biotin-PEG-Lysin-(C18)2) show different performance concerning recovery rate after centrifugation: The higher the concentration of the molecule, the higher the cell recovery rate after centrifugation. Centrifugation characteristics: 10 min, 300×g. As can be seen from FIG. 15, molecule probes HH1749*, HH1750* and HH1755* show different performance concerning cell immobilization rate at different concentrations. The higher the linker concentration, the higher the cell immobilisation rate.

Figure 16:
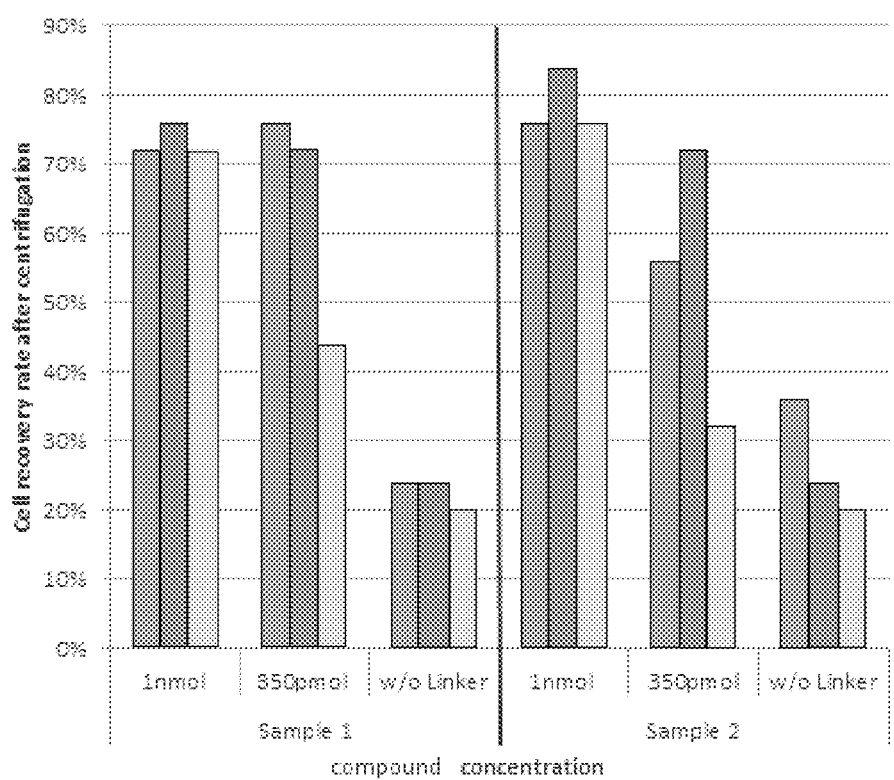
FIG. 16: shows WBC recovery rate after centrifugation with different experimenters. The respective left, middle and right columns per assay represent different Experimenters 1, 2 and 3. The higher the molecule concentration, the higher the cell recovery rate after centrifugation. Moreover, cell stabilization is independent on the experimenter. Centrifugation characteristics: 10 min, 300×g. Molecule: Cholesteryl-TEG-Cholesteryl-TEG-(SpacerC18)7-Fluos-Biotin-TEG.

B) WBC Recovery Rate after Centrifugation Using Different Compounds—Different Points of Time As can be seen from FIG. 16, molecules A and B (A: Cholesteryl-TEG-Cholesteryl-TEG-(SpacerC18)7-Fluos-Biotin-TEG; B: Biotin-PEG-Lysin-(C18)2) show different performance concerning recovery rate after centrifugation. The higher the molecule concentration, the higher the cell recovery rate after centrifugation. Molecule B enables cell immobilization within 3.5 hours. Centrifugation characteristics: 10 min, 300×g. A: Choleseryl-TEG-Cholesteryl-TEG-(SpacerC18)7-Fluos-Biotin-TEG. B: Biotin-PEG-Lysin-(C18)2

C) WBC Recovery Rate after Centrifugation—Different Experimenters

Figure 17:
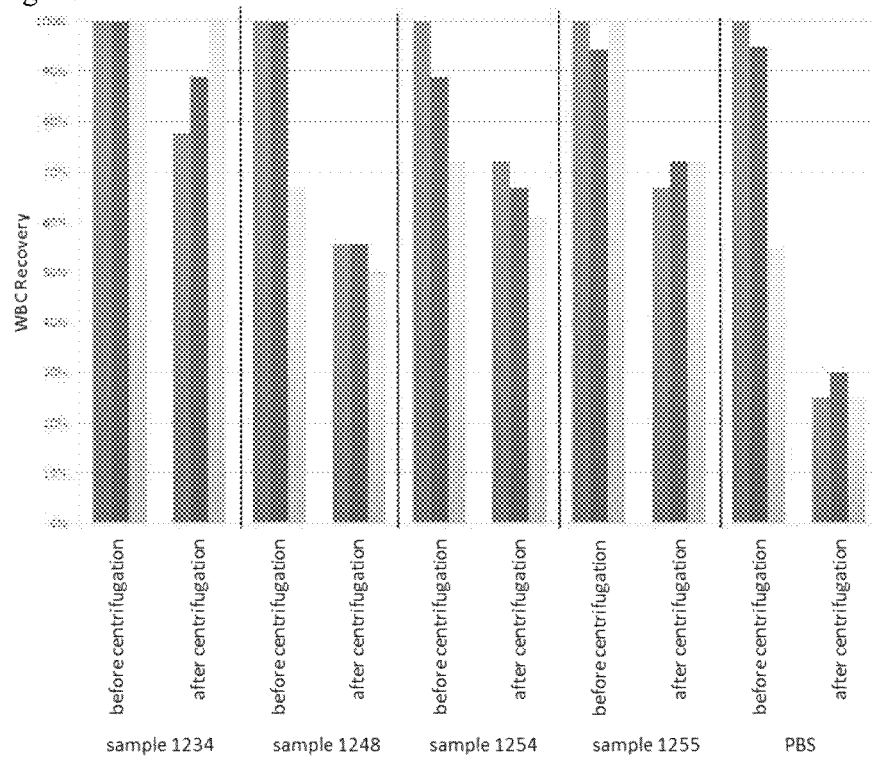
FIG. 17: shows WBC recovery rate after centrifugation at different points of time and centrifugation settings. Following molecules were tested: 1234: 5'-(Cholesteryl-TEG)2-Spacer C18-dT-Biotin-TEG-3'; 1248: 3'-(Cholesteryl-TEG) 2-PEG2000-Fluos-Biotin-TEG-5' INVERS; 1254: 3'-(Cholesteryl-TEG)2-SpacerC18-Fluos-Biotin-TEG-5' INVERS; 1255: 3'-(Myristic acid)2-PEG2000-dT-Biotin-TEG-5' INVERS. All molecules enable cell immobilization within 2 hours. WBCs in PBS are damaged during centrifugation at 300×g for 20 min. Molecule 1234 shows the best performance followed by compound 1255 and 1254. Centrifugation characteristics: 20 min, 300×g. Respective left column: 10 min incubation with molecule. Respective middle column: 1 h min incubation with molecule. Respective right column: 2 h incubation with molecule.

As can be seen from FIG. 17, the higher the molecule concentration, the higher the cell recovery rate after centrifugation. Moreover, cell stabilization is independent on the experimenter. Centrifugation characteristics: 10 min, 300×g. Molecule: Cholesteryl-TEG-Cholesteryl-TEG-(SpacerC18)7-Fluos-Biotin-TEG.

Figure 18:
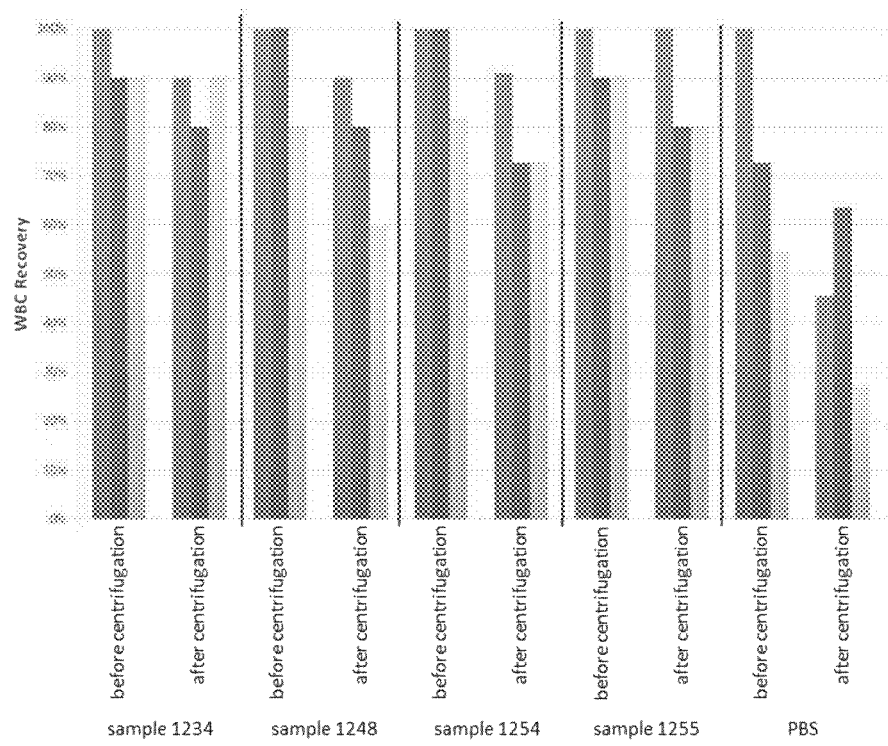
FIG. 18: shows WBC recovery rate after centrifugation at different points of time and centrifugation settings. Following molecules were tested: 1255: 3'-(Myristic acid)2-PEG2000-dT-Biotin-TEG-5' INVERS; 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG)2-SpacerC18-Fluos-Biotin-TEG-5' INVERS. All molecules enable cell immobilization within 2 hours. WBCs in PBS are damaged during centrifugation at 500×g for 20 min. Molecule 1234 shows the best performance followed by molecule 1255 and 1254. Centrifugation characteristics: 20 min, 500×g. Respective left column: 10 min incubation with molecule. Respective middle column: 1 h min incubation with molecule. Respective right column: 3 h incubation with molecule.

D) WBC Recovery Rate after Centrifugation—Different Points of Time and Centrifugation Settings The results of the first experiment are shown in FIG. 18. Following molecules were tested:
 1234: 5'-(Cholesteryl-TEG)2-Spacer C18-dT-Biotin-TEG-3'
 1248: 3'-(Cholesteryl-TEG)2-PEG2000-Fluos-Biotin-TEG-5' INVERS 1254: 3'-(Cholesteryl-TEG)2-SpacerC18-Fluos-Biotin-TEG-5' INVERS
 1255: 3'-(Myristic acid)2-PEG2000-dT-Biotin-TEG-5' INVERS All molecules enable cell immobilization within 2 hours
WBCs in PBS are damaged during centrifugation at 300×g for 20 min
Molecule 1234 shows the best performance followed by compound 1255 and 1254
Centrifugation characteristics: 20 min, 300×g.

Figure 19:
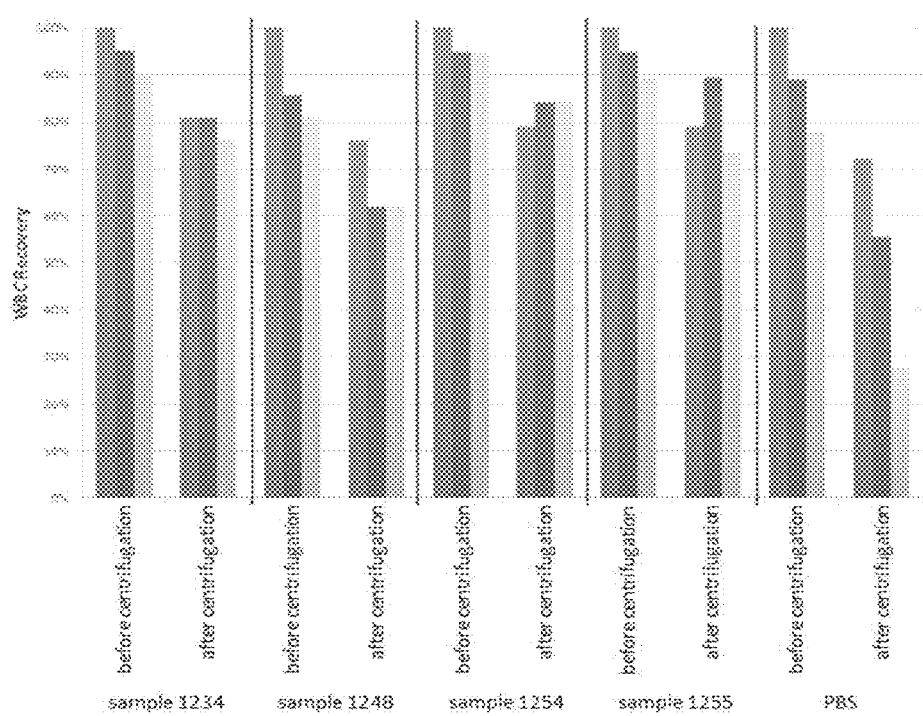
FIG. 19: shows WBC recovery rate after centrifugation at different points of time and centrifugation settings. Following molecules were tested: 1255: 3'-(Myristic acid)2-PEG2000-dT-Biotin-TEG-5' INVERS; 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG)2-SpacerC18-Fluos-Biotin-TEG-5' INVERS. All molecules enable cell immobilization within 2 hours. WBCs in PBS are damaged during centrifugation at 1000×g for 20 min. Centrifugation characteristics: 20 min, 1000×g. Respective left column: 10 min incubation with molecule. Respective middle column: 1 h min incubation with molecule. Respective right column: 2 h incubation with molecule.
Figure 20:
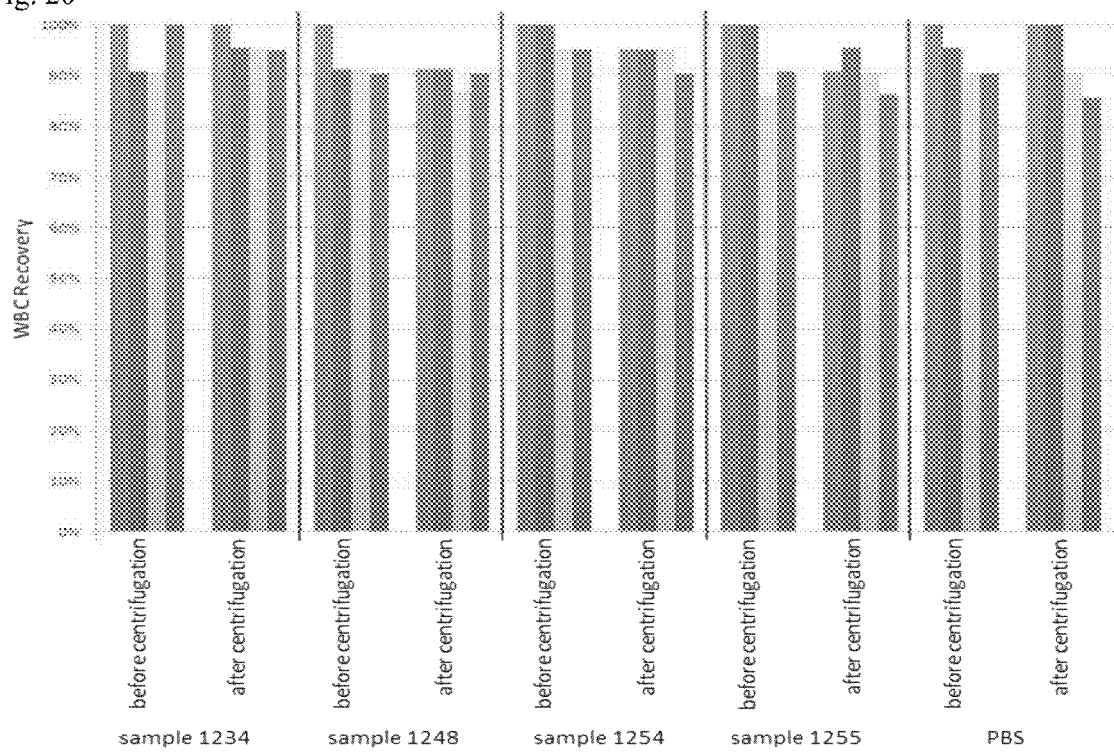
FIG. 20: shows Jurkat cell recovery rate after centrifugation at different points of time. Respective columns from left: 1: 10 min incubation with molecule. 2: 1 h incubation with molecule. 3: 3.5 h incubation with molecule. 4: 5.5 h min incubation with molecule. Following molecules were tested: 1255: 3'-(Myristic acid)-PEG2000-dT-Biotin-TEG-5' INVERS. 1234: 5'-(Cholesteryl-TEG)2-Spacer C18-dT-Biotin-TEG-3'; 1248: 3'-(Cholesteryl-TEG)2-PEG2000-Fluos-Biotin-TEG-5' INVERS; 1254: 3'-(Cholesteryl-TEG) 2-SpacerC18-Fluos-Biotin-TEG-5' INVERS. Jurkat culture cells are stable during centrifugation processes in PBS as well as using different molecules within 5.5 h. Centrifugation characteristics: 20 min, 500×g.

The results of the second experiment in this context are shown in FIG. 19. Following molecules were tested:
 1255: 3'-(Myristic acid)2-PEG2000-dT-Biotin-TEG-5' INVERS 1234: 5'-(Cholesteryl-TEG)2-Spacer C18-dT-Biotin-TEG-3'
 1248: 3'-(Cholesteryl-TEG)2-PEG2000-Fluos-Biotin-TEG-5' INVERS
 1254: 3'-(Cholesteryl-TEG)2-SpacerC18-Fluos-Biotin-TEG-5' INVERS The results are as follows:
All molecules enable cell immobilization within 2 hours
WBCs in PBS are damaged during centrifugation at 500×g for 20 min
Molecule 1234 shows the best performance followed by molecule 1255 and 1254
Centrifugation characteristics: 20 min, 500×g. The results of the third experiment in this context are shown in FIG. 20. Following molecules were tested:
 1255: 3'-(Myristic acid)2-PEG2000-dT-Biotin-TEG-5' INVERS
 1234: 5'-(Cholesteryl-TEG)2-Spacer C18-dT-Biotin-TEG-3'
 1248: 3'-(Cholesteryl-TEG)2-PEG2000-Fluos-Biotin-TEG-5' INVERS 1254: 3'-(Cholesteryl-TEG)2-SpacerC18-Fluos-Biotin-TEG-5' INVERS The results are as follows:

All molecules enable cell immobilization within 2 hours
WBCs in PBS are damaged during centrifugation at 1000×g for 20 min Centrifugation characteristics: 20 min, 500×g.

E) Jurkat Recovery Rate after Centrifugation—Different Points of Time

Figure 21A:
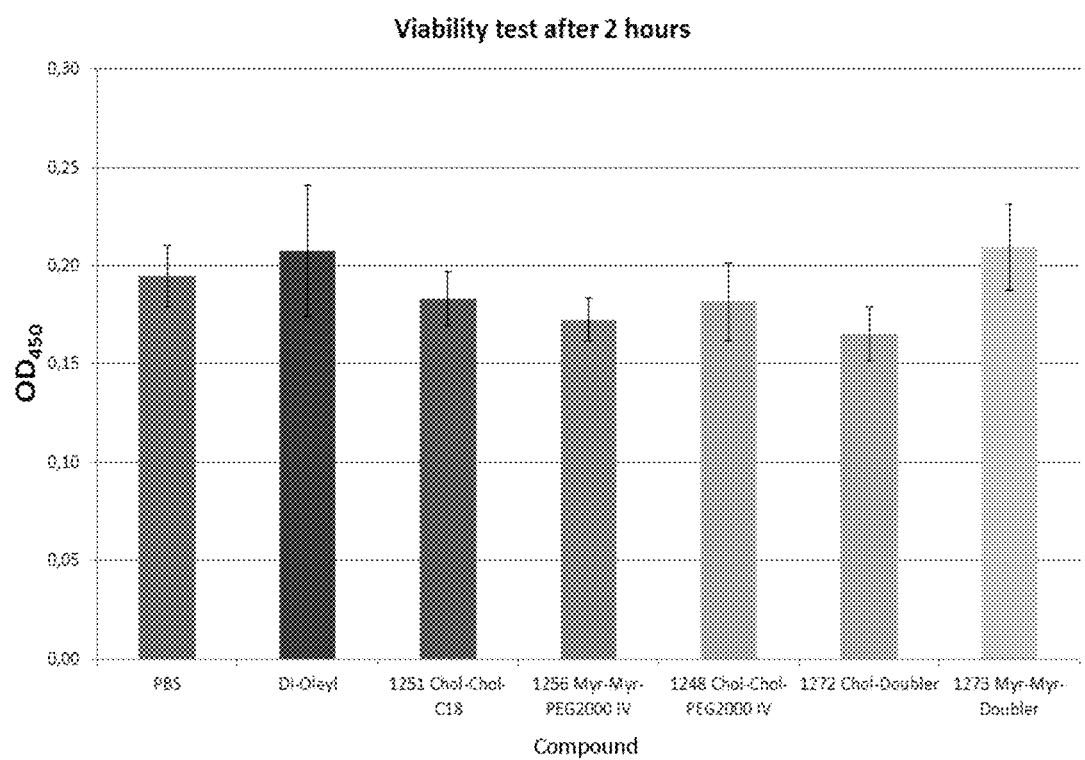
FIG. 21A: shows that tri-functional linker moieties do not influence cell viability. Cell viability test using WST-1 proliferation kit (RAS) was performed, employing different compounds for use according to the invention differing in the trifunctional linker moieties. The different linkers appear not to influence the cell viability during linker incubation time of 4 hours. Viability test after 2 hours.
Figure 21B:
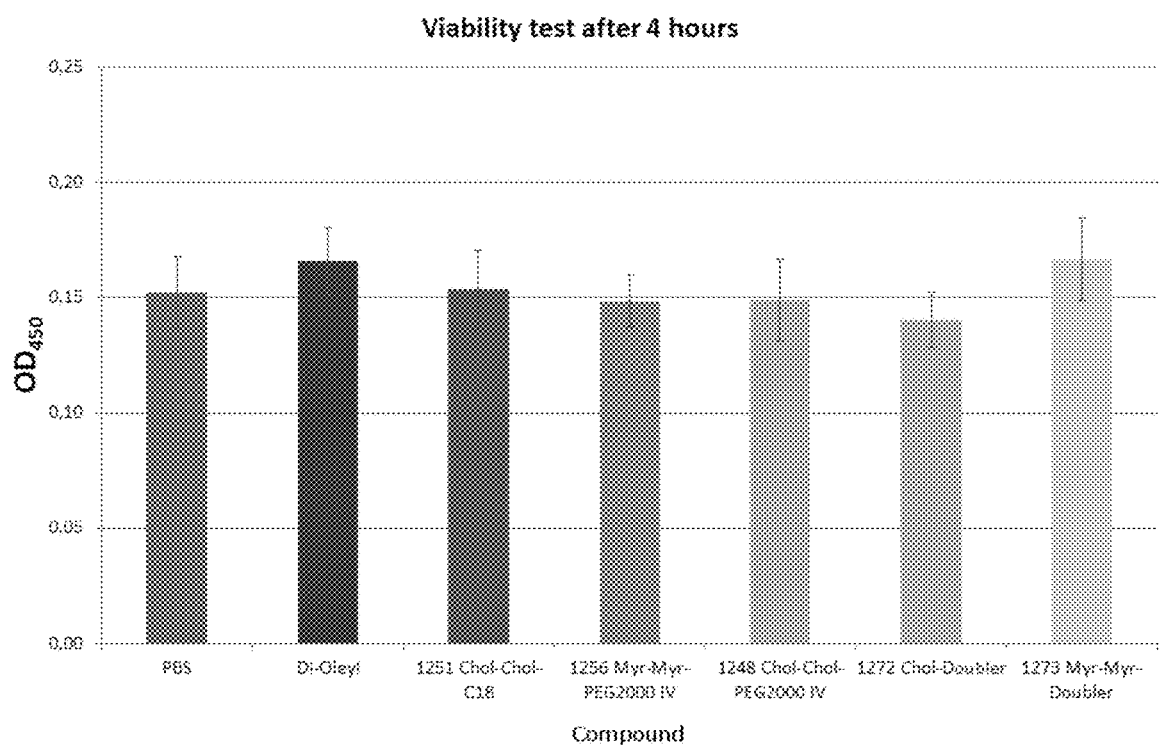
FIG. 21B: shows that tri-functional linker moieties do not influence cell viability. Cell viability test using WST-1 proliferation kit (RAS) was performed, employing different compounds for use according to the invention differing in the trifunctional linker moieties. The different linkers appear not to influence the cell viability during linker incubation time of 4 hours. Viability test after 4 hours.

The results of this experiment are shown in FIG. 21. Following molecules were tested:

1255: 3'-(Myristic acid)2-PEG2000-dT-Biotin-TEG-5' INVERS

1234: 5'-(Cholesteryl-TEG)2-Spacer C18-dT-Biotin-TEG-3'

1248: 3'-(Cholesteryl-TEG)2-PEG2000-Fluos-Biotin-TEG-5' INVERS

1254: 3'-(Cholesteryl-TEG)2-SpacerC18-Fluos-Biotin-TEG-5' INVERS

The results are as follows:

Jurkat culture cells are stable during centrifugation processes in PBS as well as using different molecules within 5.5 h.

Centrifugation characteristics: 20 min, 500×g.

Figure 22A:
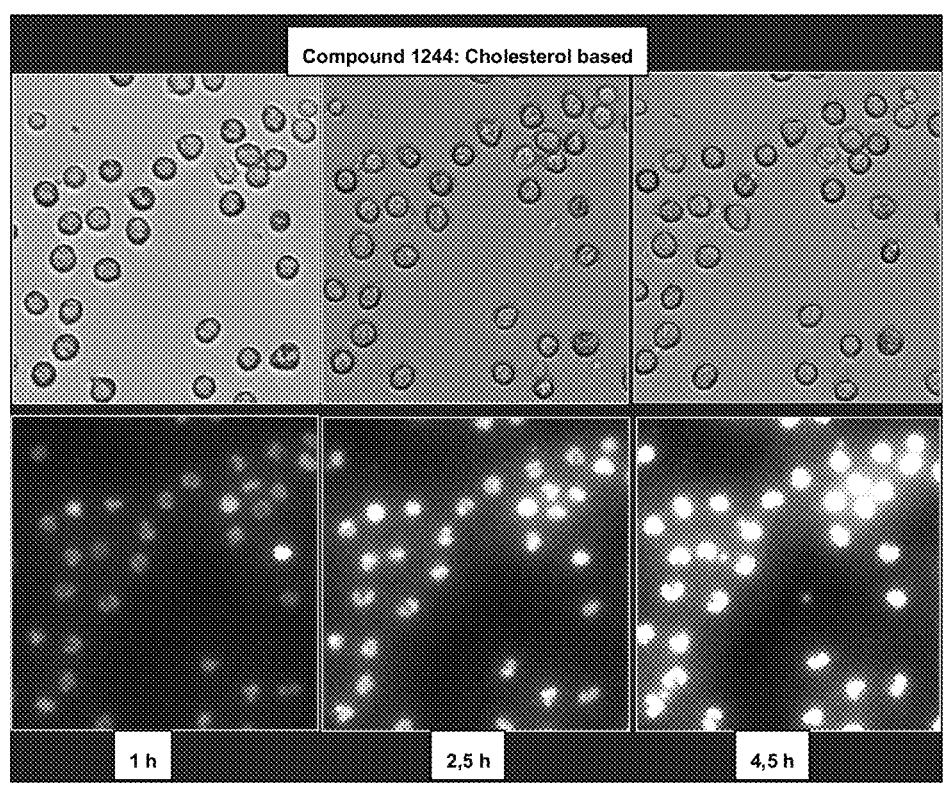
FIG. 22A: shows that tri-functional linker moieties do not influence cell viability. It was found that the tested compounds for use according to the invention, namely No. 1244 as compound with cholesterol-moiety do not influence cell morphology during linker incubation time of 4.5 hours. Left pictures: 1 h incubation. Middle pictures: 2.5 h incubation. Right pictures: 4.5 h incubation. Upper pictures: Brightfield. Lower pictures: DAPI.
Figure 22B:
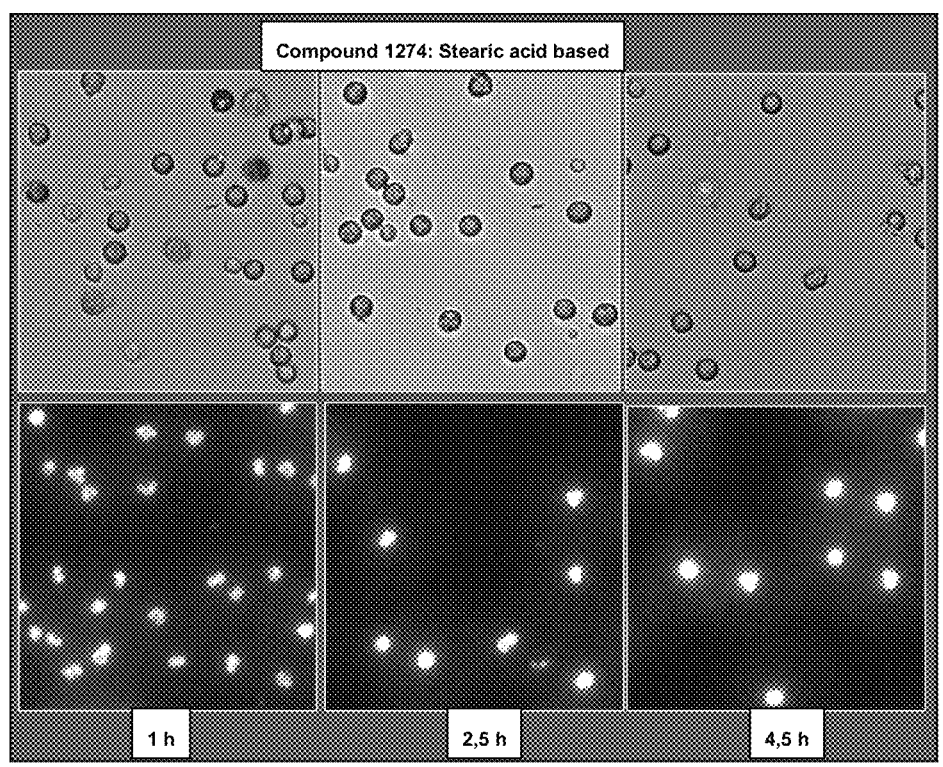
FIG. 22B: shows that tri-functional linker moieties do not influence cell viability. It was found that the tested compounds for use according to the invention, namely No. 1274 as compound with stearic acid-moiety, do not influence cell morphology during linker incubation time of 4.5 hours. Left pictures: 1 h incubation. Middle pictures: 2.5 h incubation. Right pictures: 4.5 h incubation. Upper pictures: Brightfield. Lower pictures: DAPI.

F) Tri-Functional Linker Moieties do not Influence Cell Viability The results of a first experiment in this context are shown in FIGS. 22 A and B.

Cell viability test using WST-1 proliferation kit (RAS) was performed, employing different molecules useful in methods of the invention differing in the trifunctional linker moieties.

⇒ The different linkers do not influence the cell viability during linker incubation time of 4 hours, as can be seen from FIG. 22.

Figure 23:
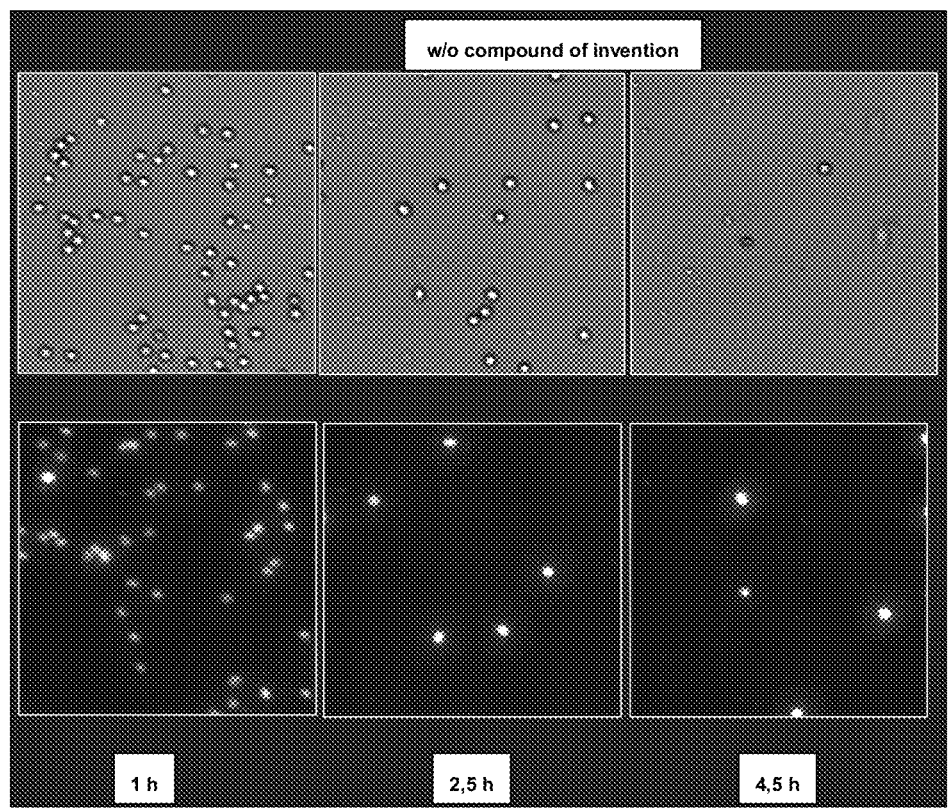
FIG. 23: shows cell morphology without linker incubation at different points of time. Without molecule useful in methods of the invention addition, cells diffuse away during an incubation time of 4.5 hours. Cell morphology is not influenced in left cells during the incubation time. Left pictures: 1 h incubation. Middle pictures: 2.5 h incubation. Right pictures: 4.5 h incubation. Upper pictures: Brightfield. Lower pictures: DAPI.

The results of a second experiment in this context are shown in FIGS. 23A and B. It was found that the tested molecules useful in methods of the invention (No. 1244 and 1274) do not influence cell morphology during linker incubation time of 4.5 hours.

Figure 24:
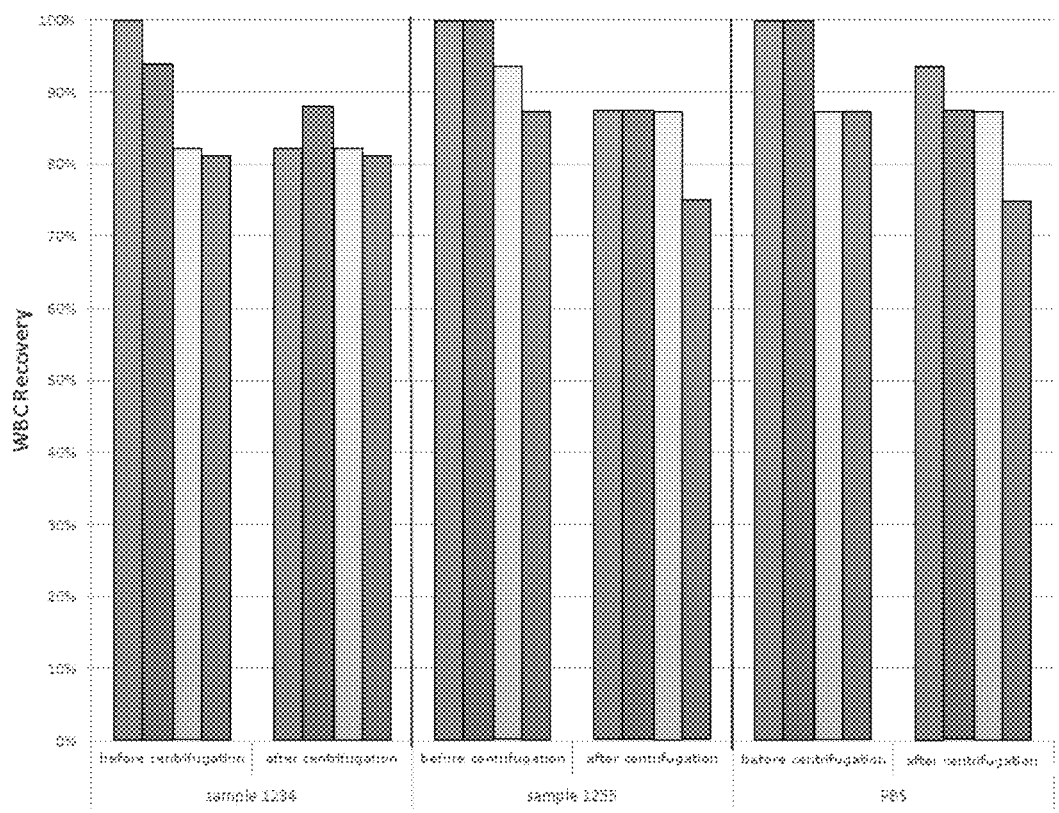
FIG. 24: shows MDA-MB468 cell recovery rate after centrifugation at different points of time. Respective columns from left: 1: 10 min incubation with molecule. 2: 1 h incubation with molecule. 3: 3 h incubation with molecule. 4: 5 h min incubation with molecule. Following compounds useful in methods of the invention were tested: 1234: 5'-(Cholesteryl-TEG)2-Spacer C18-dT-Biotin-TEG-3'; 1255: 3'-(Myristic acid)2-PEG2000-dT-Biotin-TEG-5' INVERS. MDA-MB468 culture cells are stable during centrifugation processes in PBS as well as using different compounds useful in methods of the invention within 5 h. Centrifugation characteristics: 20 min, 500×g.

G) Cell Morphology without Incubation with Molecule Useful in Methods of Invention—Different Points of Time The result of this experiment is shown in FIG. 24. Following was found:

Without molecule useful in methods of the invention addition, cells diffuse away during an incubation time of 4.5 hours Cell morphology is not influenced in left cells during the incubation time.

H) MDA-MB468 Recovery Rate after Centrifugation—Different Points of Time

The result of this experiment is shown in FIG. 25. Following compounds useful in methods of the invention were tested:

1234: 5'-(Cholesteryl-TEG)2-Spacer C18-dT-Biotin-TEG-3'

1255: 3'-(Myristic acid)2-PEG2000-dT-Biotin-TEG-5' INVERS

Following was found:

MDA-MB468 culture cells are stable during centrifugation processes in PBS as well as using different molecules useful in methods of the invention within 5 h.

Centrifugation characteristics: 20 min, 500×g.

Example 6: Comparison of SA-Plate (Streptavidin-Plate) Incubated with Compound Useful in Methods of the Invention Vs WBC (White Blood Cells) Incubated with Compound Useful in Methods of the Invention As starting material 5'-(Cholesteryl-TEG)2-PEG2000-Fluos-Biotin_TEG-3' INVERS (14530 pmol/µl) (Internal Reference No.: 29.891250), and a streptavidin treated MTP (Microcoat), 12 Well plate were used.

Erythrocyte lysis was performed as follows:

EDTA-whole blood 59.423 6.400 WBC/µl (Ambulanz Roche)

lysis buffer: 100 mM NH4Cl+5 mM Hepes+0.5 mM KHCO3+0.1 mM EDTA-K

Figure 2:
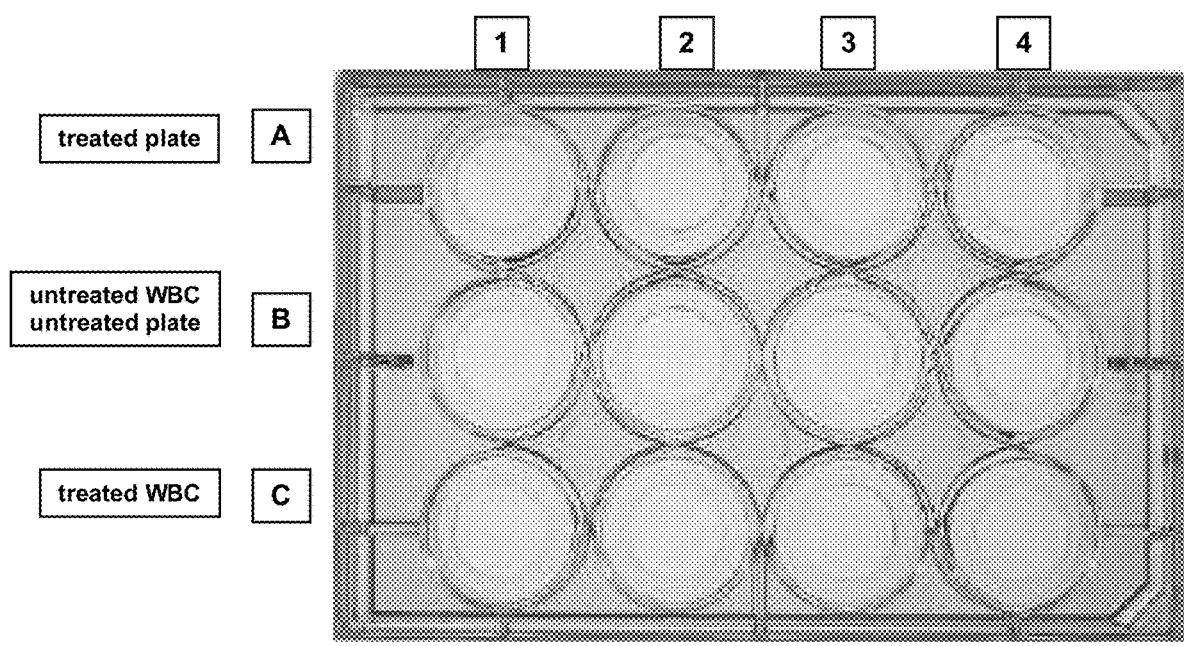
FIG. 2: shows the design of the Experiment of Example 6. 4× determination. Row A: 200 µl PBS introduced, 1 nmol of compound added thereto respectively, mixed, incubated about 30 min, washed 2×PBS, 800 µl PBS introduced, 300.000 WBC (untreated) added. Row B: 800 µl PBS introduced, 300.000 WBC (untreated) added. Row C: 10×10^6 WBC in 1 ml with 10 nmol compound of invention 10 min incubated, 800 µl PBS/Well introduced, 300.000 treated WBC respectively. The first MTP plate washed after 30 min 2× with PBS, overlayed with Höchst and incubated for 15 min. >Cellavista (Operator s9s5) measured. The second plate was measured after 90 min. The third plate was measured after 150 min.

Ca 1×8 ml whole blood filled in 50 ml Falcon tube with lysis buffer, incubate at room temperature for 10 min 15 min at 250 g centrifugated, pellet resuspended by pipetting in and out in lysis buffer; filled to 50 ml with lysis buffer 15 min 250 g centrifugated, pellet resuspended with PBS, filled to 50 ml with PBS, 15 min 250 g centrifugated, filled to 50 ml with PBS WBC measured at Sysmex 1:37.100 WBC/µl The design of the experiment on the plate is explained below (see FIG. 2):

3×12 Well MTP: Treatment of the WBC with compounds useful in methods of the invention:

4× determination:

Row A: 200 µl PBS introduced, 1 nmol of compound added thereto respectively, mixed, incubated about 30 min, washed 2×PBS, 800 µl PBS introduced, 300.000 WBC (untreated) added.

Row B: 800 µl PBS introduced, 300.000 WBC (untreated) added.

Row C: 10×10^6 WBC in 1 ml with 10 nmol compound useful in methods of invention 10 min incubated, 800 µl PBS/Well introduced, 300.000 treated WBC respectively.

The first MTP plate washed after 30 min 2× with PBS, overlaid with Höchst and incubated for 15 min. >Cellavista (Operator s9s5) measured.

The second plate was measured after 90 min.

The third plate was measured after 150 min.

The calculated results are shown in FIG. 3. A graph representing these results is depicted in FIG. 4. The plates of the experiments are shown in FIG. 5.

It was found that the method of the invention is clearly and surprisingly advantageous.

The invention claimed is:

1. A method of immobilizing an animal cell on a support, the method comprising a) providing a compound or salt thereof comprising two, three or four hydrophobic domains attached to a hydrophilic domain, wherein the two, three or four hydrophobic domains are independently covalently bound to said hydrophilic domain, and wherein the two, three or four hydrophobic domains each comprise cholesterol, and wherein the hydrophilic domain comprises a polyethylene glycol (PEG) moiety, and wherein the compound comprises a covalently linked linking group, wherein the linking group is biotin;

b) contacting an animal cell with the compound under conditions allowing the interaction of the compound with the membrane of the cell, thereby immobilizing the linking group on the surface of the cell; and c) contacting the linking group immobilized on the cell with a support capable of binding the linking group, thereby immobilizing the cell on the support.

2. The method of claim 1, wherein the hydrophilic domain of the compound has the formula of Formula (I):

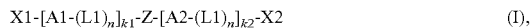
$$X1\text{-}[A1\text{-}(L1)_n]_{k1}\text{-}Z\text{-}[A2\text{-}(L1)_n]_{k2}\text{-}X2 \qquad (I),$$

wherein

Z is linear polyethylene glycol (PEG) moiety containing 1 to 100 —O—CH$_2$—CH$_2$— moieties, wherein the polyethylene glycol moiety optionally comprises 1 or more spacer moieties SP connecting two —O—CH$_2$—CH$_2$— moieties, and wherein the linear PEG moiety optionally comprises a linker moiety L3 at one or both ends, each L1 is a linker moiety selected independently from each other from the group consisting of phosphate, amide, carbamate, and ester, each n is either 0 or 1, selected independently from each other, A1 and A2 are bifunctional or trifunctional moieties selected independently from each other, and at least one A1 or A2 is trifunctional, k1 and k2 are integers between 0 and 10, selected independently from each other, and at least one of k1 and k2 is not 0, X1 and X2 are independently selected from hydrogen or a protecting group, L3 is independently selected from a linear alkyl or alkenyl chain with 1 to 10 C atoms, which is optionally (i) interrupted by 1 to 3 N, O or S atoms, and/or (ii) substituted by 1 to 4 hydroxyl, carbonyl, amino or thiol groups, and wherein the two, three or four hydrophobic domains are independently covalently bound to said hydrophilic domain via the trifunctional moieties.

3. The method of claim 2, wherein Z in Formula (I) has the following structure:

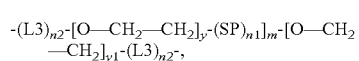
$$\text{-}(L3)_{n2}\text{-}[O\text{—}CH_2\text{—}CH_2]_{y}\text{-}(SP)_{n1}]_m\text{-}[O\text{—}CH_2\text{—}CH_2]_{y1}\text{-}(L3)_{n2}\text{-},$$

wherein

SP is a spacer moiety, each spacer moiety SP is selected independently from each other, each n1 is either 0 or 1, selected independently for each m moieties, each n2 is either 0 or 1, selected independently of each other, m is an integer from 1 to 100, y is an integer from 1 to 100, y1 is an integer from 0 to 30, with the proviso that y*m+y1≤100, L3 is independently selected from a linear alkyl or alkenyl chain with 1 to 10 C atoms, which is optionally (i) interrupted by 1 to 3 N, O or S atoms, and/or (ii) substituted by 1 to 4 hydroxyl, carbonyl, or thiol groups.

4. The method of claim 3, wherein (a) n1 is identical for the m moieties —[O—CH$_2$—CH$_2$]$_y$-(SP)$_{n1}$]—, and/or (b) y1 is 0, and/or (c) y is 4, 5, or 6, and n1 is 1, or (d) y is 4, 5, or 6, and n1 is 1, and/or (e) the spacer moieties SP are independently from each other selected from the group consisting of a phosphate, and a bifunctional moiety, and/or (f) n2 is both 0, or (g) one or both n2=1, and L3 is an alkyl group with 1 to 10 C atoms which optionally contains an amide group, carbonyl group, carbamate, and/or NH group.

5. The method of claim 2, wherein (a) the compound further comprises a label moiety, wherein a label moiety is covalently bound via the trifunctional moiety A2, and/or wherein one or more moiety(s) A2 are a label moiety, and/or wherein the label moiety is a fluorescent label, and/or (b) wherein a linking group is covalently bound via the trifunctional moiety A2.

6. The method of claim 2, wherein (a) the linkers L1 are independently selected from the group consisting of a phosphate, amide, carbamate, and ester group, and/or (b) moieties A1 and A2 are independently selected from a bifunctional group selected from the group consisting of a phosphate group, carbamate group, amide group, a moiety comprising a nucleobase, and a linear alkyl group having 1 to 10 C atoms and which alkyl chain contains functional groups at the terminal C-atoms, and a trifunctional moiety having 1 to 10 C atoms and comprising at least one —OH, —SH and/or at least one —NH2 group, and/or (c) the linkers L2 are independently selected from the group consisting of a phosphate, amide, carbamate, an ester group and a moiety

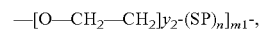
—[O—CH$_2$—CH$_2$]$_{y2}$-(SP)$_n$]$_{m1}$-, wherein SP and n are as defined in claim 3, y2 is an integer from 1 to 30, and m1 is an integer from 1 to 10.

7. A method of immobilizing a population of animal cells comprising a cell of interest on a support, the method comprising a) providing a compound as defined in claim 1;

b) contacting the population of the animal cells with the compound under conditions allowing the interaction of the compound with the membrane of the cells, thereby immobilizing the linking group on the surface of the cells;

c) contacting the linking group immobilized on the cell with a support capable of binding the linking group, thereby immobilizing the cells on the support; and d) optionally detecting the cell of interest immobilized on the support.

8. The method of claim 7 wherein the animal cell of interest is a white blood cell, a rare cell such as a circulating tumor cell, endothelial cell or epithelial cell.

9. The method of claim 1, wherein the animal cell is a cell in suspension and/or wherein the cell is a human cell, a vertebrate cell, or a mammalian cell.

* * * * *